United States Patent
Baniyash et al.

(10) Patent No.: US 10,955,415 B2
(45) Date of Patent: *Mar. 23, 2021

(54) CD247 AS A BIOMARKER FOR ASSESSING THE EFFECT OF CHEMOTHERAPEUTIC AND BIOLOGICAL DRUGS

(71) Applicant: YISSUM RESEARCH DEVELOPMENT COMPANY OF THE HEBREW UNIVERSITY OF JERUSALEM LTD., Jerusalem (IL)

(72) Inventors: Michal Baniyash, Mevasseret Zion (IL); Julia Kanterman, Jerusalem (IL); Moshe Sade-Feldman, Jerusalem (IL); Eliran Ish-Shalom, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 1282 days.

This patent is subject to a terminal disclaimer.

(21) Appl. No.: 14/348,621

(22) PCT Filed: Sep. 27, 2012

(86) PCT No.: PCT/IL2012/050393
§ 371 (c)(1),
(2) Date: Mar. 31, 2014

(87) PCT Pub. No.: WO2013/050998
PCT Pub. Date: Apr. 11, 2013

(65) Prior Publication Data
US 2017/0370932 A1 Dec. 28, 2017

Related U.S. Application Data

(60) Provisional application No. 61/542,897, filed on Oct. 4, 2011.

(51) Int. Cl.
*G01N 33/574* (2006.01)
*G01N 33/68* (2006.01)

(52) U.S. Cl.
CPC ....... *G01N 33/574* (2013.01); *G01N 33/6872* (2013.01); *G01N 2333/7051* (2013.01); *G01N 2800/44* (2013.01); *G01N 2800/52* (2013.01)

(58) Field of Classification Search
CPC ............ G01N 33/574; G01N 33/5008; G01N 33/5011; G01N 33/502; G01N 33/5047;
(Continued)

(56) References Cited

U.S. PATENT DOCUMENTS 9,188,588 B2* 11/2015 Baniyash ......... G01N 33/56972
2016/0209424 A1* 7/2016 Baniyash ......... G01N 33/56972

OTHER PUBLICATIONS

Zhang et al. TCRζ dim lymphocytes define populations of circulating effector cells that migrate to inflamed tissues. Blood 109 (10): 4328-4335 (May 15, 2007).*

(Continued)

*Primary Examiner* — Gailene Gabel
(74) *Attorney, Agent, or Firm* — Mark David Torche; Patwrite Law

(57) ABSTRACT

The invention relates to methods, kits and compositions using CD247 as a biomarker for assessing the efficacy and selecting an appropriate therapy such as chemotherapeutic, biological therapy or combined therapy for treating a subject suffering from a pathologic disorder that leads to a chronic-inflammatory condition.

16 Claims, 28 Drawing Sheets
Specification includes a Sequence Listing.

(58) Field of Classification Search
CPC .. G01N 33/505; G01N 33/5091; G01N 33/53; G01N 33/6872; G01N 2333/7051; G01N 2800/44; G01N 2800/52
See application file for complete search history.

(56) References Cited

OTHER PUBLICATIONS

Whiteside Down-regulation of TCRζ chain expression in T cells: a biomarker of prognosis in cancer. Cancer Immunol Immunother 53: 865-878 (2004).*

* cited by examiner

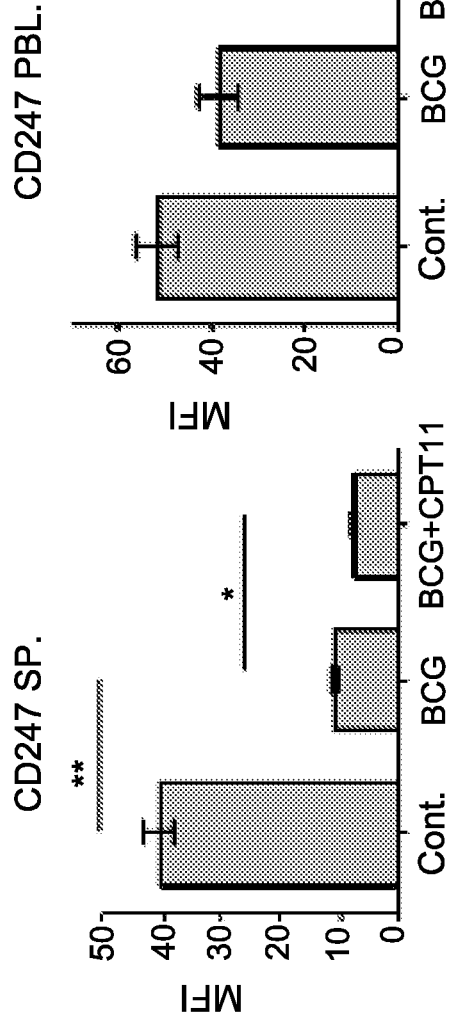
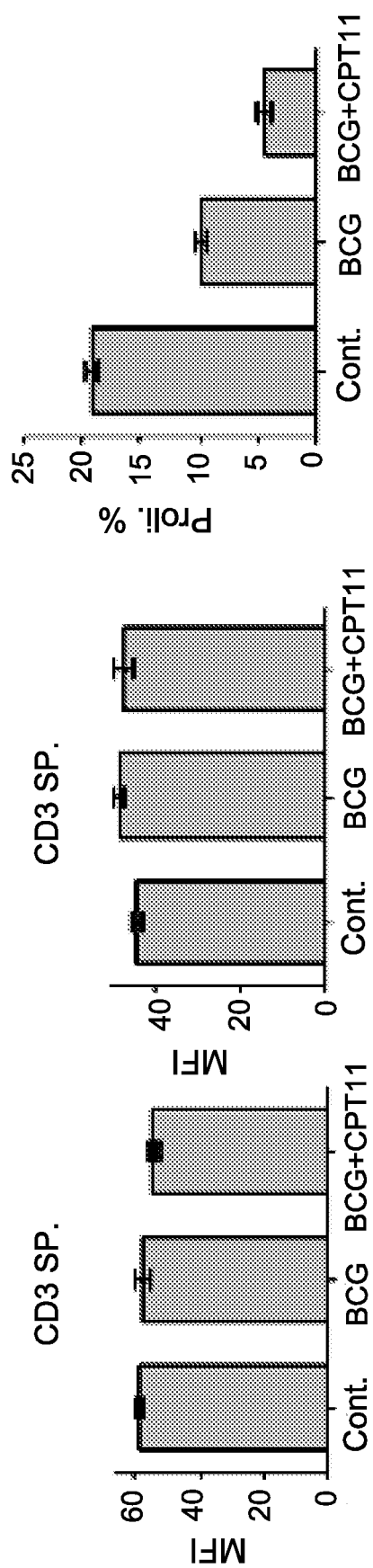
Figure 2A
Figure 2B
Figure 2C

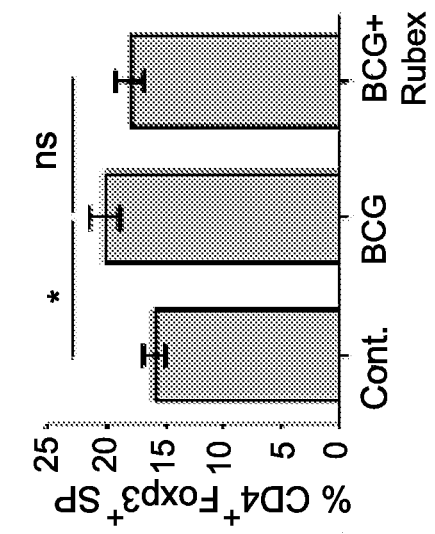
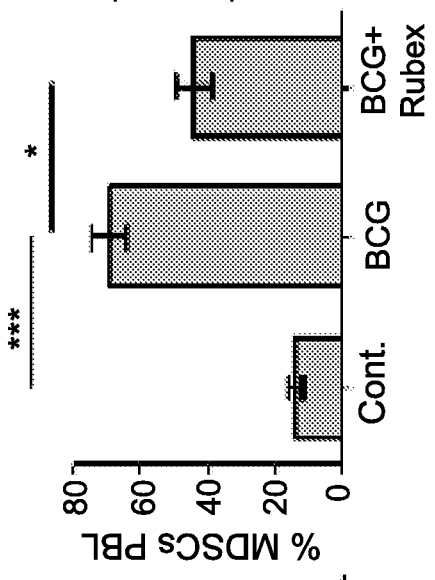
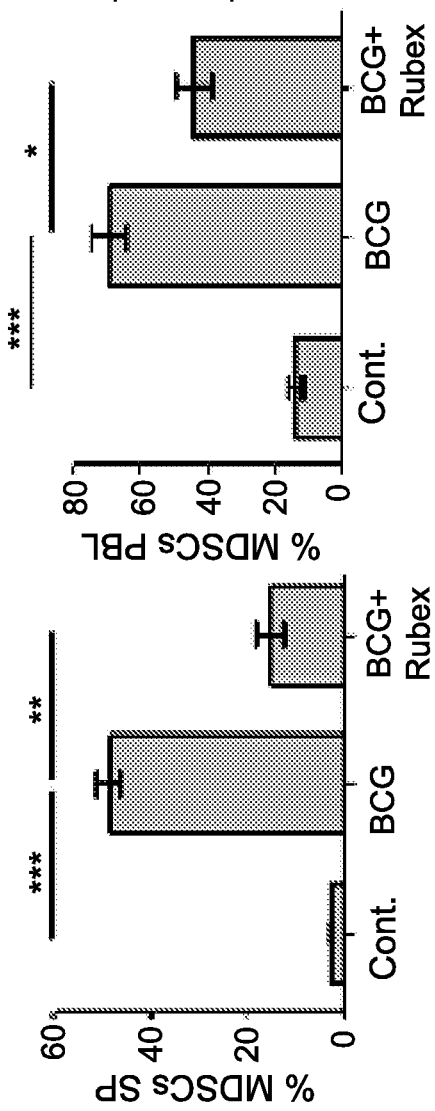

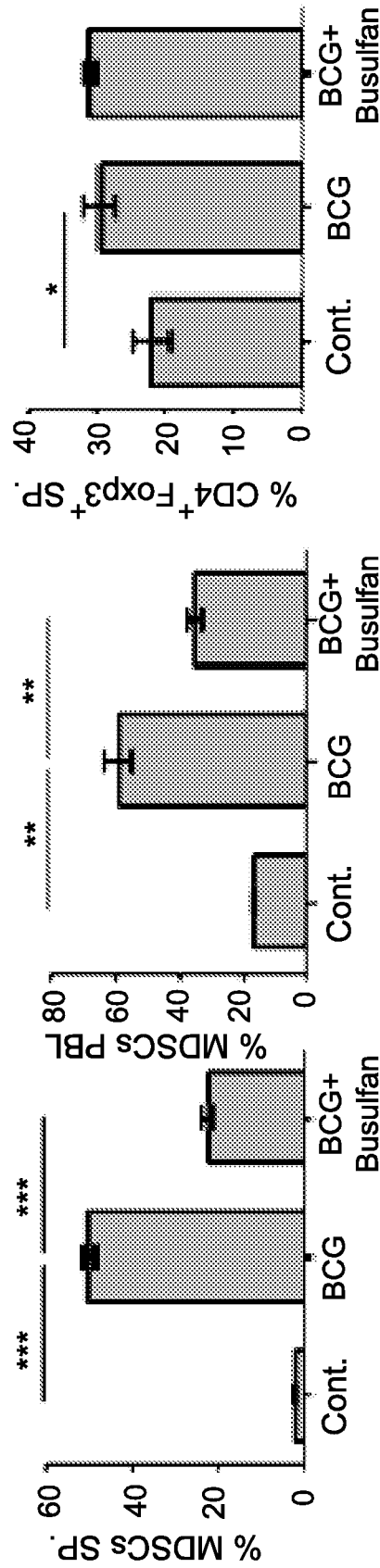

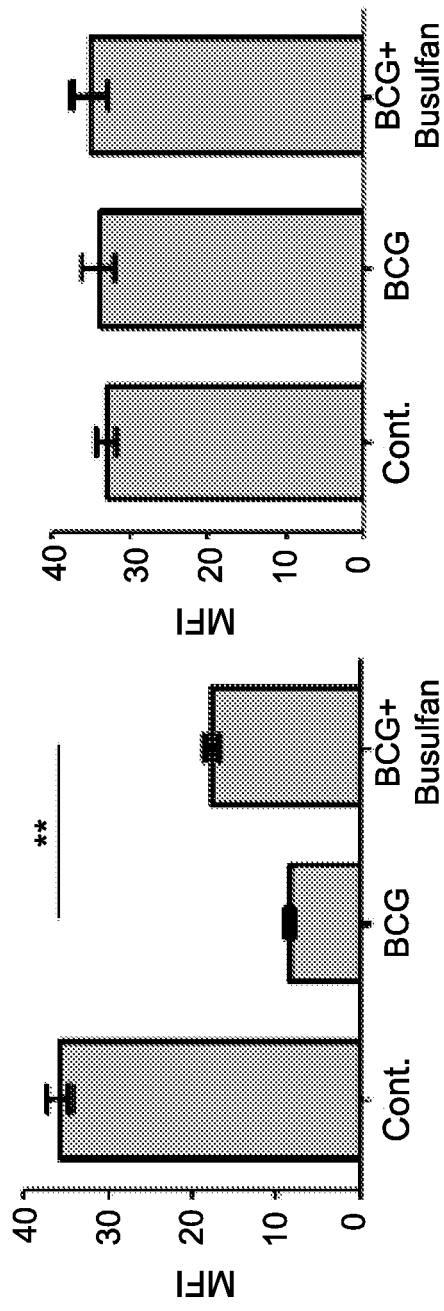
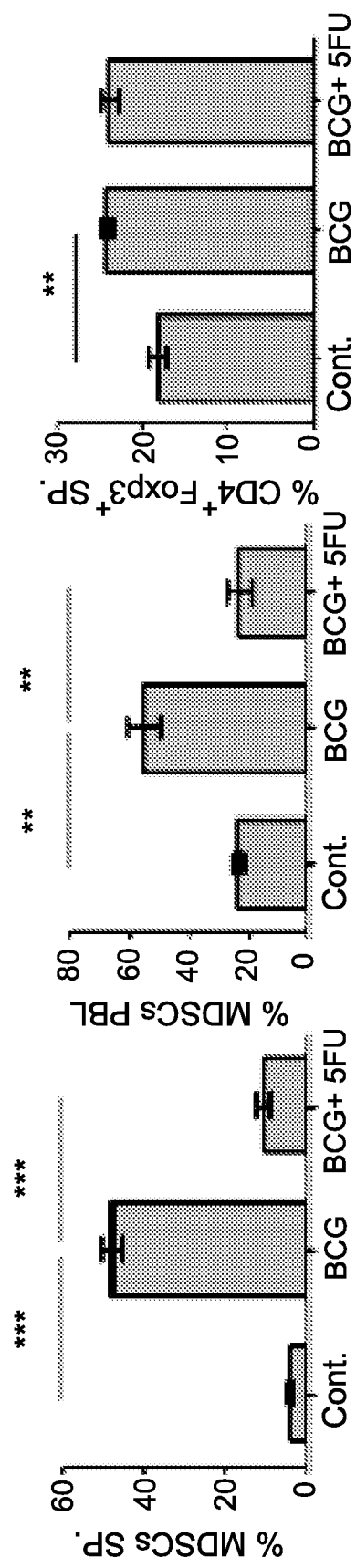
Figure 11A
Figure 11B
Figure 12A
Figure 12B
Figure 12C

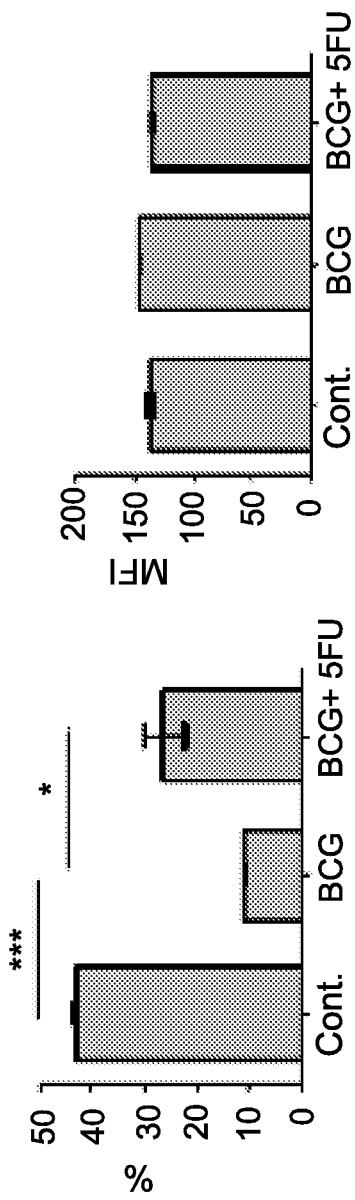
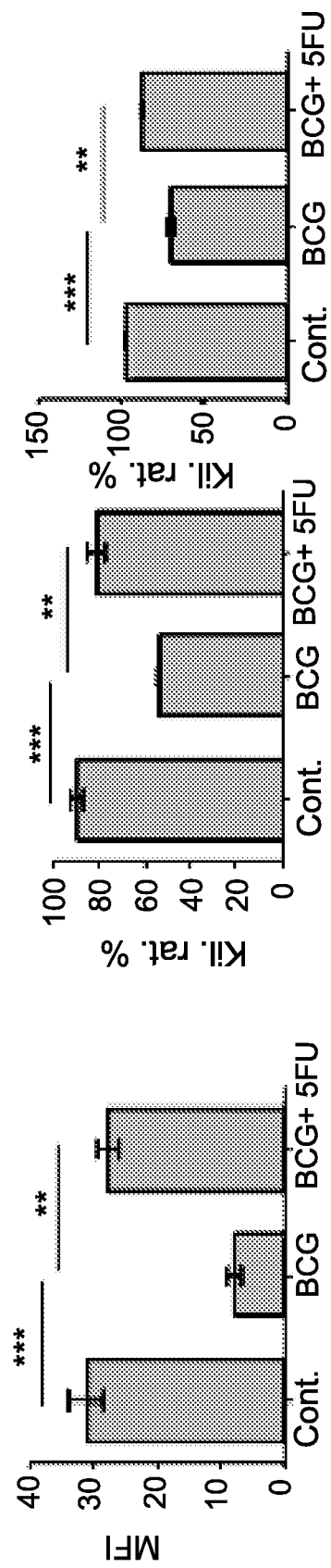

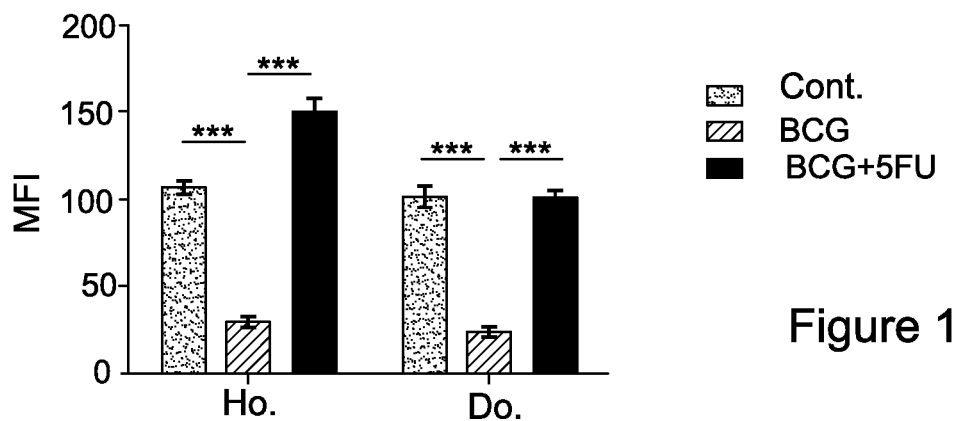
Figure 14
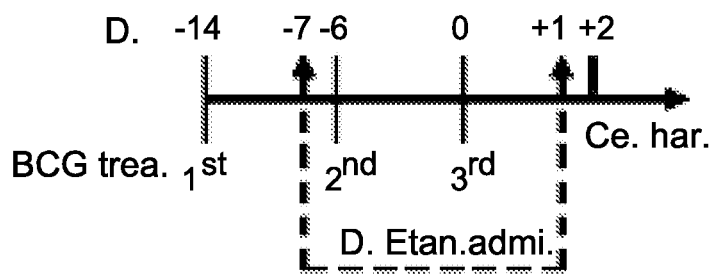
Figure 15A
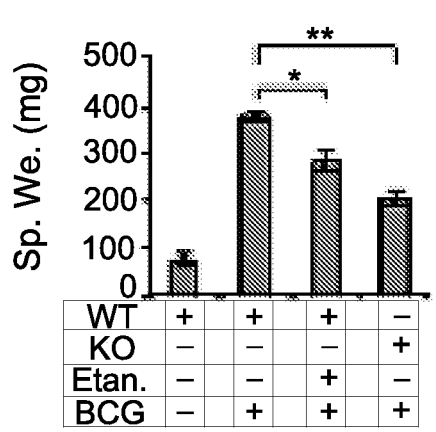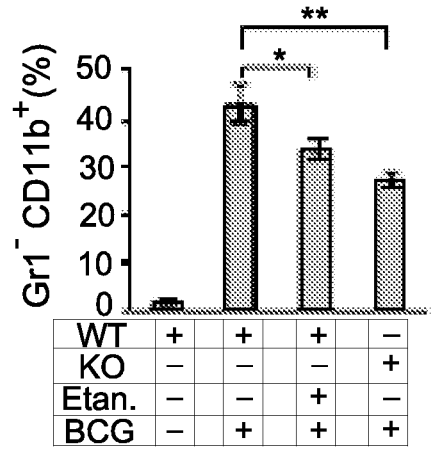
Figure 15B               Figure 15C
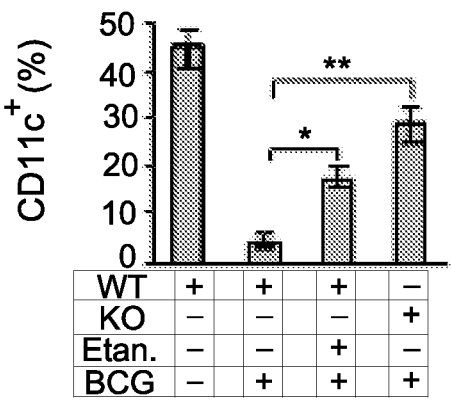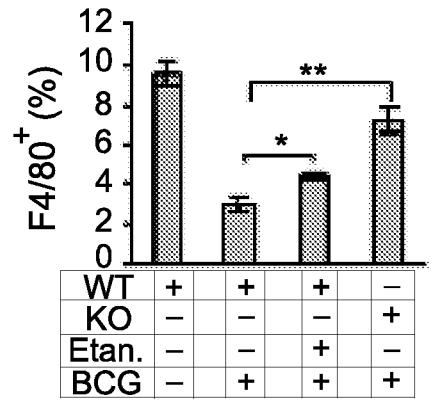
Figure 15D               Figure 15E

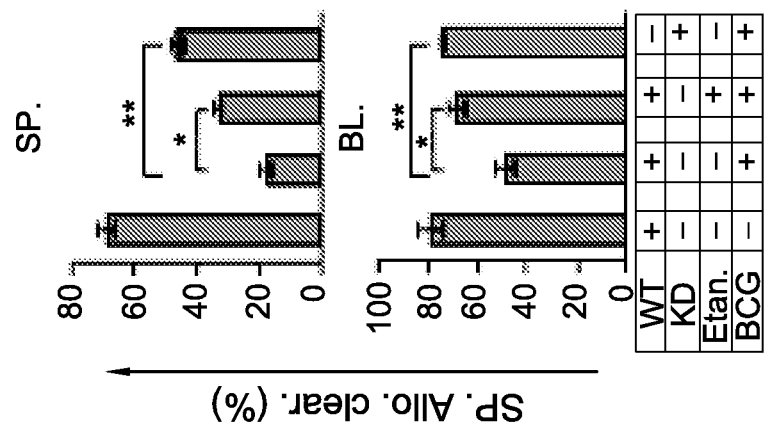
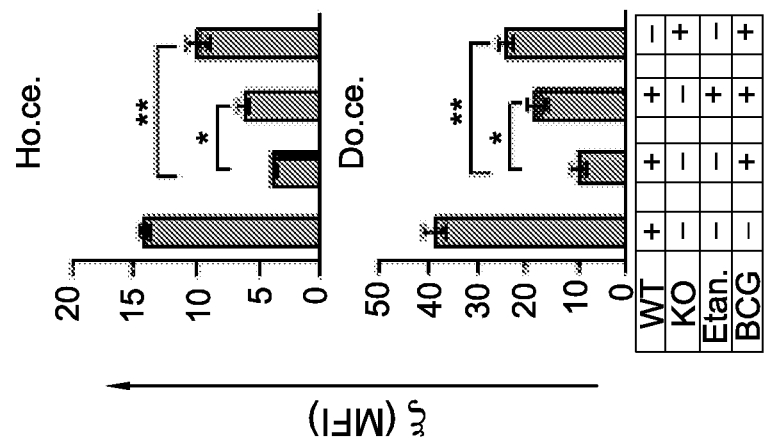
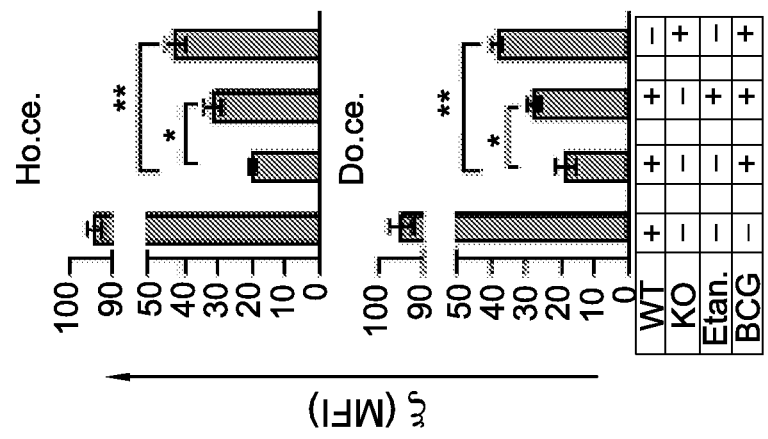

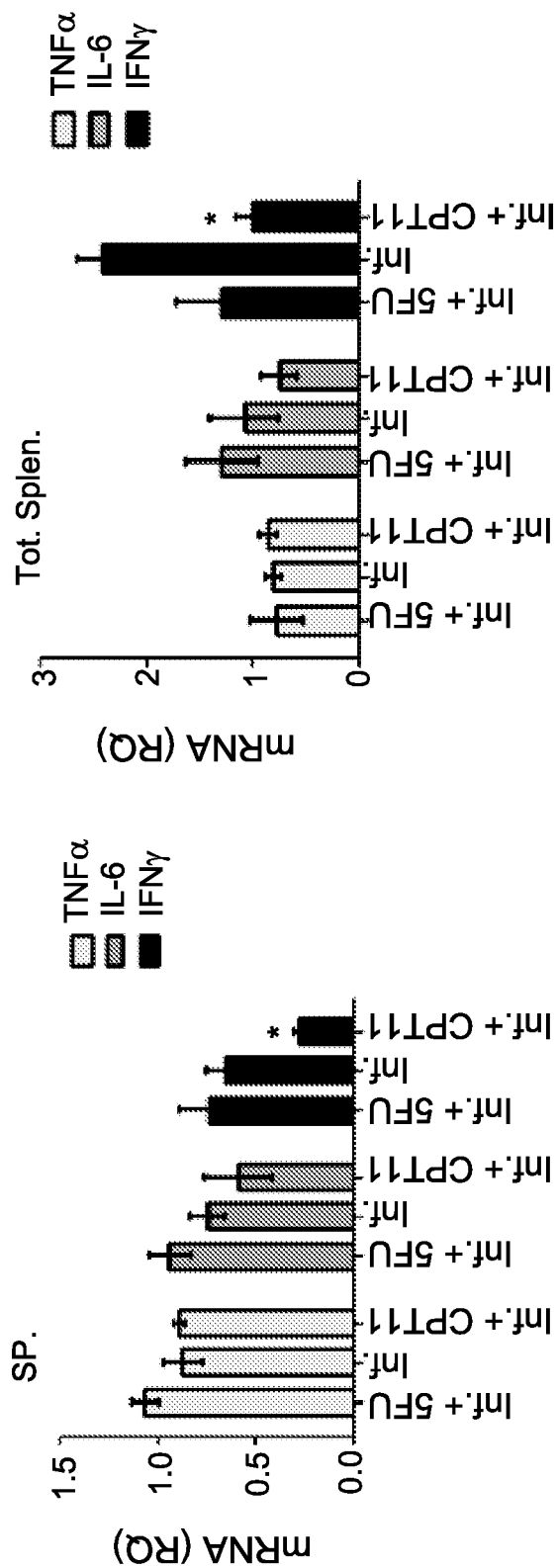
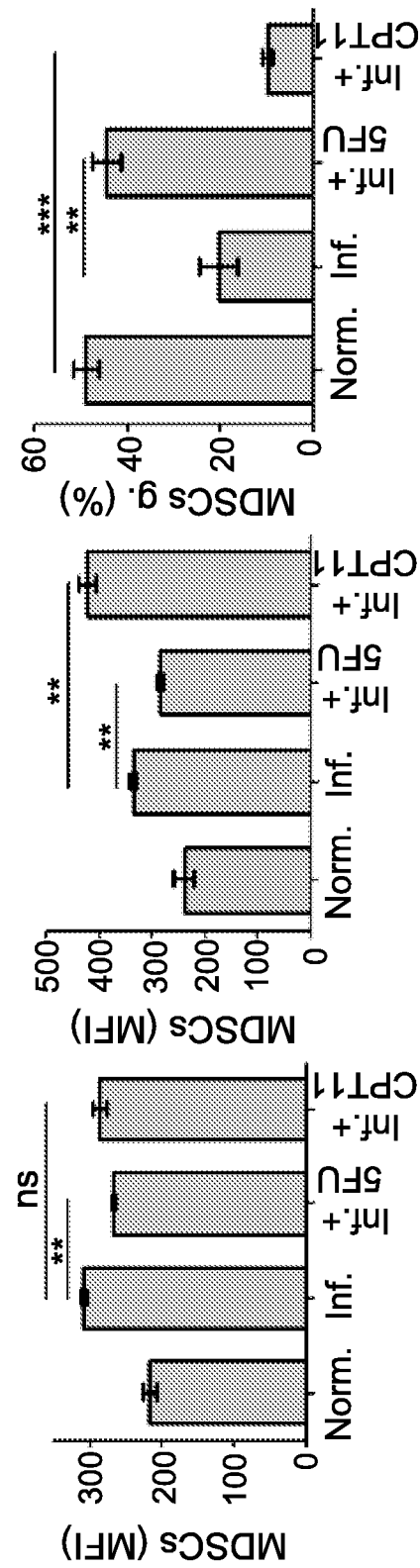
Figure 17C
Figure 17D
Figure 17E
Figure 17F

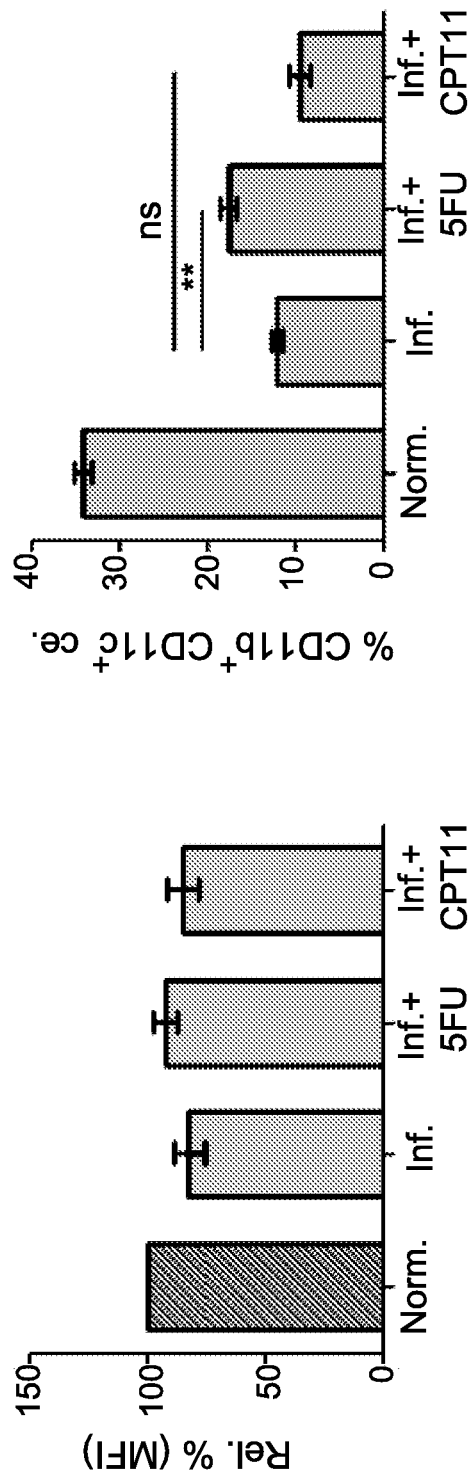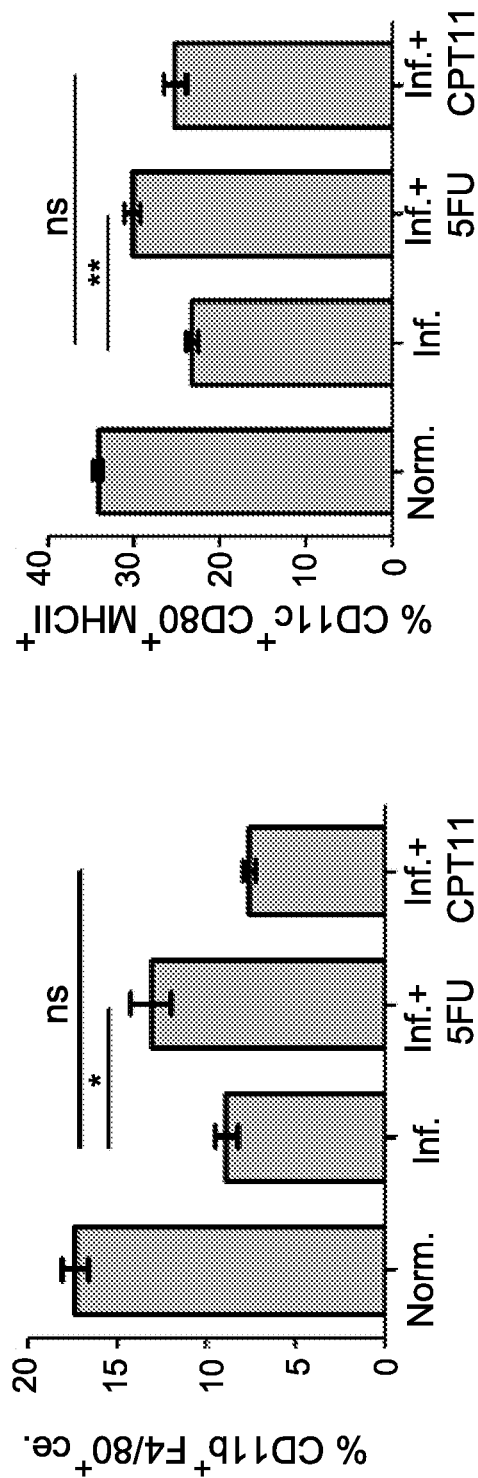

SEQUENCE LISTING

<160> NUMBER OF SEQ ID NOS: 4

<210> SEQ ID NO 1
<211> LENGTH: 163

<212> TYPE: PRT
<213> ORGANISM: Homo sapiens

<400> SEQUENCE: 1

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Glu Pro Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg

<210> SEQ ID NO 2
<211> LENGTH: 1472
<212> TYPE: DNA
<213> ORGANISM: Homo sapiens

<400> SEQUENCE: 2
cttttctcct aaccgtcccg gccaccgctg cctcagcctc tgcctcccag cctctttctg      60
agggaaagga caagatgaag tggaaggcgc ttttcaccgc ggccatcctg caggcacagt     120
tgccgattac agaggcacag agctttggcc tgctggatcc caaactctgc tacctgctgg     180
atggaatcct cttcatctat ggtgtcattc tcactgcctt gttcctgaga gtgaagttca     240
gcaggagcgc agagcccccc gcgtaccagc agggccagaa ccagctctat aacgagctca     300
atctaggacg aagagaggag tacgatgttt tggacaagag acgtggccgg gaccctgaga     360
tggggggaaa gccgagaagg aagaaccctc aggaaggcct gtacaatgaa ctgcagaaag     420
ataagatggc ggaggcctac agtgagattg gaatgaaagg cgagcgccgg aggggcaagg     480
ggcacgatgg cctttaccag gtctcagta cagccaccaa ggacacctac gacgccttc      540 acatgcaggc cctgcccct cgctaacagc caggggattt caccactcaa aggccagacc     600
tgcagacgcc cagattatga cacaggat gaagcattta caacccggtt cactcttctc       660
agccactgaa gtattcccct ttatgtacag gatgctttgg ttatatttag ctccaaacct     720
tcacacacag actgttgtcc ctgcactctt taagggagtg tactcccagg gcttacggcc     780
ctgccttggg ccctctggtt tgccggtggt gcaggtagac ctgtctcctg gcggttcctc     840
gttctccctg ggaggcgggc gcactgcctc tcacagctga gttgttgagt ctgttttgta     900
aagtccccag agaaagcgca gatgctagca catgccctaa tgtctgtatc actctgtgtc     960
tgagtggctt cactcctgct gtaaatttgg cttctgttgt caccttcacc tcctttcaag    1020

| | | | | |
|---|---|---|---|---|
| gtaactgtac | tgggccatgt | tgtgcctccc | tggtgagagg | gccgggcaga | ggggcagatg | 1080 |
| gaaaggagcc | taggccaggt | gcaaccaggg | agctgcaggg | gcatgggaag | gtgggcgggc | 1140 |
| aggggagggt | cagccagggc | ctgcgagggc | agcgggagcc | tccctgcctc | aggcctctgt | 1200 |
| gccgcaccat | tgaactgtac | catgtgctac | aggggccaga | agatgaacag | actgaccttg | 1260 |
| atgagctgtg | cacaaagtgg | cataaaaaac | agtgtggtta | cacagtgtga | ataaagtgct | 1320 |
| gcggagcaag | aggaggccgt | tgattcactt | cacgctttca | gcgaatgaca | aaatcatctt | 1380 |
| tgtgaaggcc | tcgcaggaag | acgcaacaca | tgggacctat | aactgcccag | cggacagtgg | 1440 |
| caggacagga | aaaacccgtc | aatgtactag | gg | | | 1472 |

<210> SEQ ID NO 3
<211> LENGTH: 164
<212> TYPE: PRT
<213> ORGANISM: Mus musculus

<400> SEQUENCE: 3

Met Lys Trp Lys Val Ser Val Leu Ala Cys Ile Leu His Val Arg Phe
1               5                   10                  15

Pro Gly Ala Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Ile Thr Ala
        35                  40                  45

Leu Tyr Leu Arg Ala Lys Phe Ser Arg Ser Ala Glu Thr Ala Ala Asn
    50                  55                  60

Leu Gln Asp Pro Asn Gln Leu Tyr Asn Glu Leu Asn Leu Gly Arg Arg
65                  70                  75                  80

Glu Glu Tyr Asp Val Leu Glu Lys Lys Arg Ala Arg Asp Pro Glu Met
                85                  90                  95

Gly Gly Lys Gln Gln Arg Arg Arg Asn Pro Gln Glu Gly Val Tyr Asn
            100                 105                 110

Ala Leu Gln Lys Asp Lys Met Ala Glu Ala Tyr Ser Glu Ile Gly Thr
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Thr
145                 150                 155                 160

Leu Ala Pro Arg

<210> SEQ ID NO 4
<211> LENGTH: 1191
<212> TYPE: DNA
<213> ORGANISM: Mus musculus

<400> SEQUENCE: 4

| | | | | | | |
|---|---|---|---|---|---|---|
| caaagccagc | agagactcca | tcagcgcctc | cttttctcct | catcctccca | ggcatagctg | 60 |
| cctctgcctc | tgcctctggg | taccatccca | gggaagcaga | agatgaagtg | gaaagtgtct | 120 |
| gttctcgcct | gcatcctcca | cgtgcggttc | ccaggagcag | aggcacagag | ctttggtctg | 180 |
| ctggatccca | aactctgcta | cttgctagat | ggaatcctct | tcatctacgg | agtcatcatc | 240 |
| acagccctgt | acctgagagc | aaaattcagc | aggagtgcag | agactgctgc | caacctgcag | 300 |
| gaccccaacc | agctctacaa | tgagctcaat | ctagggcgaa | gagaggaata | tgacgtcttg | 360 |
| gagaagaagc | gggctcggga | tccagagatg | ggaggcaaac | agcagaggag | gaggaacccc | 420 |
| caggaaggcg | tatacaatgc | actgcagaaa | gacaagatgg | cagaagccta | cagtgagatc | 480 |

```
ggcacaaaag gcgagaggcg gagaggcaag gggcacgatg gcctttacca gggtctcagc    540
actgccacca aggaccccta tgatgccctg catatgcaga ccctggcccc tcgctaacag    600
ccagggcatt tctccctcac gggcttcacc tgctgatgtc acttgtgaag gacagaggac    660
aaagcccccc tcagtttatt catttcccag ccaccatttc atgacgagga tggttctctc    720
acttgccaca tttgtcttct tcagttccag agcactgaac acagaacgtc atccctggac    780
tctctaaagg gagagccacc cttgctcttc caccccagcc ctgctcttgg gtcttctggc    840
aggctcctct ccttgcagag cccagcccta gctaggagtt gggggtggag ggtggggcac    900
taacacactc cctcctgcag ctagctgagt tcagtttgct ttgtaaagtc cccagagaag    960
ccctaggtac tgtgtgtatt gttctatggg tattgactcg ctccgctcct gctgtaaatt   1020
tggcttctgt tgtcacactt tgcagtgttg aggtaacatg taattaggcc acattgtgaa   1080
aggcagagag gcaggtacaa gggagtccag gtaaatgcca gccagaggtg gctcaaagaa   1140
gggaagcaac acacaaggaa ggttcctagc cacaggggaa cagtaacaag g            1191
```

CD247 AS A BIOMARKER FOR ASSESSING THE EFFECT OF CHEMOTHERAPEUTIC AND BIOLOGICAL DRUGS

TECHNOLOGICAL FIELD

The invention relates to personalized medicine. More specifically, the invention provides methods, kits and compositions for assessing the efficacy and selecting an appropriate therapy such as chemotherapeutic, biological therapy or combined therapy for treating a subject suffering from a pathologic disorder that leads to a chronic-inflammatory condition.

BACKGROUND OF THE INVENTION

Therapies of cancer that are based on the immune system have been used in clinical trials for years but were not shown yet as a successful strategy for an overall extension of survival [1-4]. Currently, the main strategy in the treatment of cancer is chemotherapy, sometimes accompanied with targeted or general immunotherapy [1, 4-7]. Chemotherapy protocols focus on the destruction of cancer cells, for example, by preventing cancer cells from further multiplying or by inducing cell death, thereby eliminating cancer cells from the body.

Chemotherapeutic drugs systemically affect the whole body by being transmitted through the bloodstream and are thus able to eliminate cancer cells at sites that are distant from the site of the original tumor [4, 8]. Unfortunately, during the course of such a process healthy cells are also affected, especially those that are naturally rapidly dividing [7]. While chemotherapy is advantageous in patients at initial stages of developing tumors, advanced cancer patients usually poorly benefit from such treatments, mostly without an option for a cure [9-11]. Thus, although chemotherapy is a very common and sometimes efficacious treatment, there is an urgent need for a less harmful and more targeted strategy, due to its toxic effects.

One of the proposed solutions in some cancer cases is immunotherapy, which is a more controlled therapeutic strategy [1-2, 4-7, 12]. Immunotherapy constitutes of a tumor specific biologic therapy that mimics or uses certain parts of the immune system to destruct or eliminate cancer cells. The concept of immunotherapy relies on the natural defense system of the body, which naturally protects against a variety of diseases [5, 7, and 13]. Immunotherapeutic strategies that are currently used include boosting the patient's own immune system, for example, by vaccination against cancer targets, by cytokine treatment that modulate the activity of the immune system of the patient, or by administrating to a patient engineered versions of normal components of the immune system (e.g. adoptive immune cell transfer, administering antitumor, anti-receptor, or anti-cytokine antibodies, administering soluble cytokine receptors, etc.). Due to the high specificity for cancer cells, the toxicity of immunotherapy is rather low, and in some cases, supports and complements chemotherapy treatment [1, 4-7].

To date, a great effort has been invested in the development of various cancer therapies, where immune and chemotherapeutic strategies are used separately or in various combinations. However, the major focus has been on following the patient's tumor response to the treatment, while the effects of such treatments on the tumor micro- and macro-environments and on the host immune system in general, which are key players in dictating the success rates of given therapies and disease regression, have been in many cases overlooked.

It is currently well established that in cancer patients, the generated tumor microenvironment exhibits features that support tumor growth, for example, by developing local chronic inflammatory response, which later turns systemic [14-18]. While chronic inflammation can directly support tumor growth by secreted factors and enriched populations of unique cells, which may lead to an enhanced tumor cell survival or proliferation and angiogenesis, chronic inflammation may also indirectly support tumor growth by inducing immunosuppression [14, 17 and 19], all leading to a failure of the patient's immune system in defeating the tumor. Therefore, in many cases, the success rates of the above-mentioned therapies are very limited, ensuing in malignant prospers and metastasis. Today there is an urgent need for biomarkers that are required to measure the host's immune status and inflammatory state prior to a given therapy, as well as during its course and following the therapy.

The inventors have previously established a mouse model system mimicking chronic inflammation induced immunosuppressive conditions WO 2005/025310. This publication further disclosed the use of CD247 as a marker for the immunological status of a patient suffering from a chronic inflammatory condition. Another previous publication of the inventors, WO 2009/125408, have demonstrated the use of CD247 as a diagnostic and prognostic marker for monitoring the immune status of patients suffering from chronic inflammatory conditions, specifically, diabetes.

Monitoring of the immune system function of cancer patients could enable to better evaluate the immune status and thus, a) identify responders vs. non-responders to immune-based therapies, b) evaluate therapy efficacies in cases of immune- or chemo-therapy, and c) follow disease regression or recurrence. Such a monitoring system is expected to lead to an intelligent selection of the timing and nature of drug/treatment to be used at the personalized level. Moreover, the quality of life of such patients could be significantly improved, fewer cases of tumor progression and metastasis are expected and the high expenses needed for continuous costly checkups could be less frequently performed, dramatically reducing the care costs.

References considered to be relevant as background to the presently disclosed subject matter are listed below:

[1] Baxevanis, C. N. et al., Cancer Immunology, Immunotherapy 58:317-324 (2009)
[2] Florescu, A. et al., Current oncology 1:e9-e18 (2011)
[3] Bodey, B. et al., Anticancer research 4:2665-2676 (2000)
[4] Ramakrishnan, R. and Gabrilovich, D. I. Cancer Immunology, Immunotherapy 60:419-423 (2011)
[5] Chong, G. and Morse, M. A. Expert Opinion on Pharmacotherapy, 6:2813-2820 (2005)
[6] Ramakrishnan, R. et al., Cancer Immunology, Immunotherapy, 57:1523-1529 (2008)
[7] Gomez, G. G. et al., Cancer treatment reviews, 27:375-402 (2001)
[8] Kannarkat, G. et al., Current opinion in neurology, 6:719-725 (2007)
[9] van de Schans, S. A. et al., Annals of oncology, 10:1-8 (2011)
[10] Kim, S. T. et al., Asia-Pacific Journal of Clinical Oncology, 7:82-87 (2011)
[11] Yao, J. C. et al., Journal of clinical oncology, 1:69-76 (2010)

[12] Nowak, A. K. et al., Cancer research, 15:4490-4496 (2003)
[13] Lesterhuis, W. J. Nature Reviews Drug discovery, 8:591-600 (2011)
[14] Baniyash, M. Seminars in Cancer Biology, 16:80-88 (2006)
[15] Shacter, E. and Weitzman, S. A. Oncology, 2:217-226 (2002)
[16] Ullman, T. A. and Itzkowitz, S. H. Gastroenterology, 6:1807-1816 (2011)
[17] Rosenberg, S. O. and Sinha, P. Journal of Immunology, 182:4499-4506 (2009)
[18] Schetter, A. J. et al., Carcinogenesis, 31:37-49 (2009)
[19] Vaknin, I. et al., Blood, 111:1437-1447 (2008)
[20] Baniyash, M. Nature reviews Immunology, 4:675-687 (2004)
[21] Ezernitchi, A. V. et al., Journal of Immunology, 177: 4763-4772 (2006)
[22] Sica, A. and Bronte, V. Journal of clinical investigation, 117:1155-1166 (2007)
[23] Ostrand-Rosenberg, S. and Sinha, P. Journal of Immunology, 182:4499-4506 (2009)
[24] Bunt, S. K. et al., Journal of immunology, 176:284-290 (2006)
[25] Serafini, P. et al., Seminars in cancer biology, 16:53-65 (2006)
[26] Gabrilovich, D. I. and Nagaraj, S. Nature Reviews Immunology, 9:162-174 (2009)
[27] Köhne, C. H. et al., Journal of cancer research and clinical oncology 138(1):65-72 (2012)
[28] Lim, R. et al., World journal of gastroenterology, 14:1879-1888 (2011)
[29] Polyzos, A. et al., Anticancer research, 5:3559-3564 (2005)
[30] Sevinc, A. et al., Asian Pacific Journal of Cancer Prevention, 4:1055-1059 (2011)
[31] Goffe, B. and Cather J. C. J Am Acad Dermatol., 49(2 Suppl):S105-11 (2003)
[32] Huye, L. E. and Dotti, G. Discov Med., 9(47):297-303 (2010)
[33] Sutlu, T. and Alici, E. J Intern Med., 266(2):154-81 (2009)
[34] Sinha, P. et al., J. Immunol., 1:181(7):4666-75 (2008)
[35] Bunt, S. K. et al. J Immunol., 1; 176(1):284-90 (2006)
[36] Bronstein-Sitton, N. Nature Immunology, 4: 957-964 (2003)
[37] De Rosa, S. et al., Current Vascular Pharmacology, 2: 259-275 (2010)
[38] Vincent, J. Cancer Research, 70: 3052-3061 (2010)
[39] Ezernitchi, A. et al., The Journal of Immunology, 177: 4763-4772 (2006)
[40] Xiong, H. Q. and Ajani J. A. Cancer and Metastasis Reviews, 23: 145-163 (2004)
[41] Kambe M. et al. The International Journal of Clinical Oncology; 10: 0272-0279 (2011)
[42] Pavillard V. et al., 15; 56(10):1315-22 (1998)

Acknowledgement of the above references herein is not to be inferred as meaning that these are in any way relevant to the patentability of the presently disclosed subject matter.

GENERAL DESCRIPTION

According to a first aspect, the invention relates to a method for determining the efficacy of a treatment with a therapeutic agent on a subject suffering from a chronic inflammatory condition, more specifically, the method of the invention provides determining whether a subject suffering from a pathologic condition that may lead to a chronic inflammation, would respond, by exhibiting a beneficial response to a treatment with a therapeutic agent. According to certain embodiments, the therapeutic agent used for treating this subject may be at least one chemotherapeutic agent, at least one biological therapy agent, at least one immunotherapeutic agent or any combination thereof. More specifically, the method of the invention may comprise the steps of:

In a first step (a), determining the level of expression of T cell antigen receptor (TCR) ζ chain (CD247) in at least one biological sample of said subject, to obtain an expression value. It should be noted that the examined sample must be obtained after initiation of the treatment.

The next step (b) involves determining if the expression value obtained in step (a) is any one of, positive, negative or equal to a predetermined standard expression value or to an expression value of CD247 in a control sample. Determination of a positive or negative expression value may be performed by comparing the expression value obtained in step (a) to a predetermined standard expression value or to an expression value of CD247 in a control sample, and calculating the differences between said expression values.

It should be noted that in certain embodiments, a positive expression value of CD247 in the tested sample indicates that the subject responds to the treatment and moreover, exhibits a beneficial response to the treatment. More specifically, a positive expression value indicates that the examined subject belongs to a pre-established population associated with a beneficial response to the specific treatment. In contrast, a negative expression value indicates that the examined subject does not respond to said treatment and more specifically, does not exhibit a beneficial response to the treatment. Thereby, the method of the invention provides determination of the efficacy of a specific treatment on a specific subject that suffers from a chronic inflammatory condition.

According to a second aspect, the invention relates to a composition comprising:

(a) detecting molecules specific for determining the level of expression of CD247 in a biological sample; and optionally (b) detecting molecules specific for determining the level of expression of at least one reference control in a biological sample.

In an optional embodiment, detecting molecules of (a) and (b) may be attached to a solid support.

A third aspect of the invention relates to a kit comprising:

(a) detecting molecules specific for determining the level of expression of CD247 in a biological sample and optionally detecting molecules specific for at least one reference control; and optionally at least one of:

(b) pre-determined calibration curve providing at least one of standard expression values of CD247 and standard values determined for the rate of change in the CD247 expression in response to said treatment;

(c) at least one control sample.

These and further aspects of the invention will become apparent by the hand of the following figures.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 1A. Graphic representation of the accumulation of Gr1+Mac1+ MDSCs at day +2 after BCG treatment in the absence or in the presence of CPT11 treatment administered i.p (left) or i.v. (right) in the spleen.

FIG. 1B. Graphic representation of the accumulation of Gr1+Mac1+ MDSCs at day +2 after BCG treatment in the absence or in the presence of CPT11 treatment administered i.p (left) or i.v. (right) in peripheral blood cells (PBLs).

FIG. 1C. Graphic representation of CD4+ gated Foxp3+ cells from the spleen of untreated, inflamed BCG-treated mice, and BCG-treated mice administered i.p. (left) or i.v. (right) with Irinotecan (CPT11). Data from three independent experiments (n=4). Statistical analyses performed using the t test indicated significant differences at 95% Cl. Means and SEM are shown. * denotes P<0.05;  denotes P<0.01; * denotes P<0.001.

Abbreviations: sp. (spleen), cont. (control), PBL (peripheral blood).

FIG. 2A-2E: The expression of CD247 in BCG mice treated with CPT11

FIG. 2A. Graphic representation of splenocytes (left) and PBLs (right) obtained from mice untreated, inflamed (BCG-treated) or inflamed that were subjected to i.p. or i.v. irinotecan treatment that were fixed, permeabilized and double stained for total expression of CD247 ($\zeta$ chain).

FIG. 2B. Graphic representation of splenocytes (left) and PBLs (right) obtained from mice untreated, inflamed (BCG-treated) or inflamed that were subjected to i.p. or i.v. irinotecan treatment that were fixed, permeabilized and double stained for total expression of CD3$\varepsilon$ chain, shown by mean fluorescence intensity (MFI). CD247 expression was measured in gated CD3+ cells. Data from three independent experiments is presented (n=4). Statistical analyses using t test indicated significant differences at 95% Cl. Means and SEM are shown. * denotes P<0.05;  denotes P<0.01; * denotes P<0.001.

FIG. 2C. Splenocytes from untreated, inflamed, and inflamed-treated i.v. with irinotecan were labeled with CFSE and activated with anti-CD3 and anti-CD28 antibodies or left non-activated. The proliferative response was assessed by monitoring cell divisions of gated CFSE-labeled Thy1.2+ (CD90+) cells. Data was calculated by percent of proliferating cells compared to steady state of non-activated of each group.

Figures 2D, 2E:
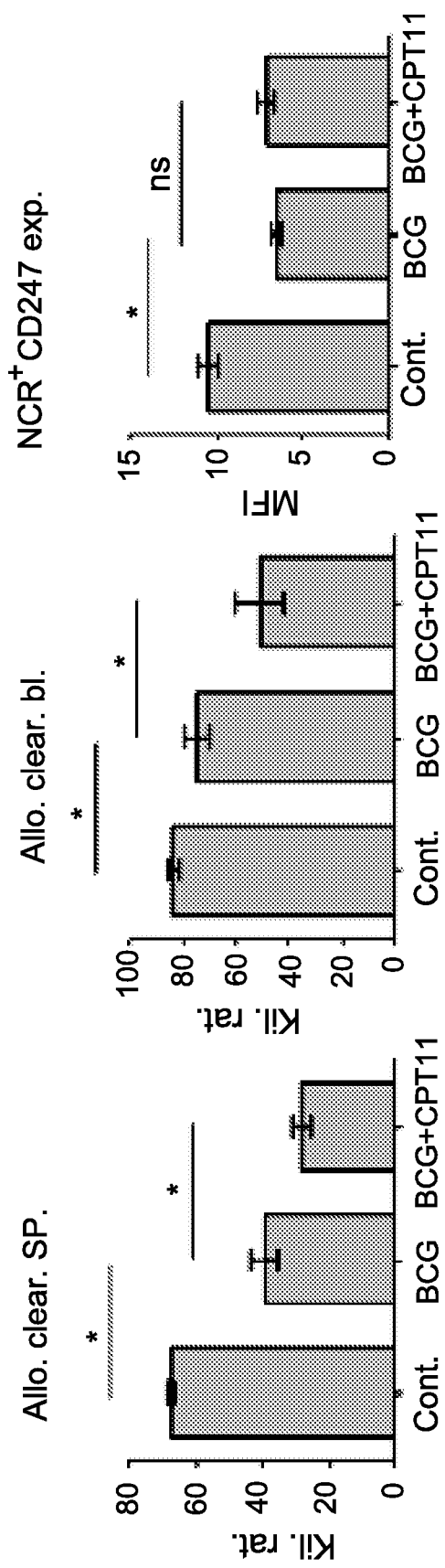

FIG. 2D. In-vivo cytotoxicity assay of CFSE labeled allogeneic (CFSElow) and syngeneic (CFSEhigh) splenic-derived cell clearance by NK cells was assessed 18-24 h following administration. A representative data of NK killing activity from three independent experiments of CFSE cell clearance within the spleens and PBLs from mice untreated, inflamed, and inflamed-treated i.v. with irinotecan, is shown.

FIG. 2E. CD247 expression was measured gating on NK (NCR1+) cells derived from the spleens of each group. Data from three independent experiments is presented (n=4). Statistical analyses using t test indicated significant differences at 95% Cl. Means and SEM are shown. *, P<0.05.

Abbreviations: sp. (spleen), cont. (control), PBL (peripheral blood).

Figure 3A:
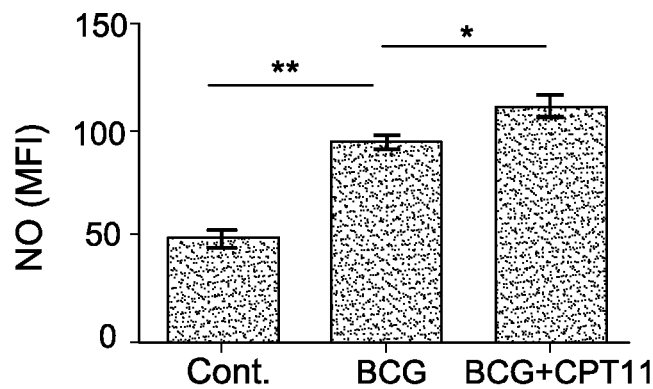
Figure 3B:
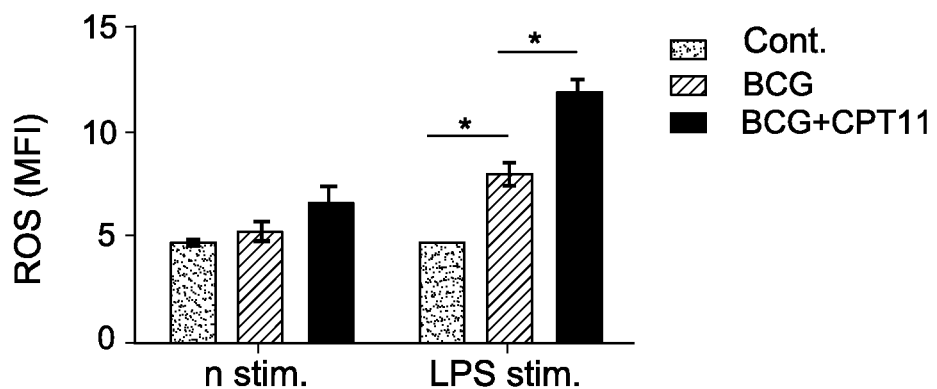

FIG. 3A-3B: Irinotecan enhances the suppressive activity of MDSCs

FIG. 3A. Splenocytes from mice untreated, inflamed, and inflamed treated i.v. with irinotecan, were prepared for intracellular nitric oxide (NO) detection, stained with non-fluorescent diaminofluorescein-2 Diacetate (DAF-2DA) and double stained for Gr1+ CD11c+ (MDSCs). NO production, gated on MDSCs, was measured as shown by MFI.

FIG. 3B. Detection of highly reactive oxygen species (hROS) secretion was performed by loading cells with APF and incubated with or without stimulator, LPS, at 37° C. and after washing, double stained for Gr1+ CD11c+ (MDSCs). hROS secretion, gated on MDSCs, was measured as shown by MFI. Data from three independent experiments (n=4) is presented. Statistical analyses using t test indicated significant differences at 95% Cl. Means and SEM are shown. *, P<0.05; ** P<0.01.

Abbreviations: sp. (spleen), cont. (control), Kil. Rat. (killing rate), Allo. Clear. (Allogeneic cell's clearance), bl. (blood), exp. (expression).

Figure 4:
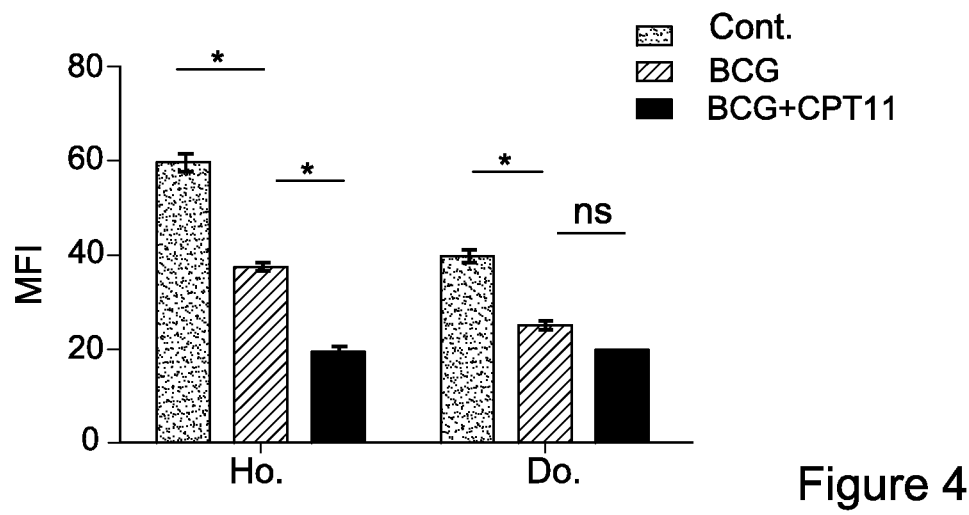

FIG. 4: Administration of irinotecan leads to dysfunction of adoptively transferred T cells CFSE-labeled splenocytes from normal mice (donor cells) were adoptively transferred into mice untreated, inflamed, and inflamed treated i.p. with irinotecan (hosts). After 24 h, splenocytes from each group were harvested and stained for CD247 expression (MFI) in CD3+ T cells within the CFSE+ (donor-cell) or CFSE− (host-cell) population. Data from three independent experiments (n=4) is presented. Statistical analyses using t test indicated significant differences at 95% Cl. Means and SEM are shown. * P<0.05. Abbreviations: Ho. (host), Do. (donor), cont. (control).

Figure 5A:
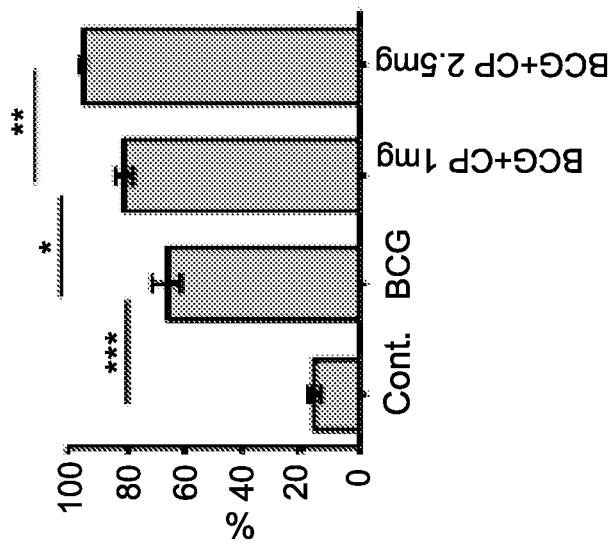
Figure 5B:
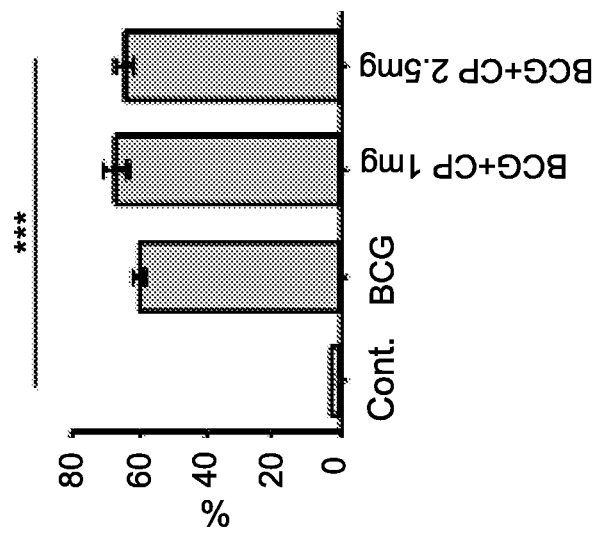
Figure 5C:
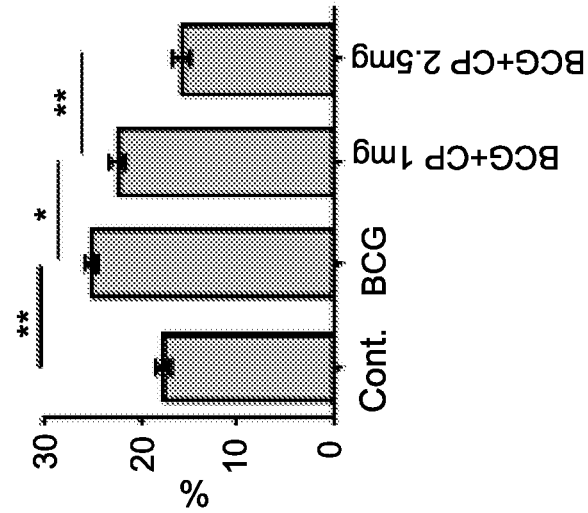

FIG. 5A-5C: Cyclophosphamide enhances chronic inflammation-dependent immunosuppression FIG. 5A. CD4+ gated Foxp3+ cells from the spleen of mice untreated, inflamed, and inflamed treated i.p. with cyclophosphamide. Data from three independent experiments (n=4).

FIG. 5B. Accumulation of MDSCs at day +2 after BCG-induced chronic inflammation in the spleen. Spleens from mice untreated, inflamed, and inflamed treated i.p. with cyclophosphamide were analyzed for MDSC levels. Data from three independent experiments (n=4).

FIG. 5C. Accumulation of MDSCs at day +2 after BCG-induced chronic inflammation in peripheral blood cells (PBLs). PBLs from mice untreated, inflamed, and inflamed treated i.p. with cyclophosphamide were analyzed for MDSC levels. Data from three independent experiments (n=4). In A-C statistical analyses using t test indicated significant differences at 95% Cl. Means and SEM are shown. *, P<0.05; , P<0.01; *, P<0.001. Abbreviations: cont. (control).

Figure 6A:
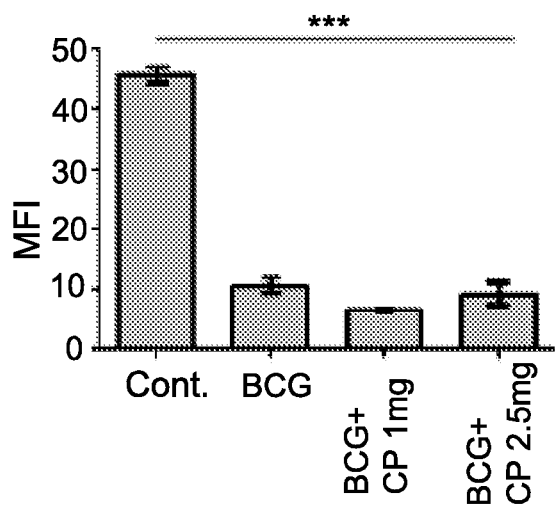
Figure 6B:
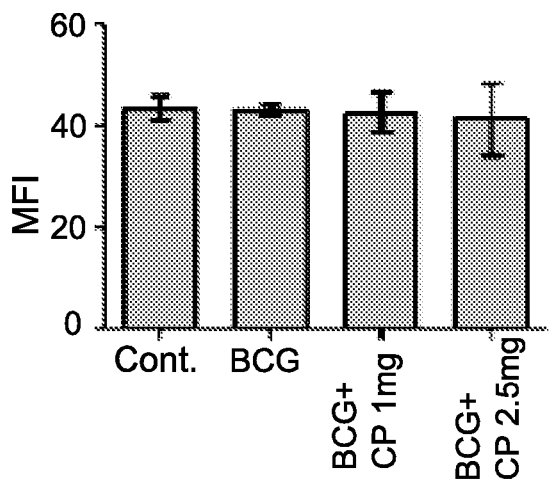
Figure 6C:
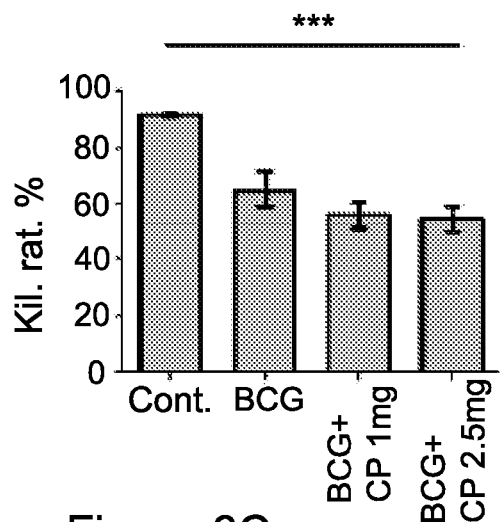
Figure 6D:
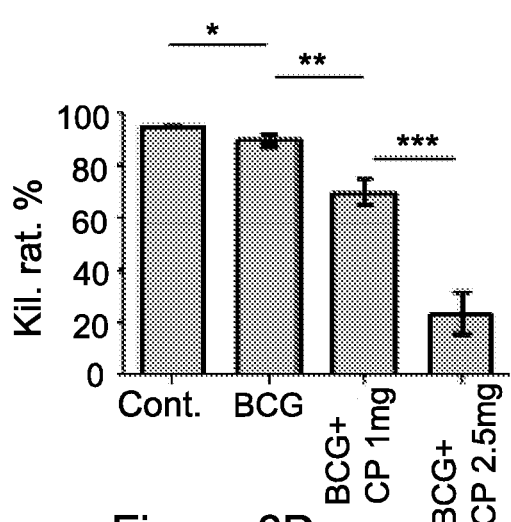

FIG. 6A-6D: Cyclophosphamide enhances T- and NK-cell dysfunction under chronic inflammation Splenocytes and PBLs from mice untreated, inflamed, and inflamed treated i.p. with cyclophosphamide were fixed, permeabilized and double stained for total expression of the CD247 and CD3$\varepsilon$. FIG. 6A. CD247 expression was measured in gated CD3+ cells. Data from three independent experiments (n=4) is presented. Statistical analyses using t test indicated significant differences at 95% Cl. Means and SEM are shown. ***, P<0.001. FIG. 6B. CD3$\varepsilon$ expression levels are shown by mean fluorescence intensity (MFI). Statistical analyses using t test indicated significant differences at 95% Cl. Means and SEM are shown. FIG. 6C, FIG. 6D. In-vivo cytotoxicity assay of CFSE labeled allogeneic (CFSElow) and syngeneic (CFSEhigh) splenic-derived cells clearance by NK cells, assessed 18-24 h following administration of cells. The data of NK killing activity from three independent experiments of CFSE cell clearance within the spleens (FIG. 6C) and PBLs (FIG. 6D) from mice untreated, inflamed, and inflamed treated i.p. with cyclophosphamide, is shown. Data of three independent experiments (n=4). Statistical analyses using t test indicated significant differences at 95% Cl. Means and SEM are shown. *, P<0.05; , P<0.01; *, P<0.001. Abbreviations: cont. (control), Kil. Rat. (killing rate).

Figure 7A:
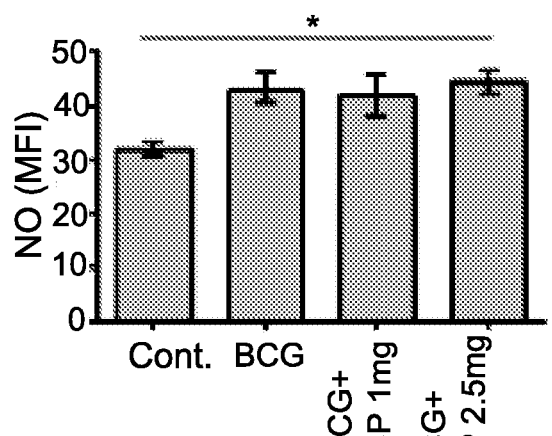
Figure 7B:
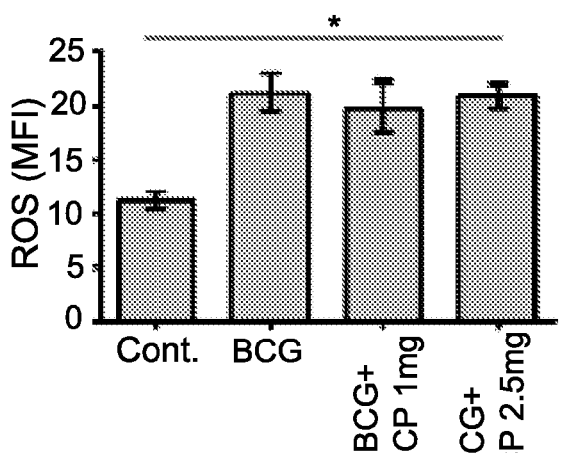
Figure 9A:
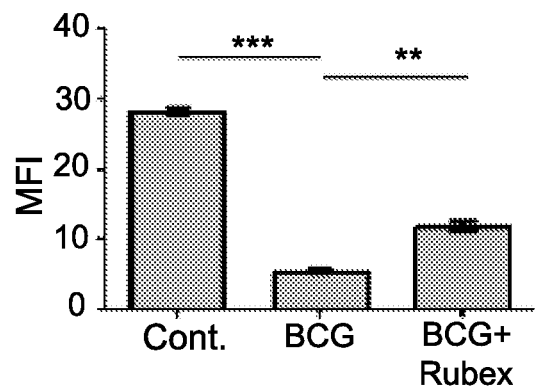
Figure 9B:
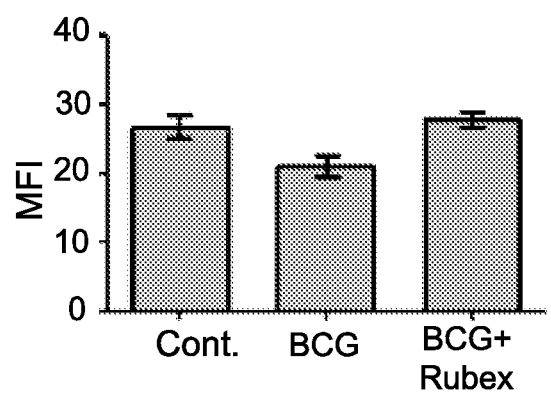
Figure 9C:
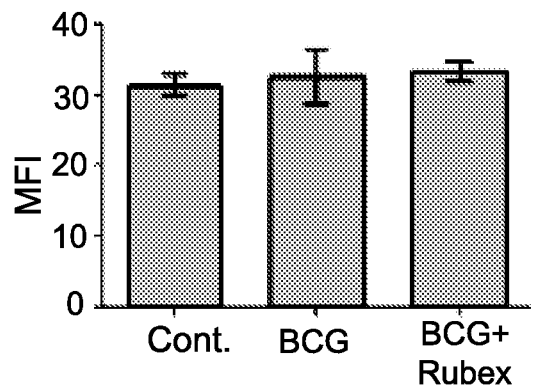
Figure 9D:
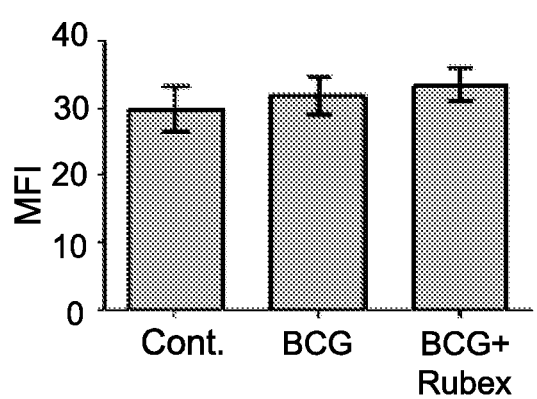

FIG. 7A-7B: MDSCs suppressive activity is maintained under cyclophosphamide treatment FIG. 7A. Splenocytes from mice untreated, inflamed, and inflamed treated i.p. with cyclophosphamide were prepared for intracellular nitric oxide (NO) detection, stained with non-fluorescent diaminofluorescein-2 Diacetate (DAF-2DA) and double stained for Gr1+ CD11c+ (MDSCs). NO production, gated on MDSCs, was measured as shown by MFI.

FIG. 7B. Detection of highly reactive oxygen species (hROS) secretion was performed by loading cells with APF and incubated with or without stimulation of added LPS at 37° C. and after washing, double stained for Gr1+ CD11c+ (MDSCs). hROS secretion, gated on MDSCs, was measured as shown by MFI. Data from three independent experiments (n=4) is presented. Statistical analyses using t test indicated significant differences at 95% Cl. Means and SEM are shown. *, P<0.05. Abbreviations: cont. (control).

FIG. 8A-8C: Doxorubicin (Rubex) reduces the immunosuppressive effect of a chronic inflammatory response FIGS. 8A and 8B Accumulation of MDSCs at day +2 after the course of BCG treatment induces chronic inflammation in the spleen (FIG. 8A) and peripheral blood cells (PBLs) (FIG. 8B). Treatment i.p. of inflamed mice with doxorubicin reduced MDSC levels in the spleen (FIG. 8A) and PBLs (FIG. 8B).

FIG. 8C. CD4+ gated Foxp3+ cells from the spleen of mice non-inflamed, inflamed and inflamed treated i.p. with doxorubicin revealed no change in the level of Foxp3+ cells. Data from three independent experiments (n=4) is presented. Statistical analyses using t test indicated significant differences at 95% Cl. Means and SEM are shown. *, P<0.05; , P<0.01; *, P<0.001. Abbreviations: sp. (spleen), cont. (control), PBL. (peripheral blood), exp. (expression).

FIG. 9A-9D: Doxorubicin restores CD247 expression in T- and NK-cells under chronic inflammation Splenocytes (FIGS. 9A, 9C) and PBLs (FIGS. 9B, 9D) from mice non-inflamed, inflamed, and inflamed treated i.p. with doxorubicin were fixed, permeabilized and double stained for total expression of the CD247 (FIGS. 9A, 9B) or CD3_ (FIGS. 9C, 9D), as shown by mean fluorescence intensity (MFI). CD247 expression was measured in gated CD3+ cells. Data from three independent experiments (n=4) is presented. Statistical analyses using t test indicated significant differences at 95% Cl. Means and SEM are shown. *, P<0.05; , P<0.01; *, P<0.001. Abbreviations: sp. (spleen), cont. (control), PBL. (peripheral blood).

FIG. 10A-10C: Busulfan reduces the chronic inflammatory response Accumulation of MDSCs observed at day +2 after BCG-induced chronic inflammation, in the spleen (FIG. 10A), and peripheral blood cells (PBLs) (FIG. 10B) is reduced upon i.p. administration of busulfan (FIG. 10A, 10B).

FIG. 10C. CD4+ gated Foxp3+ cells from the spleen of mice non-inflamed, inflamed, and inflamed-treated i.p. with doxorubicin. Data from three independent experiments (n=4) is resented. Statistical analyses using t test indicated significant differences at 95% Cl. Means and SEM are shown. *, P<0.05; , P<0.01; *, P<0.001. Abbreviations: sp. (spleen), cont. (control), PBL. (peripheral blood).

FIG. 11A-11B: Busulfan restores CD247 expression under chronic inflammation Splenocytes from mice non-inflamed, inflamed, and inflamed-treated i.p. with busulfan were fixed, permeabilized and double stained for total expression of the (CD247) (FIG. 11A) or CD3 (FIG. 11B) chains, as shown by mean fluorescence intensity (MFI). CD247 expression was measured in gated CD3+ cells. Data from three independent experiments (n=4) is presented. Statistical analyses using t test indicated significant differences at 95% Cl. Means and SEM are shown. *, P<0.05; **, P<0.01. Abbreviations: cont. (control).

FIG. 12A-12C: 5-fluorouracil (5-FU) neutralizes chronic inflammation induced immunosuppression Accumulation of MDSCs observed at day +2 after BCG-induced chronic inflammation, in the spleen (FIG. 12A) and peripheral blood cells (PBLs) (FIG. 12B) is reduced upon i.p. administration of 5FU. (FIG. 12C) CD4+ gated Foxp3+ cells from the spleen of mice non-inflamed, inflamed, and inflamed-treated i.p. with 5FU. Data from three independent experiments (n=4) is presented. Statistical analyses using t test indicated significant differences at 95% Cl. Means and SEM are shown. *, P<0.05; , P<0.01; *, P<0.001. Abbreviations: sp. (spleen), cont. (control), PBL. (peripheral blood).

FIG. 13A-13E: 5-FU restores T- and NK-cell function under chronic inflammation

FIG. 13A-13B. Splenocytes and PBLs from non-inflamed, inflamed, and inflamed mice treated i.p. with 5-FU were fixed, permeabilized and double stained for total expression of the (CD247, FIG. 13A) or (FIG. 13B) CD3 chains, as shown by mean fluorescence intensity (MFI). CD247 expression was measured in gated CD3+ cells. Data from three independent experiments (n=4) is presented. Statistical analyses using t test indicated significant differences at 95% Cl. Means and SEM are shown. *, P<0.05; , P<0.01; *, P<0.001.

FIG. 13C. CD247 expression was measured on gated NK (NCR1+) cells derived from spleens of each group. Data from three independent experiments (n=4) is presented.

FIG. 13D, 13E. In-vivo NK cell cytotoxicity assay assessed by clearance of CFSE labeled allogeneic (CFSElow) and syngeneic (CFSEhigh) splenic-derived cells, 18-24 h following their administration. A representative data of NK killing activity from three independent experiments of CFSE cell clearance within the spleens (FIG. 13D) and PBLs (FIG. 13E) from non-inflamed, inflamed, and inflamed mice treated i.p. with 5-FU, is shown. Statistical analyses using t test indicated significant differences at 95% Cl. Means and SEM are shown. *, P<0.05. Abbreviations: cont. (control), Kil. Rat (killing rate).

FIG. 14: Administration of 5-FU leads to a restoration of CD247 expression of adoptively transferred T cells CFSE-labeled splenocytes from normal mice (donor cells) were adoptively transferred into non-inflamed, inflamed, and inflamed mice treated i.p. with 5-FU (hosts). After 24 h, splenocytes from each group were harvested and stained for CD247 expression (MFI) in CD3+ T cells within the CFSE+ (donor-cell) or CFSE− (host-cell) population. Data from three independent experiments (n=4) is presented. Statistical analyses using t test indicated significant differences at 95% Cl. Means and SEM are shown. *, P<0.05. Abbreviations: Ho. (host), Do. (donor), cont. (control).

FIG. 15A-15H: Administration of etanercept increases MDCS differentiation and reduces immunosuppression FIG. 15A. A schematic presentation of the mouse model used. WT-mice were injected daily with etanercept from 1 day prior to the second BCG injection until 1 day before mice were sacrificed. Etanercept-treated mice were compared with non-inflamed and inflamed WT- and KO-mice.

FIG. 15B. Spleen weight (left) and size (right) in etanercept-treated and untreated mice (n=7) was evaluated 2 days following the third BCG injection. *P<0.003, **P<0.002 (t-test). Data are from two independent experiments (mean and s.d.).

FIG. 15C Accumulation of MDSCs 2 days after the last BCG treatment in the spleen, of etanercept-treated and untreated mice (n=7). *P<0.02, **P<0.003 (t-test). Data are representative of two independent experiments (error bars, s.d.). (D,E) Levels of CD11c+ (FIG. 15D.) and F4/80+ (FIG. 15E.) cells in spleens of etanercept-treated and untreated mice (n=7); plots are gated on CD11b+ cells. *P<0.008, **P<0.004 (t-test). Data are representative of two independent experiments (error bars, s.d.). (FIG. 15F, 15G) CFSE-labeled splenocytes from normal WT-mice (donor cells) were adoptively transferred into etanercept-treated and untreated mice (hosts). After 24 h, splenocytes were harvested and stained for CD247 expression (MFI) in CD3+ T (FIG. 15F) and NCR1++NK (G) cells within the CFSE+ (donor-cell) or CFSE− (host-cell) population. *P<0.012, **P<0.009 (t-test). Data are representative of two independent experiments (error bars, s.d. n=7 per group). (FIG. 15H) In-vivo NK cytotoxicity assay was performed in etanercept-treated or untreated mice, as described in FIG. 2E. Allogeneic cell clearance in spleen and blood from two independent experiments are presented (mean and s.d. n=7 per group). *P<0.038, **P<0.006 (t-test). Abbreviations: Ho. (host), ce. (cells), Do. (donor), har. (harvest), D. Etan. Admi. (daily Etanercept administration), trea. (treatment), sp. (spleen), we. (weight), WT (wild type), KO (knock-out), Bl. (blood).

FIG. 16A-16D: Selected chemotherapeutics and their in-vivo effect on MDSCs

Figure 16A:
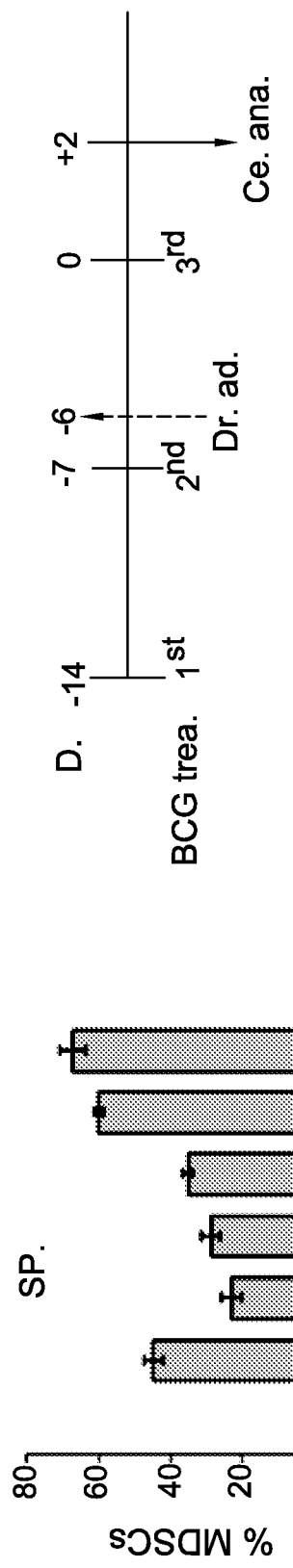
Figure 16B:
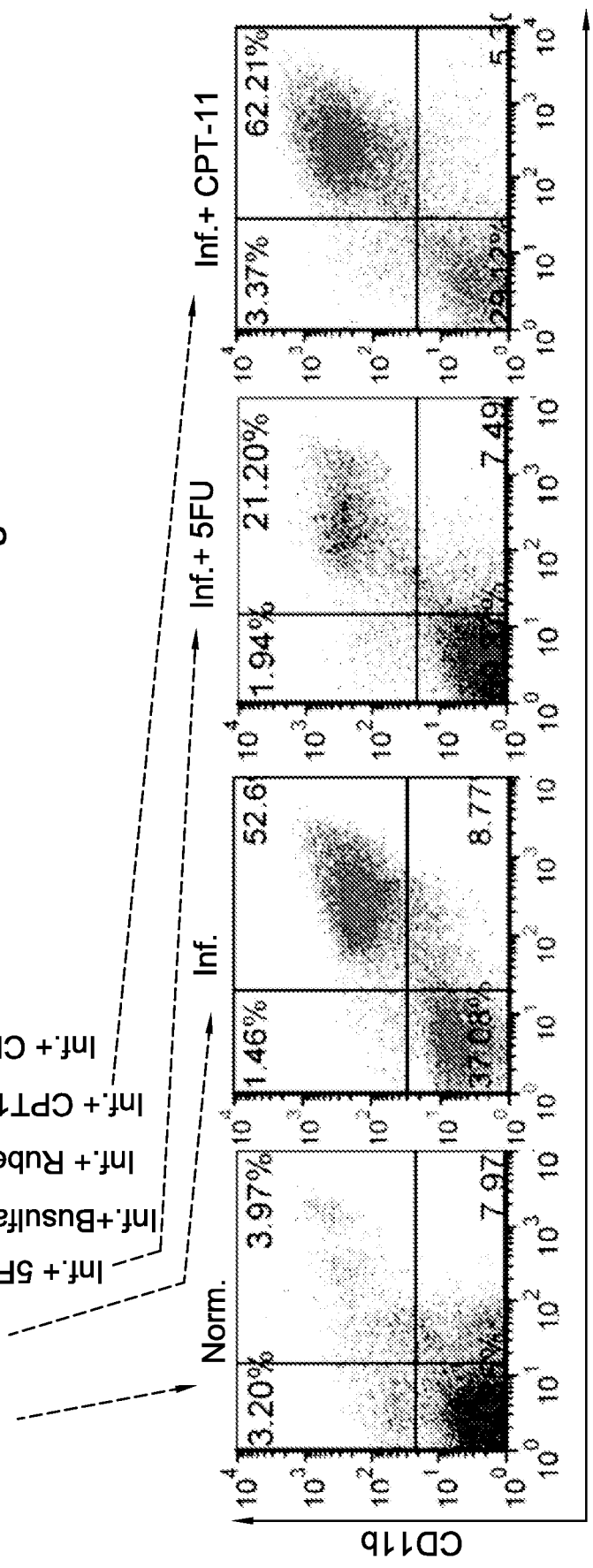
Figure 16C:
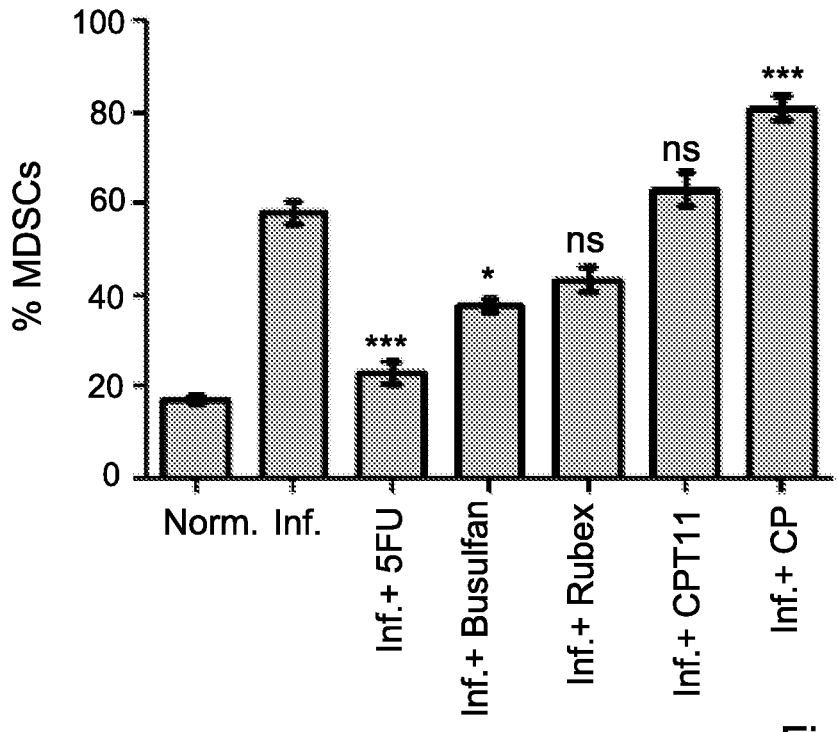
Figure 16D:
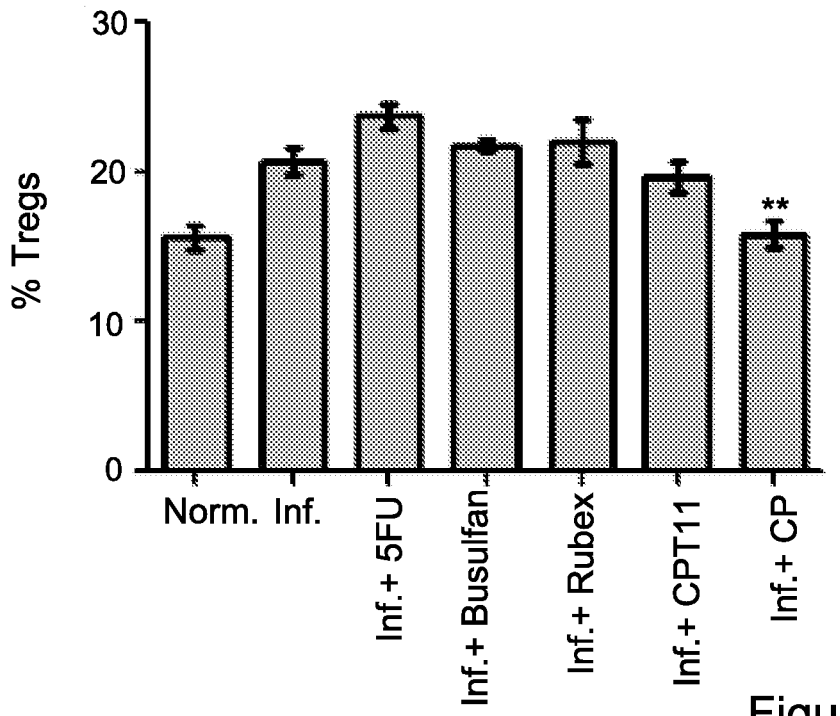

FIG. 16A Schematic representation of the mouse model for chronic inflammation. FIG. 16B, 16C. Following the chemotherapy treatments (saline, control mice; Rubex, Doxorubicin; Busulfan; 5-FU, 5-fluorouracil, CPT-11, Irinotecan; CP, Cyclophosphamide), (FIG. 16B, top) spleens (bottom; representative 5-FU and CPT-11 plots) and (FIG. 16C) peripheral blood cells (PBLs) were isolated and MDSCs ($Gr1^+CD11b^+$) accumulation was revealed by flow cytometry analysis. Graphs represent the percent of MDSCs presented within the spleen and PBLs. (FIG. 16D) Tregs derived from the spleens of each group were measured after fixation/permeabilization and double staining for $CD4^+$ $Foxp3^+$. Data from three independent experiments (n=4) is presented. Statistical analyses using t test indicated significant differences at 95%. Means and SEM are shown. *, P<0.05; , P<0.01; *, P<0.001. Abbreviations: trea. (treatment), Dr. (drug), ad (administration), ce. Ana. (cell analysis), Norm. (normal), Inf. (inflamed).

Figure 17A:
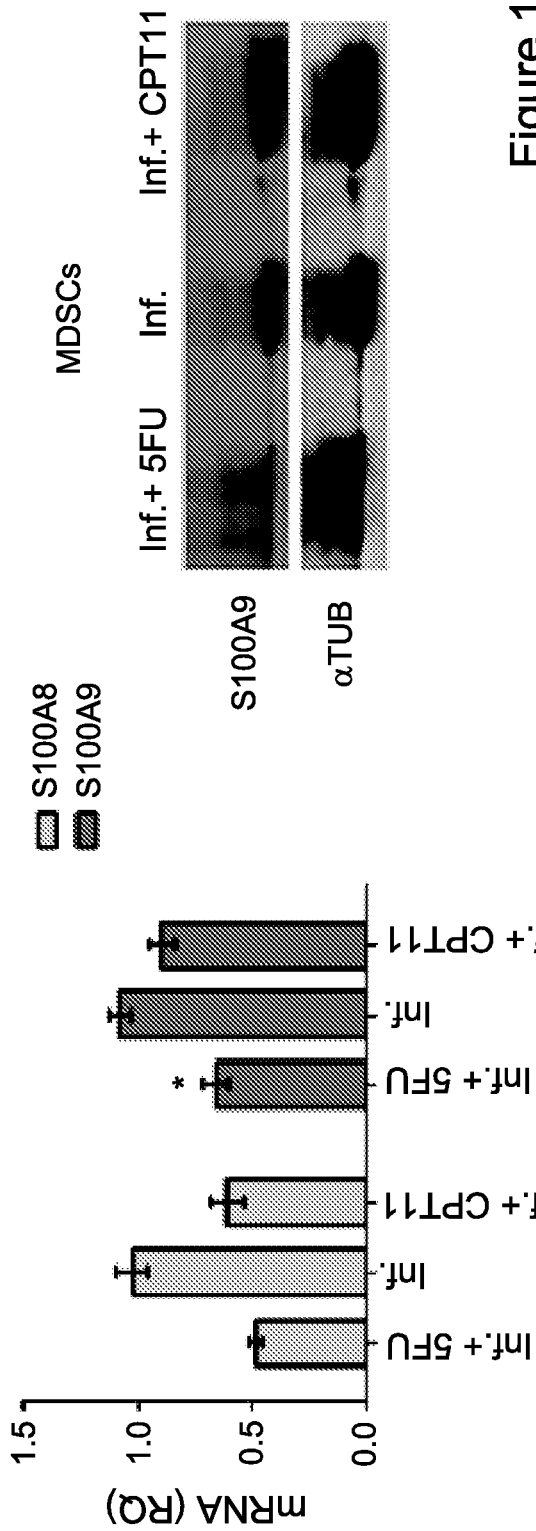
Figure 17B:
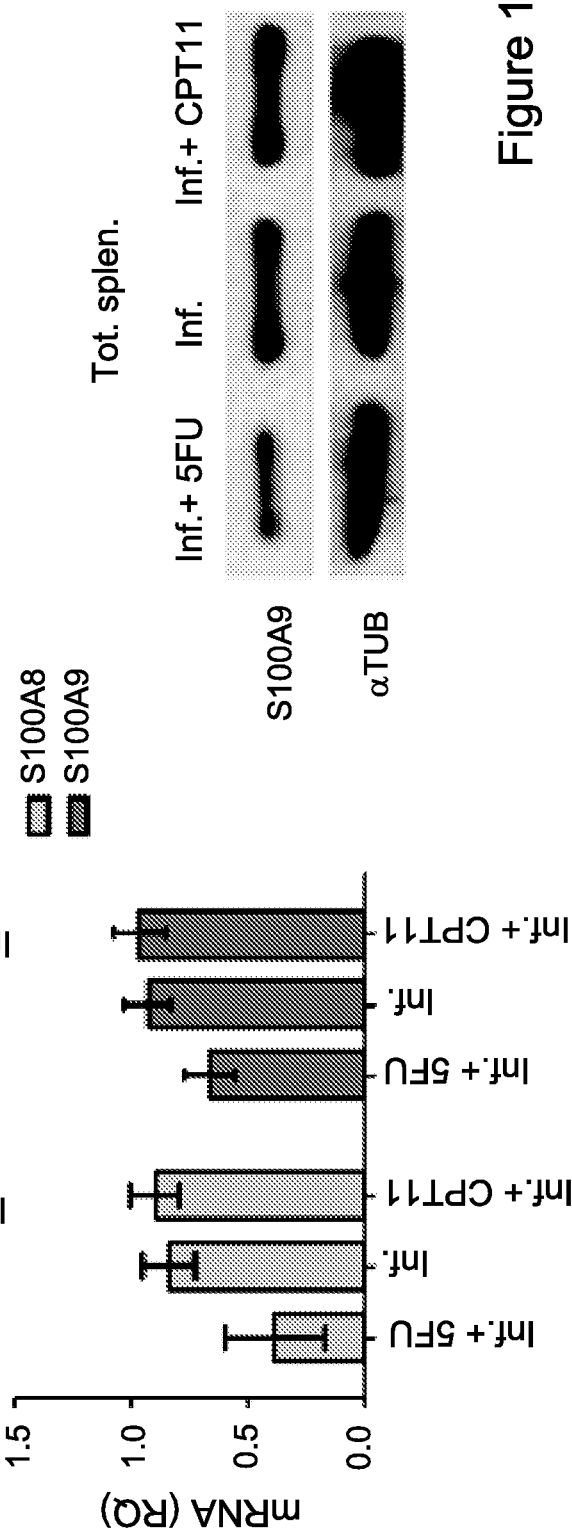

FIG. 17A-17F: 5-FU and CPT-11 monotherapies display opposite effect on MDSC suppressive activity FIG. 17A. Purified MDSCs from spleens (n=4); and FIG. 17B. A total spleen population was used to analyze mRNA levels of S100A8/9 (left), and to perform immunoblotting of S100A9 (right) following the course of chronic inflammation alone, chronically inflamed mice treated with 5-FU or CPT11 (n=4), α-Tubulin levels served as a control.

FIG. 17C. Real Time PCR analyses were performed to check the levels of inflammatory cytokines (TNFα, IL-6, IFNγ) following administration of 5-FU or CPT11, relative to the expression in inflamed mice with no chemotherapy treatment (set as 1). Statistical analyses using t test indicated significant differences at 95%. *, P<0.05; , P<0.01; *, P<0.001. FIG. 17D. Splenocytes isolated from inflamed mice, or inflamed mice treated with 5-FU or CPT11 (n=3) were analyzed for nitric oxide (NO); and FIG. 17E. Reactive oxygen species (ROS) production, both by flow cytometry analysis gaiting on the MDSCs ($Gr1^+CD11b^+$) population. Histograms represent production levels, as shown by mean fluorescence intensity (MFI). Data from three independent experiments (n=4) are presented. Statistical analyses using t test indicate significant differences at 95%. Means and SEM are shown. *, P<0.05; **, P<0.01.

FIG. 17F. Splenic MDSCs from each group were analyzed for the expression percentage of cleaved caspase-3, revealed by flow cytometry analysis gating on MDSC ($Gr1+CD11b^+$) populations. Statistical analyses using t test indicated significant differences at 95%. Means and SEM are shown. *, P<0.05; **, P<0.01. Abbreviations: Inf. (inflamed), Tot. sp. (total spleen), sp (spleen), g. (gated), Norm. (normal).

Figure 18A:
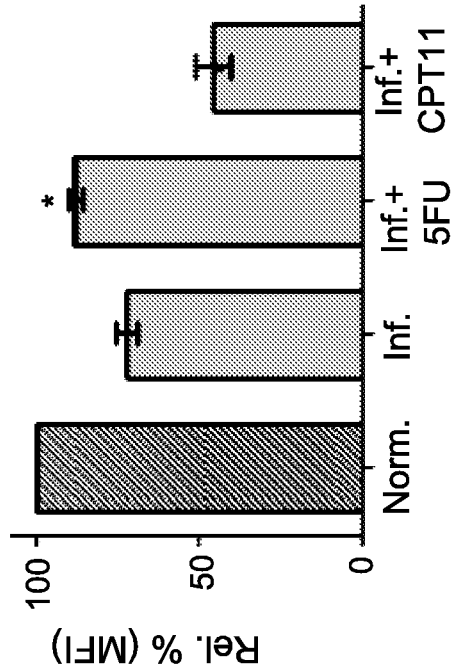
Figure 18B:
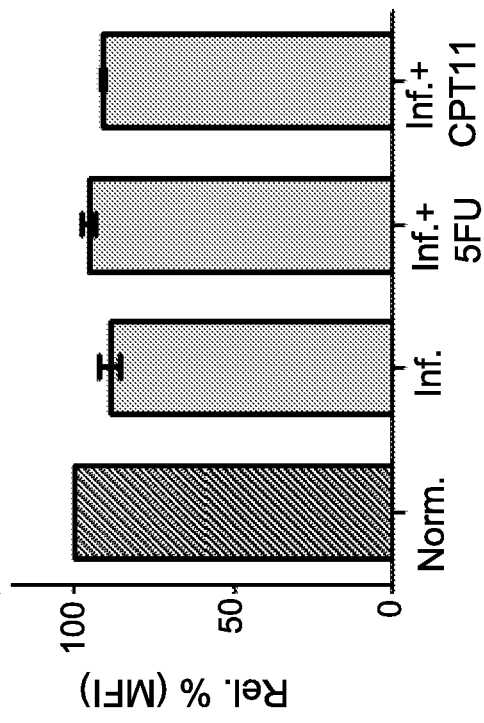
Figure 18C:
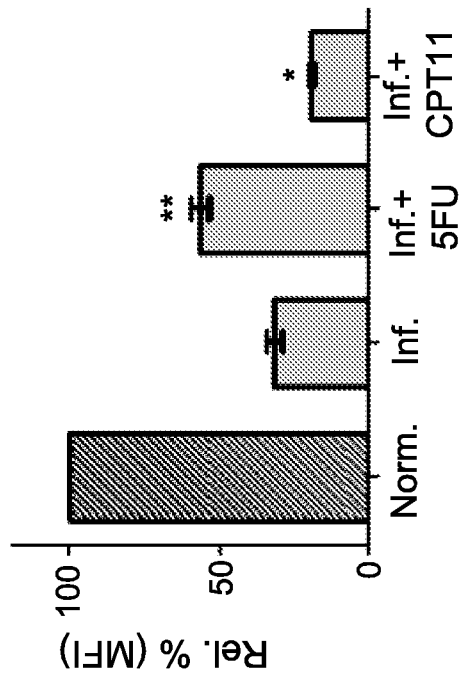
Figure 18D:
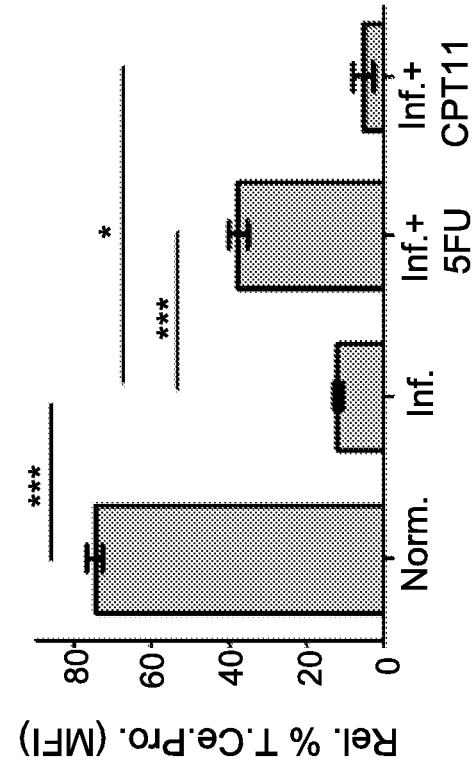

FIG. 18A-18I: Differential effects of 5-FU and CPT-11 monotherapies on T-cell activity FIG. 18A-18E. Splenocytes and PBLs from mice untreated (naïve), inflamed, or inflamed and treated with 5-FU or CPT-11 were fixed, permeabilized, and double stained for the expression of CD247 (ζ-chain) (FIGS. 18A, 18B) and CD3ε-chain (FIGS. 18D, 18E), as shown by mean fluorescence intensity (MFI), measured in gated $CD3^+$ cells. FIG. 18C: Splenocytes from mice, naïve, inflamed and inflamed treated with 5-FU or CPT-11, were labeled with CFSE and activated with anti-CD3 and anti-CD28 antibodies or left non-activated. The proliferative response was assessed by monitoring cell divisions of gated CFSE-labeled Thy1.2+ (CD90+) T-cells. The percent of proliferating cells was calculated and compared to steady state levels of non-activated cells per each group. Data from three independent experiments is presented (n=3). Statistical analyses using t test indicated significant differences at 95%. Means and SEM are shown. *, P<0.05; **, P<0.01. FIG. 18F-18I. For the detection of myeloid differentiation state, splenocytes from each group were stained for (18F) $DC11b^+CD11c^+$ cells (representing DCs), (18G) $DC11b^+F4/80^+$ cells (representing monocytes), (18H) $CD11c^+MHCII^+CD80^+$ cells (representing fully differentiated Dcs as antigen presenting cells) and (18I) $F4/80^+MHCII^+CD80^+$ cells (representing fully differentiated Dcs as antigen presenting cells). Data from three independent experiments (n=4) is presented. Statistical analyses using t test indicated significant differences at 95%. Means and SEM are shown. *, P<0.05; , P<0.01; *, P<0.001. Abbreviations: Nor. (normal), Rel. (relative), Inf. (inflamed), ce. Pro. (cell proliferation)

Figure 19A:
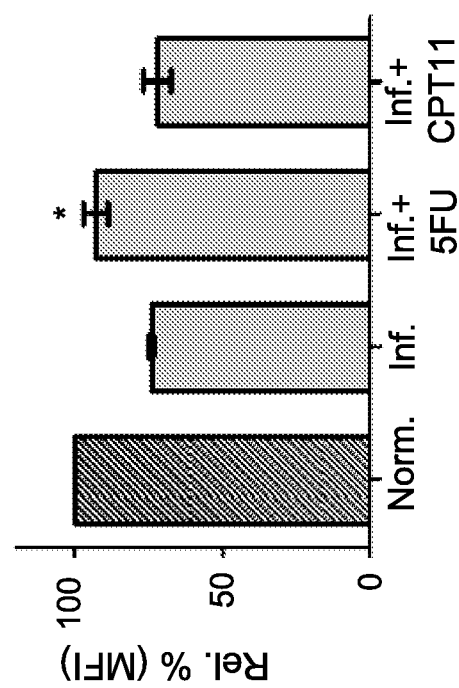
Figure 19C:
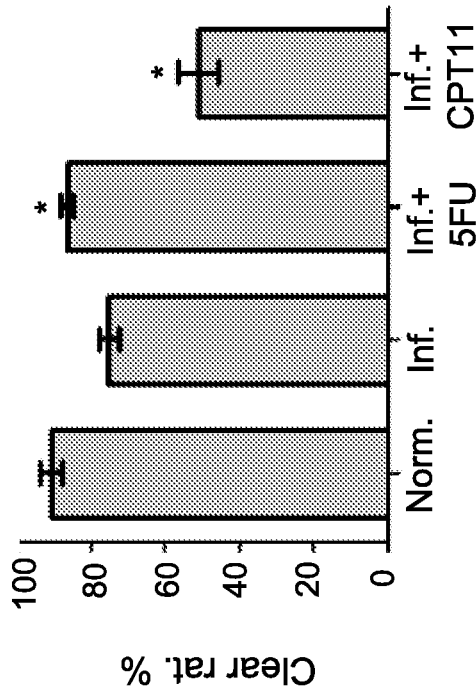
Figure 18I:
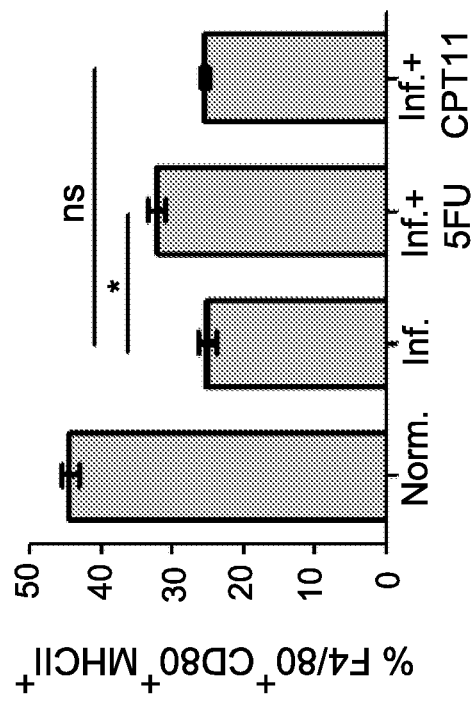
Figure 19B:
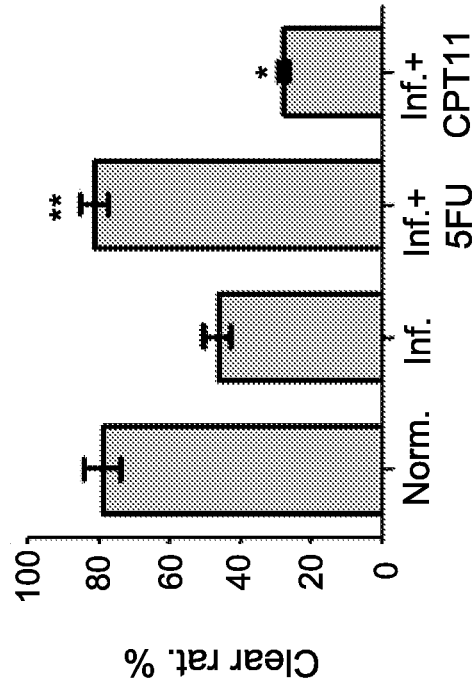

FIG. 19A-19C: Differential effects of 5-FU and CPT-11 monotherapies on NK-cell activity FIG. 1A. CD247 expression levels, as shown by MFI, were measured in gated NK (NCR1+) cells derived from the spleens of each group. Data from three independent experiments is presented (n=4). Statistical analyses using t test indicated significant differences at 95%. Means and SEM are shown. *, P<0.05.

FIGS. 19B, 19C. In-vivo cytotoxicity assay of CFSE-labeled allogeneic ($CFSE^{low}$) and syngeneic ($CFSE^{high}$) splenic-derived cell clearance by NK-cells was assessed 18-24 h following administration. Representative data of NK killing activity from three independent experiments of CFSE cell clearance within the (b) spleens and (c) PBLs from naïve, inflamed, and inflamed-5-FU or CPT-11 treated mice, is shown. Abbreviations: Nor. (normal), clear rat. (clearance rate), Inf. (inflamed), FIG. 20A-20J: Different doses of combined 5-FU/CPT-11 therapy decreases MDSC levels but have diverse effects on their suppressive activity Following combined chemotherapy treatment of 5-FU and CPT-11 [high dose-50 mg/kg of each drug; FIG. 20A-20F or low dose-25 mg/kg of each drug; FIG. 20G-20J] (control groups are naïve and BCG-inflamed mice), (FIG. 20A, 20G) spleens were isolated and analyzed for MDSC levels by flow cytometry. Statistical analyses using t test indicated significant differences at 95%. Means and SEM are shown. *, P<0.05.

Figure 20C:
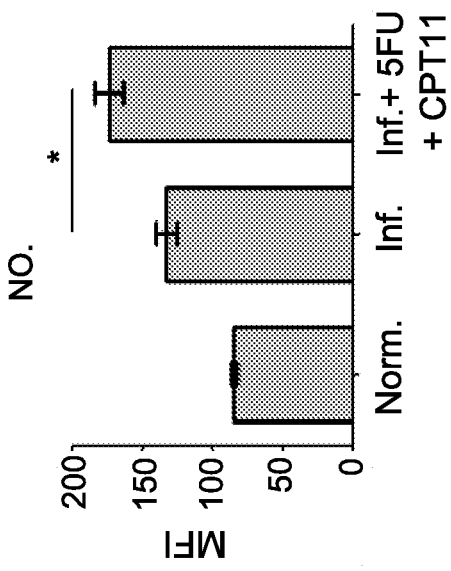
Figure 20B:
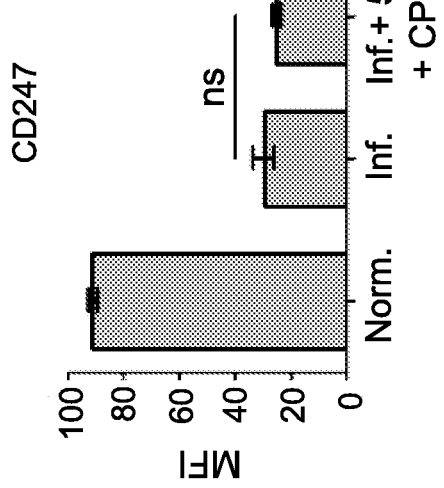
Figure 20A:
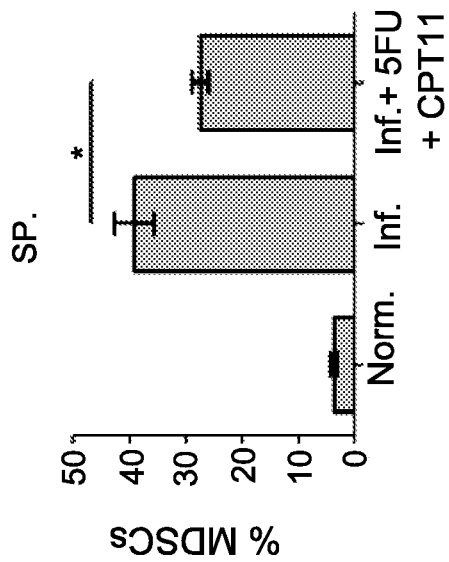
Figure 20F:
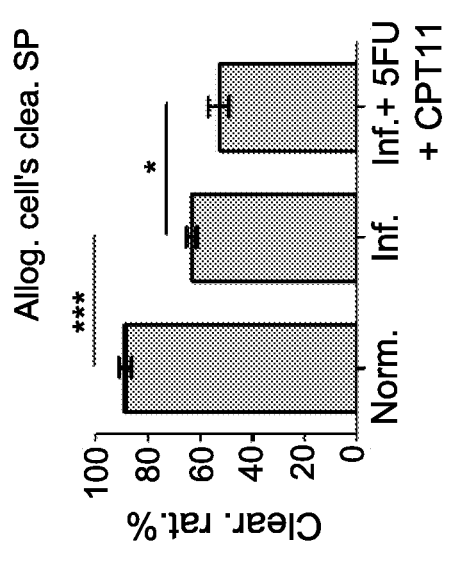
Figure 20E:
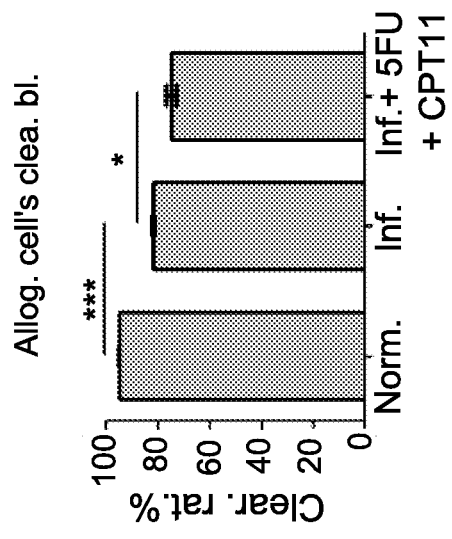
Figure 20D:
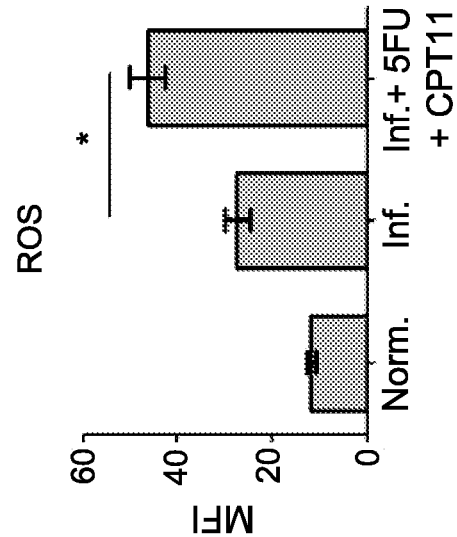
Figures 20G, 20H, 20I, 20J:
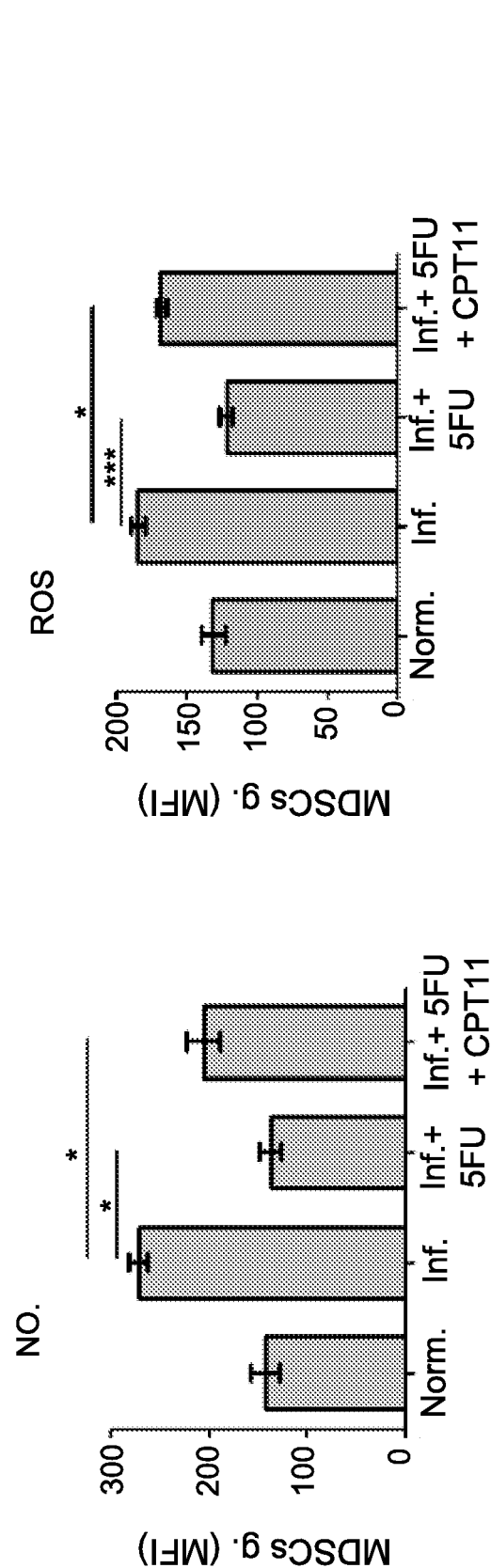

FIG. 20B, 20H) CD247 expression within the spleen, as shown by MFI, was measured gating on $CD3^+$ cells. Data from three independent experiments (n=3) is presented. Statistical analyses using t test was performed; non-significant (ns), **, P<0.01; FIG. 20C,D,I,J. For the detection of MDSCs' suppressive activity NO (FIG. 20C,I) and hROS (FIG. 20D, 20J) levels were measured as in FIG. 7, indicating that MDSCs under the combined treatment display an enhanced suppressive activity as compared to the inflamed untreated mice. Data from three independent experiments (n=4) is presented. Statistical analyses using t test indicated significant differences at 95%. Means and SEM are shown. *, P<0.05. FIG. 20E, FIG. 20F, In-vivo NK cell cytotoxicity assay assessed by clearance of CFSE labeled allogeneic (CFSElow) and syngeneic (CFSEhigh) splenic-derived cells, 18-24 h following their administration. A representative data of NK killing activity from three independent experiments of CFSE cell clearance within the spleens (FIG. 20F) and PBLs (FIG. 20E) from non-inflamed, inflamed, and inflamed mice treated i.p. with a combination of 5-FU and CPT11, is shown. Statistical analyses using t test indicated significant differences at 95% CI. Means and SEM are shown. *, P<0.05; ***, P<0.001. Abbreviations: Nor. (normal), clear rat. (clearance rate), Inf. (inflamed), Allog. Cells clea. Bl. (allogenic cells clearance in blood), SP. (spleen).

Figure 21C:
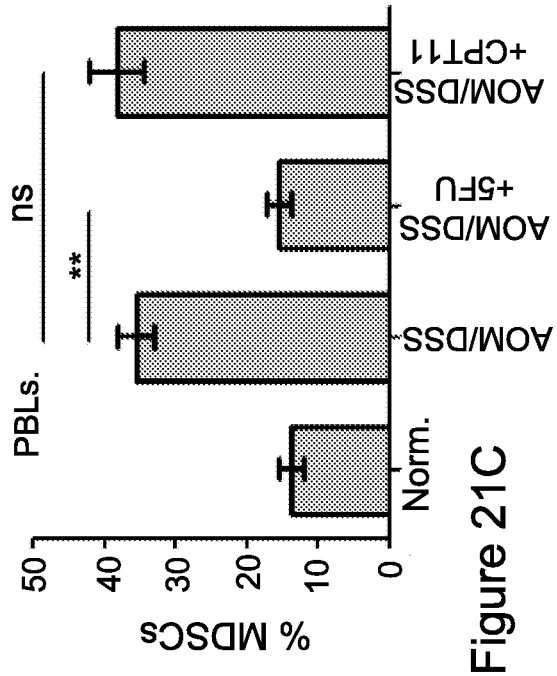
Figure 21D:
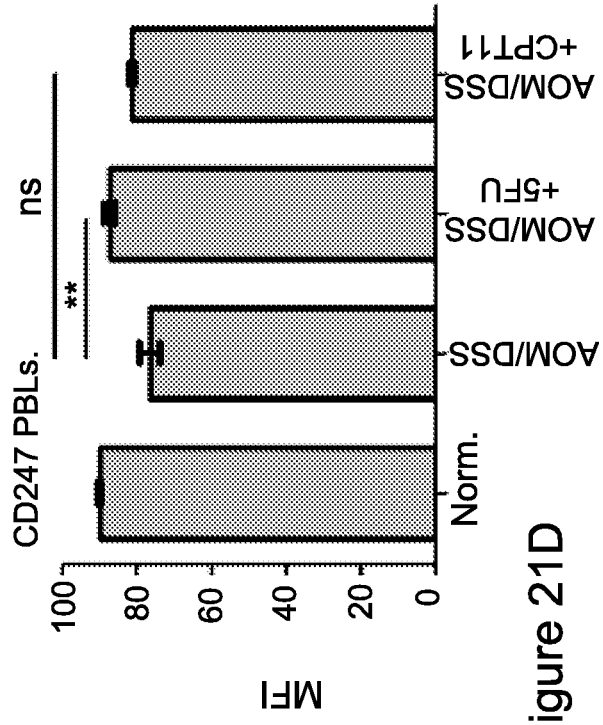
Figure 21A:
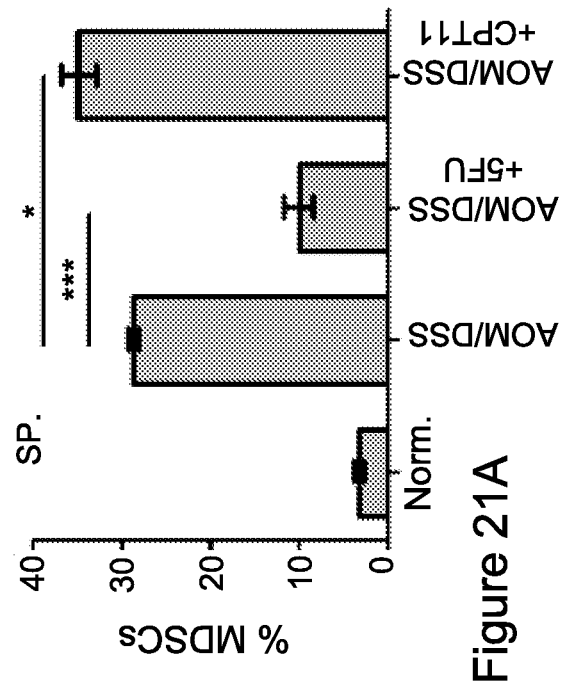
Figure 21B:
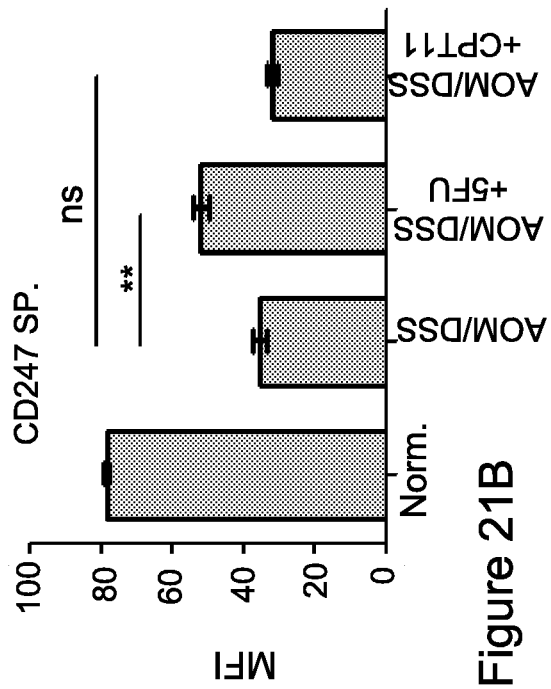

FIG. 21A-21D: A mouse model for colorectal cancer (CRC) associated with chronic inflammation and the effect of mono-chemotherapies The mouse model for CRC was used as described in Experimental procedures. DSS treatment mice were randomized into three groups (n=10 mice) as follows: CRC control group, CRC and 5-FU i.p inoculated group and CRC and CPT-11 i.p inoculated group. Mice were sacrificed at week +11, three weeks after the second DSS treatment. Following the chemotherapy treatments spleens and peripheral blood cells (PBLs) were isolated and (FIG. 21A, 21C) MDSCs (Gr1+CD11b+) accumulation was revealed by flow cytometry analysis. Graphs represent the percent of MDSCs presented within the spleen (FIG. 21A) and PBLs (FIG. 21C). Data from three independent experiments (n=3) is presented. Statistical analyses using t test indicated significant differences at 95%. Means and SEM are shown. *, P<0.05; , P<0.01; *, P<0.001. FIGS. 21B, 21D. Splenocytes (FIG. 21B) and PBLs (FIG. 21D) from mice naïve, CRC-bearing, or CRC-bearing and treated with 5-FU or CPT-11 were fixed, permeabilized, and double stained for the expression of CD247 (ζ-chain). Samples were subjected to FACS analysis. Data from three independent experiments (n=3) is presented. Statistical analyses using t test indicated significant differences at 95%. Means and SEM are shown. **, P<0.01. Abbreviations: Norm. (normal).

FIG. 22A-22D: Combined chemotherapies on the immune status of CRC-bearing mice

Figure 22A:
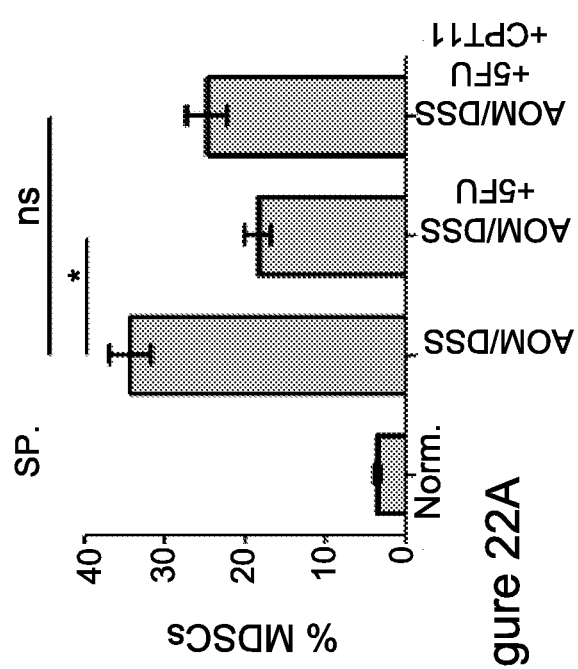
Figure 22B:
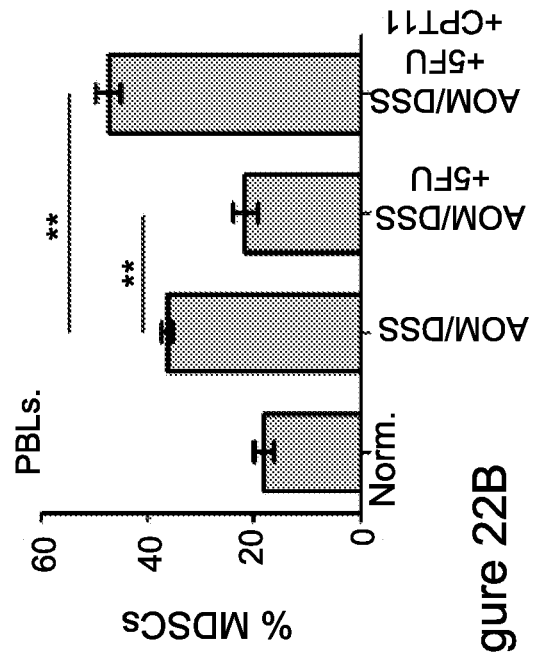

FIG. 22A, 22B. CRC-bearing mice were treated with 5-FU or with 5FU and CPT-11 as indicated in FIG. 21. Following treatment, mice were analyzed for the effect of the chemotherapeutic treatment on MDSCs as described in FIG. 21A, 21C.

Figure 22C:
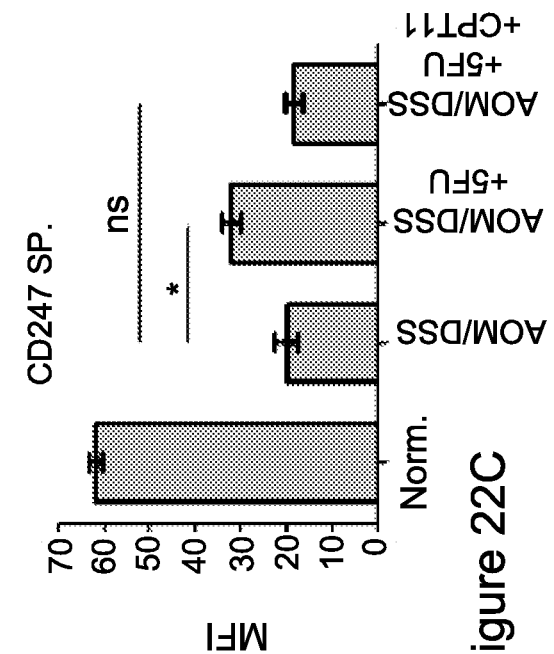
Figure 22D:
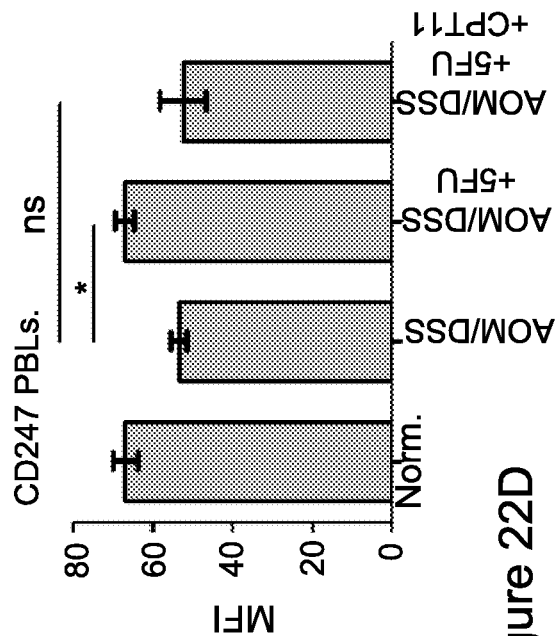

FIG. 22C, 22D. Splenocytes and PBLs from mice untreated (naïve), CRC, or CRC-bearing mice treated with 5-FU or 5-FU and CPT-11 were fixed, permeabilized, and double stained for the expression of CD247 (ζ-chain) as shown by mean fluorescence intensity (MFI), measured in gated CD3+ cells. Data from three independent experiments is presented (n=3). Statistical analyses using t test indicated significant differences at 95%. Means and SEM are shown. *, P<0.05; **, P<0.01. Abbreviations: Norm. (normal).

Figure 23A:
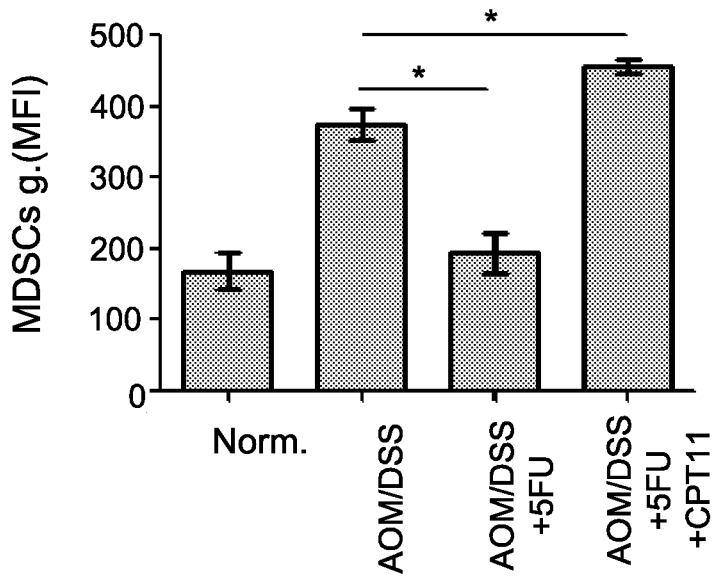
Figure 23B:
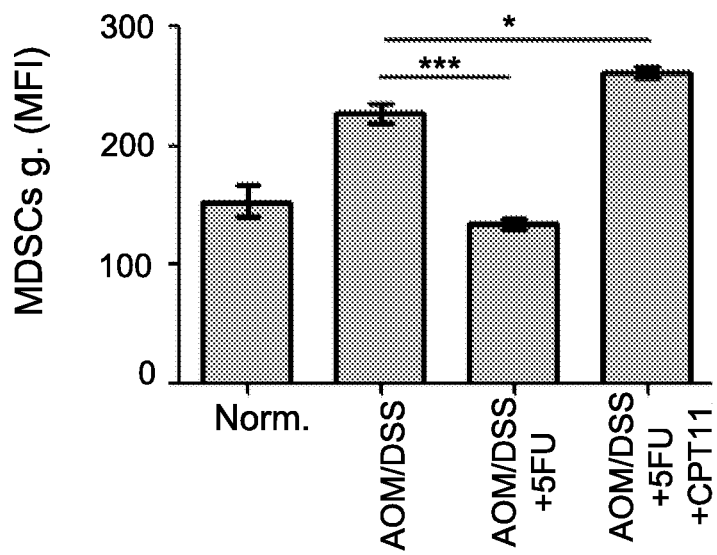

FIG. 23A-23B: 5-FU monotherapy and 5-FU with CPT11 combined therapy display opposite effect on MDSC suppressive activity Splenocytes isolated from normal mice, CRC mice or CRC mice treated with 5-FU alone or in a combination with CPT11 (n=5) were analyzed for nitric oxide (NO, FIG. 23A) and reactive oxygen species (ROS, FIG. 23B) production, both by flow cytometry analysis gaiting on the MDSCs (Gr1+CD11b+) population. Histograms represent production levels, as shown by mean fluorescence intensity (MFI). Data from three independent experiments (n=3) are presented. Statistical analyses using t test indicate significant differences at 95%. Means and SEM are shown. *, P<0.05; **, P<0.01. Abbreviations: Norm. (normal), g. (gated).

FIG. 24A-24H. The immunosuppressive environment is detected within the tumor target site Colons from three independent experiment (n=5) were isolated and single cell suspensions of the epithel and lamina propria were performed. MDSCs infiltration in (FIG. 24A, 24B) lamina propria and (FIG. 24C, 24D) epithel, was detected by flow cytometry analysis. Graphs represent the percent and absolute number of MDSCs within each fraction in the colon. (FIG. 24e, 24f) $NO^-$ production was revealed in the epithel (FIG. 24E) and lamina propria (FIG. 24F) by flow cytometry analysis gating on MDSC (Gr1+CD11b+) populations within each fraction separated from the colons. (FIG. 24G, 24H) CD247 expression levels in T cells infiltrating the different colon regions were analyzed by flow cytometry analysis. Graphs (means of triplicates±s.e.m., n=4) are representative of a typical experiment out of three independent ones. *, P<0.05; , P<0.01; *, P<0.001. Abbreviations: Norm. (normal), Lam. P. (lamina propria), ep. (epithel)

Figure 25A:
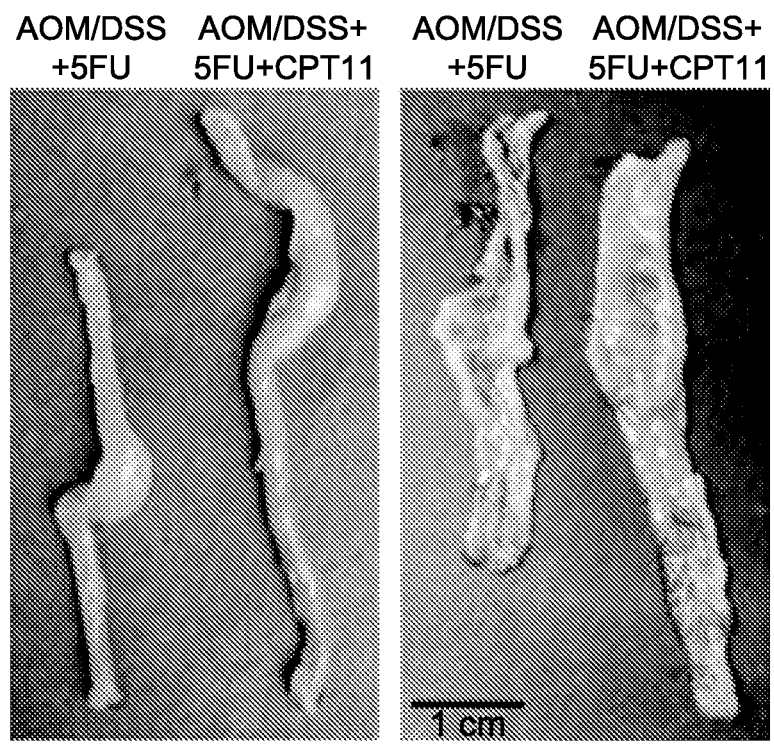
Figure 25B:
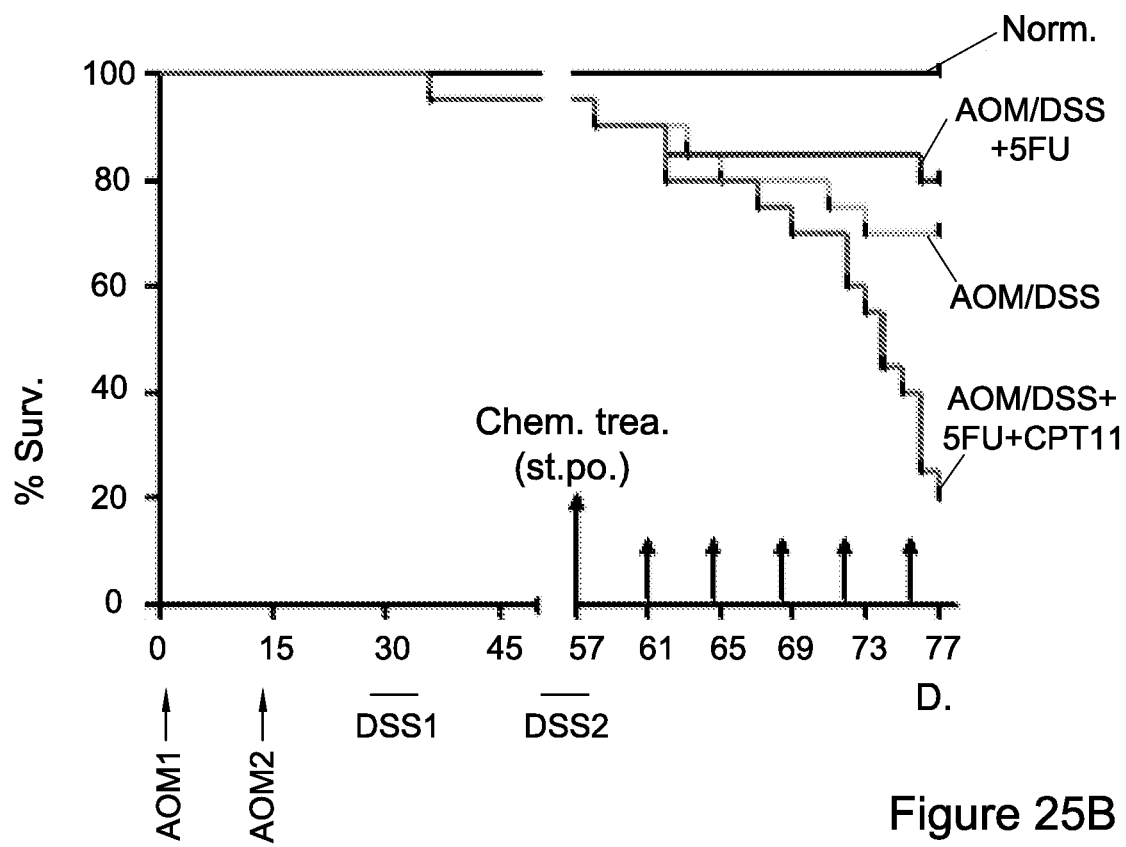

FIG. 25A, 25B. Colon structure and survival curves of CRC-bearing mice treated with 5fU or 5FU/CPT11.

FIG. 25A. A representative colon structure is presented, indicating large-number adenoma-covered sites after the combined treatment. Data from three independent experiments (n=3) is presented. 5-FU or 5-FU/CPT-11 controversially affecting the survival of CRC mice.

FIG. 25B. Survival of mice CRC, CRC-5-FU or CRC-5FU/CPT-11 treatment is shown as Kaplan-Meyer curve (n=20). Time points of AOM injections and the period of DSS addition are represented by gray arrows and lines, respectively. Start point of chemotherapy treatment and continual boosts are shown as black arrows.

Abbreviations: Norm. (normal), Chem. Trea. (chemotherapy treatment), D. (days), Sur. (survival).

DETAILED DESCRIPTION OF EMBODIMENTS

Monitoring the function of the immune system in patients suffering from a disease or health conditions associated with chronic inflammation may enable inter alia, identifying responders vs. non-responders to immune-based therapies, to evaluate therapeutic efficacies in cases of immune- or chemo-therapy, and also to follow the disease regression or recurrence.

Such monitoring is expected to lead to an intelligent selection of the timing, the amount, and of the nature of an agent to be administered for treatment of a disease or health condition associated with a chronic inflammation, such that this agent may be used at the personalized level. Moreover, the quality of life of such patients could be significantly improved, with the expectation of fewer disease cases such as in cancer declined tumor progression and metastasis and avoiding opportunistic infections. Moreover, such a monitoring may also reduce the high expenses required for continuous costly patient's examinations, which may be less frequently performed.

The Inventors have discovered the biomarker CD247 protein that may be used to fulfill the abovementioned requirements. While the expression of the CD247 molecule is steady during both normal conditions and acute inflammation, it is modulated in the curse of chronic inflammation; down-regulation of the CD247 biomarker correlates with the immune-suppression induced by chronic inflammation [19-21].

Previously preclinical and clinical evidence provided for CD247 showed that CD247 may serve to evaluate the host's immune status.

The present invention demonstrates that CD247 may be used for predicting the success of given immune-based therapies (e.g. vaccination, antibody-mediated, adoptive cell transfer, etc), for evaluating the beneficial effects of biological therapies [(e.g. etanercept, anti-inflammatory drugs (sildenafil)] and more importantly, for determining the effect of various chemotherapeutic drugs.

Clear evidence is provided that biological treatments and chemotherapeutic agents or drugs affect the immune system of the host. While some chemotherapeutic agents were shown by the Inventors to be beneficial in neutralizing the chronic inflammatory-induced immune-suppression (e.g. 5-fluorouracil), other chemotherapeutic agents enhanced the immunosuppressive environment, resulting in an increased propensity that the tumor will escape the host's immune response and in an increased risk of metastasis.

The inventors have previously shown that chronic inflammation leads to immune-suppression, impairing the function of both the innate (NK cells) and adaptive (T cells) immune systems, in association with CD247 ($\xi$ chain) [20-21] and SNX9 [WO 2012/104836] down-regulation in secondary lymphatic organs and peripheral blood.

Chronic inflammation-induced immune-suppression was identified to be mediated by myeloid-derived suppressor cells (MDSCs), which are observed during various inflammatory conditions including in tumor-bearing mice, as well as in patients with various types of cancer [21-24]. MDSCs represent a heterogeneous population of immature myeloid cells originating in the bone marrow and in the course of chronic inflammation, are highly expanding in peripheral lymphatic organs, imposing their immunosuppressive function and eliminating any anti-tumor immune response [21, 24-26].

The present invention is also based on the findings that the generated immunosuppressive environment sensed by measuring the expression levels of the biomarker CD247 is harmful to various immune based therapies. Adoptively transferred T and NK cells lose their immune function within 24 hours and thus, the host may be unable to respond to a given vaccination. Upon administering a treatment that neutralizes the chronic inflammatory factors and cells, the host's immune system is recovered, enabling a successful response to immune-based therapy.

The present invention is also based on the findings that CD247 may be used as a biomarker for identifying the effect of chemotherapeutic agents or biologic or anti-inflammatory drugs on the immune system of the host. Chemotherapeutic agents were found to be either harmful to the immune system, i.e. enhancing the immune-suppression state of the subject by elevating the numbers of MDSCs and the suppressive activity thereof, and resulting in further CD247 down regulation associated with a more pronounced immunosuppression. In contrast, other chemotherapeutic agents were found to be beneficial to the host, as they decrease the numbers of MDSCs and thus the suppressive activity thereof, ensuing in the recovery of the expression levels of CD247.

Interestingly, although, all the drugs and biological compounds used in this study were approved by the FDA and are currently being used for the treatment of humans, the present invention demonstrated that the mechanisms underlying the activity of these drugs as well as their effect on the immune system are yet not fully understood.

The present invention is based on the finding that the expression level of CD247 in cells can allocate patients suffering from chronic inflammation and associated immune-suppression. CD247 can be used as a specific and reliable biomarker for selecting a suitable treatment for said patient such that the immune-suppressive environment of the patient will not be further aggravated or cured.

The important role of chronic inflammation and more specifically, of the generated MDSCs in suppressing immune responses, highlights the need to eliminate the inflammatory environment. Therefore, the general propose of the present invention is to manipulate the host's inflammatory environment and MDSCs' harmful effects in order to increase the potency of the host's immune response as the anti-tumor immune response in cases of cancer, by taking advantage of known chemotherapy treatments with or without a combination of immune-based or biological therapeutic strategies. As presented herein, the first step was to assess clinically approved chemotherapeutic agents for their mode of function and allocating those that not only affect the tumor but also have the capacity to counteract the tumor associated chronic inflammation-induced immunosuppression. To this end, the inventors have used their previously established mouse model system that mimics the chronic inflammation-induced immunosuppressive conditions, as observed in hosts with developing tumors. These mice were treated with several chemotherapy cell cycle specific and non-specific (alkylating) drugs, and immune-based and biological drugs using therapeutic concentrations approved by the FDA.

The present invention show for the first time that CD247 could be used as biomarker for detecting the effect of chemotherapeutic and biologic drugs on the hosts' immune system under developing chronic inflammatory conditions as observed in some cancer patients. By monitoring CD247 expression level in secondary lymphatic organs, peripheral blood and sites of the growing tumors (biopsies) prior to and/or following treatments the inventors discovered that chemotherapeutic drugs not only act in arresting tumor growth, but also influence dramatically the individual's immune status.

Although there are evidence suggesting a synergistic effect of chemotherapy and immunotherapy, the present invention shows a significant suppression of the immune system following treatment with several chemotherapeutic agents, that involves not only a depletion of lymphocytes as was reported previously but also as inducers of extremely high expansion of MDSCs in the periphery, lymphatic organs and sites of growing tumors, resulting in impaired immune function within the host, and neutralization of any therapeutic strategy that is based upon stimulating/enhancing the host's immune response or on donor adoptively-transferred cells. The present invention shows that while some chemotherapy treatments [Doxorubicin (Rubex), Busulfan and 5-fluorouracil (5-FU)] lead to immune recovery from the immunosuppressive state observed in mice with chronic inflammation, surprisingly, other drugs [Irinotecan (CPT11) and Cyclophosphamide (CP)] lead to opposing results; highly increasing peripheral immunosuppression as indicated by changes in several key parameters in the spleen, peripheral blood and specific sites of growing tumors. The biomarker CD247, which senses the individual's immune status, was dramatically down-regulated, indicating an immunosuppressive stage. Indeed, the inventors show that MDSC levels were increased and their maturation state decreased, MDSC suppressive function was elevated, measured by nitric oxide (NO—) and reactive oxygen species (ROS) secretion, and in-vivo killing activity mediated by NK cells and T cell proliferative capacity were dramatically reduced, all parameters implying an enhanced immunosuppressive environment. Therefore, the vision of the present inventors is that in cases of cancer, treatment must be dually targeted against the tumor cells and the chronic inflammatory microenvironment (that may lead to a systemic chronic inflammatory condition). The first aimed at tumor destruction and the second at breaking the immunosuppressive stage. Chemotherapy can weaken immunity by causing a drop in the number of white blood cells, and leading to an increased MDSCs accumulation, resulting in a strong immunosuppression and failure of host's immune system to fight against the residing tumor cells or failure of administered immune-based or biological treatments. The results of the present invention highlight a new concept that CD247 can serve as a tool for detecting whether some chemotherapy drugs have the capacity to neutralize and others enhance immunosuppression. This concept can be crucial when designing cancer treatments aimed at avoiding disease recurrence. Moreover, this could form the basis for considering combinatorial treatment combining chemotherapy with immune-based or biological therapy to induce a global surrounding supporting anti-tumor immune response.

The present invention provides as well new data on the use novel biomarkers that could sense the immune status prior to and/or following a given therapy and their use in establishing optimal personalized treatments.

Thus, according to a first aspect, the invention relates to a method for determining the efficacy of a treatment with a therapeutic agent on a subject suffering from a pathologic disorder that leads to a chronic inflammatory condition. More specifically, the method of the invention provides and enables determining whether a subject suffering from a chronic inflammatory condition would respond, and specifically, exhibit a beneficial response to a treatment with a therapeutic agent. According to certain embodiments, the therapeutic agent used for treating this subject may be at least one chemotherapeutic agent, at least one immunotherapeutic agent, biologic agent or any combination thereof. More specifically, the method of the invention may comprise the steps of:

In a first step (a), determining the level of expression of T cell antigen receptor (TCR) $\zeta$ chain (CD247) in at least one biological sample of said subject, to obtain an expression value. It should be noted that at least one examined sample must be obtained after or during the initiation of the treatment.

The next step (b) involves determining if the expression value obtained in step (a) is any one of, positive, negative or equal to a predetermined standard expression value (that is also referred to herein as a cutoff value) or to an expression value of CD247 in a control sample. Determination of a positive or negative expression value may be performed by comparing the expression value obtained in step (a) to a predetermined standard expression value or to an expression value of CD247 in a control sample. Such a step involves calculating and measuring the difference between the expression values of the examined sample and the cutoff value and determining whether the examined sample can be defined as positive or negative. More specifically, as used herein the term "comparing" denotes any examination of the expression level and/or expression values obtained in the samples of the invention as detailed throughout in order to discover similarities or differences between at least two different samples. It should be noted that comparing according to the present invention encompasses the possibility to use a computer based approach.

It should be noted that in certain embodiments, a positive expression value of CD247 in the tested sample indicates that the subject responds to the treatment and moreover, may exhibit a beneficial response to the treatment. More specifically, it should be noted that in certain embodiments, the predetermined standard values (cutoff values) are calculated and obtained from populations of subjects suffering from the same chronic inflammatory condition that responded well to the same therapeutic agent, subjects not responding, healthy subjects and untreated subjects. Similarly, where control samples are used instead of, or in addition to predetermined cutoff values, such controls may include subjects suffering from the same chronic inflammatory condition that responded well to the same therapeutic agent, subjects not responding, healthy subjects and untreated subjects. Therefore, a positive expression value or an equal value (when compared to cutoff representing the responder population), reflect up-regulation of CD247 expression, and indicates that the examined subject belongs to a pre-established population associated with a beneficial response to the specific treatment. It should be understood that such up-regulation, should be considered as up-regulation relatively to the expression prior to the initiation of the treatment. In more specific embodiments, such up-regulation may be expression of CD247 in the range of or similar to the levels of the expression in healthy subjects (age and gender matched) that do not suffer from any chronic inflammatory condition. In contrast, a negative expression value, that is a result of down regulated expression of CD247, indicates that the examined subject does not respond to said treatment and more specifically, does not exhibit a beneficial response to the treatment. Similarly, "down-regulated expression" reflects a decrease in the expression of CD247 that is below the expression levels in healthy or responder subjects. Thereby, the method of the invention provides determination of the efficacy of a specific treatment on a specific subject that suffers from a chronic inflammatory condition.

The method of the invention provides determining the suitability for treatment of a patient suffering from a disease associated with a chronic inflammatory condition a-priori, i.e., before the onset of such treatment, or in most cases, in early stages of the treatment, enabling a personalized treatment. Thus, the method of the invention will enable avoiding a treatment that will potentially aggravate the chronic inflammatory condition or the immune-suppressive environment in said patient and the selection of a treatment that will be beneficial to the specific patient.

Similarly, the method of the invention provides determining the suitability and efficacy of treatment of a patient suffering from a disease associated with a chronic inflammatory condition during said treatment, i.e. after the onset thereof, to monitor the effect of said treatment on the patient. Wherein, by using the method of the invention, the expression value of CD247 decline below a predetermined value or below the expression value in a control sample obtained from the patient prior to the onset of the treatment, or during the treatment, the treatment may be ceased, and alternative treatments may be sought for by the method of the invention, thus avoiding the deleterious effect that may accompany ensuing such treatment on the immune system.

The method of the invention provides the use of CD247 as a biomarker for sensing the effect of a therapeutic agent, specifically, chemotherapeutic drug, anti-inflammatory drug, biological drug, on a patient and thereby determining the efficacy of a suggested treatment on a particular patient. The protein T-cell receptor zeta (ζ) chain (CD247), also termed CD3 zeta and "T-cell receptor T3 zeta chain" (also known by other human synonyms, including T3Z, CD3H, CD3Q, CD3Z, TCRZ and CD3-ZETA). CD247, together with T-cell receptor alpha/beta and gamma/delta heterodimers, and with CD3-gamma, -delta and -epsilon, forms the T-cell receptor-CD3 complex. The zeta chain plays an important role in coupling antigen recognition to several intracellular signal-transduction pathways. Low expression of the antigen results in impaired immune response.

The T-cell antigen receptor (TCR) is a multisubunit receptor complex specific to T cells subserving both antigen recognition and signal transduction functions. The CD247 [zeta (ζ) chain] of the TCR is a component of all surface receptor complexes. Sequence analysis of cDNAs encoding human and murine ζ revealed that it is a highly conserved protein. In addition to amino acid homology, there is remarkable interspecies conservation in the nucleotide sequence of the 5' and 3' untranslated regions of the ξ mRNA. The ξ subunit has no sequence similarity to the CD3 chains and the localization of the human ξ gene to the centromeric region of chromosome 1 underscores the fact that it is a distinct genetic component of the TCR.

It should be appreciated that in certain embodiments, as used herein in the specification and in the claim section below, CD247 protein refers to the human CD247 protein. More specifically, in humans, several variants of CD247 were reported. In certain embodiments the human CD247 protein is as denoted by the sequence herein referred to as SEQ ID NO. 1 (GeneBank accession number J04132.1), encoded by the nucleic acid sequence as denoted by SEQ ID NO. 2. It should be further appreciated that other variants of CD247 may be also applicable for the present invention. Non limiting examples include the human CD247 proteins as also referred to by the accession number GI: 62898210, GI: 164696323 and GI: 19344013. CD247 sequences are also denoted by the terms "T-cell surface CD3 zeta chain isoform 1 precursor" and "T-cell surface CD3 zeta chain isoform 2 precursor.

Still further, the invention refers (specifically in the Examples section) in some particular embodiments to CD247 [Mus musculus] that is a mouse, CD247 protein of GeneBank accession number M19729.1. According to certain embodiments, the amino acid sequence of said mouse CD247 as referred to herein is denoted by the sequence SEQ ID NO. 3, encoded by the nucleic acid sequence as denoted by SEQ ID NO. 4.

According to certain specific embodiments, the method of the invention may comprise a further step of calculating the rate of change in the expression value of CD247 in response to the specific examined treatment. The rate of change in the expression in response to treatment reflects the responsiveness of the examined subject to the particular therapeutic agent. Moreover, the rate of change in CD247 expression indicates if the treated subject exhibits a beneficial response for such treatment. More specifically, such method may comprise the steps of:

The first step (a) involves determining the level of expression of CD247 in at least one biological sample of the examined subject to obtain an expression value. It should be noted that the sample is obtained after the initiation of the examined treatment.

In the next step (b), the level of expression of CD247 is determined in at least one more biological sample of the same subject to obtain an expression value. It should be noted that the sample may be obtained prior to initiation of said treatment.

In the next step (c) the rate of change between the expression value obtained in step (a), and the expression value obtained in step (b) is calculated.

Finally, step (d) involves determination if the rate of change obtained in step (c) is any one of, positive, negative or equal to a predetermined standard rate of change (cutoff value). More specifically, such standard rate of change is determined prior and after the initiation of treatment with the same therapeutic agent, for population of subjects suffering from the same pathologic disorder defined as "responders". It should be also understood that in certain embodiments, the level of CD247 in a sample after treatment, may also be evaluated as compared to standard value obtained for a population of age and gender matched healthy subject that do not suffer from any pathologic disorder. In an alternative embodiment, where control samples are used, this step involves determining if the rate of change is positive, negative or equal as compared to the rate of change calculated for expression values in at least one control sample obtained prior and following the specific treatment. Such step involves calculating and measuring the difference between the rate of change in the expression values of the examined sample and the standard rate of change (cutoff value) and determining whether the examined sample can be defined as positive or negative. It must be understood that the standard rate of change (cutoff value) were calculated for populations of patients suffering from the same pathologic disorder (that are not treated), subjects treated with the same therapeutic agent (responders or non-responders) and healthy subjects (age and gender matched). It should be also appreciated that the predetermined standard values (cutoff) may be presented in a standard curve. Similarly, if control samples are used in the method of the invention, such controls may include samples from patients suffering from the same pathologic disorder (untreated or treated with the specific therapeutic agent), subjects suffering from the same condition treated with the same therapeutic agent that are responders, samples of non-responders and samples of healthy subjects (age and gender matched).

According to certain embodiments, a positive or equal rate of change of CD247 expression value reflects elevation in the expression of CD247 in response to said treatment relative to prior sample and or cut offs as above and therefore indicates that the examined subject responds to the certain treatment and specifically exhibits a beneficial response to the treatment. More particularly, a positive rate of change indicates that the examined subject belongs to a pre-established population associated with a higher probability to exhibit a beneficial response to the specific examined treatment. A negative expression value relative to prior sample and or cut offs as above indicates that the examined subject does not respond and specifically, does not exhibit a beneficial response to the treatment. In more particular embodiments, a negative rate of change reflects reduction of CD247 expression in response to treatment with a specific therapeutic compound revealing a chronic inflammatory state in the patient and thereby indicating that the specific therapeutic agent is not appropriate for said examined patient. The efficacy of the specific treatment in a specific subject is thereby determined.

In sensing the specific effect of a particular therapeutic agent on a certain subject, the method of the invention may be used for personalized medicine, namely adjusting and customizing healthcare with decisions and practices being suitable to the individual patient by use of any additional information collected at different stages of the disease.

Thus, in yet another alternative embodiment, the invention further provides a simple approach for assessing responsiveness of a mammalian subject to a specific treatment with a therapeutic agent as indicated above, or evaluating the efficacy of the specific treatment on a subject suffering from a chronic inflammatory condition. Accordingly, the method of the invention may comprise:

In a first step (a) determining the level of expression of CD247 in a biological sample of the subject to obtain a CD247 expression value in the tested biological sample. It should be noted that the sample is obtained prior to initiation of said treatment.

In the next step (b) determining the level of expression of CD247 in at least one other biological sample of the subject to obtain a CD247 expression value in the sample. It should be noted that the at least one other sample is obtained after or during the initiation of the specific treatment.

Step (c) involves comparing CD247 expression value in the biological sample obtained in step (a), with at least one CD247 expression value obtained in step (b). As noted above, it must be understood that the level of CD247 expression in a sample should be also compared to a predetermined standard levels of expression calculated for a population of age and gender matched healthy subjects. This comparison should be performed against a CD247 cut off value or standard curve of control/healthy individual expression levels or responders exhibiting the same pathology. In more specific embodiments, a higher CD247 expression value in a sample obtained after initiation of the treatment according to step (b) as compared to the CD247 expression value in a sample obtained prior to initiation of said treatment according to step (a), and compared with the standard curves of control/healthy individual expression levels or responders exhibiting the same pathology, is indicative of a successful therapy.

The method of the invention is based on determining the expression level of a specific biomarker, CD247, in a sample. The terms "level of expression" or "expression level" are used interchangeably and generally refer to the amount of a polynucleotide or a protein in a biological sample. "Expression" generally refers to the process by which gene-encoded information is converted into the structures present and operating in the cell. Therefore, according to the invention "expression" of a gene, specifically, a gene encoding CD247 may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis.

It should be noted that the expression level is reflected by measurement and determination of an expression value. As used herein, the term "expression value", "level of expression" or "expression level" refers to numerical representation of a quantity of a gene product, which herein is a protein, but may also be an mRNA.

It should be noted that a subject will be considered suitable for treatment when the expression value of CD247 (or as will be explained herein after, a normalized expression value of CD247) determined in a biological sample obtained from said subject is equal, within the range of or above ("positive") a corresponding predetermined (normalized) expression value of CD247 obtained for a population of patients exhibiting a beneficial effect in response to treatment with the same therapeutic agent (a successful treatment). Alternatively, when control samples are used instead of—or in addition to—a predetermined standard (cutoff), the expression value of the sample is compared to the expression values obtained for the control sample. A higher expression value of CD247 in response to a certain treatment (up-regulated expression) is determined as "positive" rate of change and a lower expression value of CD247 in response to said treatment (down-regulated expression) is determined as "negative" rate of change. As noted herein, before the calculated rates of change in the CD247 expression in response to treatment, it should be compared to the standard rates obtained for populations of subjects suffering from the same condition untreated or treated with the same compound that are defined as responders or non responders, as well as to healthy control subjects.

To disambiguate, a "positive", "higher" or "up-regulated" expression value of CD247, or rate of change in the expression of CD247 in response to treatment determined in said biological sample indicates that the subject is suitable for the specific treatment and exhibits a beneficial response. In other embodiments, the specific therapeutic agent is suitable and effective to the particular examined patient, where the expression value (specifically, the normalized expression values or rate of change) of CD247 determined in the biological sample is in the range of the normalized expression value of CD247 obtained in a suitable control sample or a corresponding predetermined standard expression value (cutoff values) of CD247, specifically, a standard rate of responder population, by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 70%, at least 80%, at least 90% or more.

Non-limiting examples of such differences are presented in Example 2 (FIG. 9). This example demonstrates the rate of change in an expression value of CD247 determined in a biological sample during a treatment with doxorubicin, where an increase of about 24% in the expression value of CD247 was obtained upon treatment with doxorubicin, indicative of the suitability of said treatment to said subject. Similarly, Example 2 (FIG. 11) demonstrates an expression value of CD247 determined in a biological sample during a treatment with busulfan, where an increase of about 23% in the expression value of CD247 was obtained upon treatment with this agent, indicative of the suitability of said treatment to said patient.

Generally, CD247 expression values (specifically, normalized expression values or rate of change in the expression of CD247) that are determined as "negative" as being lower than the normalized expression value of CD247 obtained in a suitable control sample, or a corresponding predetermined standard expression value (cut-off) of CD247, correlate with an aggravation of the chronic inflammation condition or immune-suppressive environment of said patient in response to treatment with a specific therapeutic agent, and therefore indicate that this specific examined therapeutic agent may not be suitable for treating the specific subject that suffers from a specific chronic inflammatory condition. Such control or cutoff value may be obtained from a population of age and gender matched healthy subjects and/or a population of subjects suffering from the same pathologic condition that respond well to the same treatment (responders). Moreover, such "negative" expression value or rate of change in response to a specific treatment, should be in the range (+/−SD) of cutoff value determined for a population of subjects suffering from the same pathological disorder that are considered as not responding to the treatment, indicating that the examined patient belongs to said population.

As shown by the present invention as disclosed in the following Examples, reduced, or lower expression of CD247 in response to treatment with a therapeutic agent is correlated with a chronic inflammation status, and thereby indicates that the tested subject would not respond or would not exhibit a beneficial response to treatment with the specific therapeutic agent. Thus, "Low level of expression", or "negative" expression values or rate of change, when applicable, as used herein for CD247, denotes a level significantly (e.g. as determined by statistical determination) lower than a predetermined standard.

On the other hand, increased, or higher expression of CD247 in response to treatment with a therapeutic agent is correlated with an improvement in the chronic inflammation status, and thereby indicates that the tested subject would respond and exhibit a beneficial response to treatment with the specific therapeutic agent. Thus, "high level of expression", or "positive" expression values, or rate of change, when applicable, as used herein for CD247, denotes a level significantly (e.g. as determined by statistical determination) higher than the expression before treatment that is in the range of a predetermined standard. It should be noted that such standard value is predetermined for a population of patients suffering from the same pathologic condition that perform beneficial effect "responders". Therefore, expression value or rate of change that is within the range of such cutoff indicates that the examined subject belongs to a population of responders.

"Standard" or a "predetermined standard" as used herein, denotes either a single standard value or a plurality of standards with which the level of CD247 expression from the tested sample is compared. The standards may be provided, for example, in the form of discrete numeric values or is calorimetric in the form of a chart with different colors or shadings for different levels of expression; or they may be provided in the form of a comparative curve prepared on the basis of such standards (standard curve). The standards may be prepared by determining the level of expression of CD247 present in a sample obtained from a plurality of patients that were diagnosed or determined (by other means, for example by a physician, by histological techniques etc.) as performing a beneficial response ("responders") to a certain treatment and a population of patients that do not respond well to the same therapeutic agent (non-responders, being correlated with a low level of expression of CD247). The level of expression for the preparation of the standards may also be determined by various conventional methods known in the art. The methods of the invention may be carried out in parallel to a number of standards of healthy subjects and subjects of different chronic inflammatory condition states that respond or not respond to a certain treatment and the level determined in the assayed sample is then compared to such standards. After such standards are prepared, it is possible to compare the level of CD247 expression obtained from a specific tested subject to the corresponding value of the standards, and thus obtain an assaying tool. Similar approach is applied when the rate of change in the expression value is calculated in response to treatment with the therapeutic agent.

As described hereinabove, step (d) and in some embodiments, step (b), of the method for determining the efficacy of a treatment with a therapeutic agent on a subject suffering from a chronic inflammatory condition provided by the invention, refers to a predetermined standard expression value (step b), or when applicable (in step d), a predetermined standard rate of change, that in other words may be defined as predetermined "cutoff" values. It should be noted that a "cutoff value", sometimes referred to simply as "cutoff" herein, is a value that meets the requirements for both high sensitivity (true negative rate) and high specificity (true positive rate). CD247 expression level values that are higher ("positive") or lower ("negative") in comparison with said CD247 expression corresponding cutoff value or a predetermined standard expression value or rate of change, indicate that the examined sample belongs to a pre-established population associated with a specific chronic inflammation rate in response to a specific treatment with a therapeutic agent (low or high, respectively) and limited to the said sensitivity and specificity. The specific cutoff value reflects the threshold, indicating whether a specific population exhibits a beneficial response to a certain treatment, or in contrast, exhibit a harmful effect in response to the same treatment.

It should be noted that the terms "sensitivity" and "specificity" are used herein with respect to the ability of the biomarker of the invention, CD247, to correctly classify a sample as belonging to a pre-established population associated with a specific probability to respond (exhibit a beneficial effect) to a specific therapeutic agent, and thereby to determine whether a certain therapeutic agent is suitable for treatment as leading to a beneficial effect, or alternatively, is not suitable for treatment of the particular pathologic condition, as leading to a deleterious effect on the immune system of the treated subject.

"Sensitivity" and "specificity" indicate the performance of the biomarker of the invention, CD247, with respect to correctly classifying samples as belonging to pre-established populations that are likely to display a beneficial effect in response to a certain treatment ("responders"), or alternatively, to correctly classify the sample a belonging to pre-established populations of "non-responders" to the specific agent that display a chronic inflammation status. In case where said CD247 expression values are within the range of a cutoff value defined for a population of "responders", that is, "positive" values indicating elevated expression of CD247 in response to the particular treatment reflecting improvement in the chronic inflammation states, more specifically, indicating that the diseased subject is more likely to display a beneficial response to the specific therapeutic agent, that leads to reduction, and preferably, elimination of the chronic inflammation than corresponding pre-established populations wherein said corresponding CD247 expression values in response to treatment with the same therapeutic agent, are lower than the cutoff predetermined for responsive population or healthy controls (age and gender matched), that is, "negative" values indicating lower beneficial effect, and thus, higher chronic inflammation rates.

Simply put, "sensitivity" relates to the rate of correct identification of high-chronic inflammation rate samples that reflect a non suitable therapeutic agent, as such out of a group of samples (true negatives), whereas "specificity" relates to the rate of correct identification of low-inflammation rate samples reflecting a suitable treatment as such out of a group of samples, in a reproducible manner (true positives).

Cutoff values may be used as a control sample, said cutoff values being the result of a statistical analysis of CD247 expression value differences in pre-established populations with either a chronic inflammation state, reflecting "non-responsiveness" or deleterious effects of the specific therapeutic agent or alternatively, populations of "responsive" or "healthy" subjects with no inflammation or reduced inflammation in response to a successful treatment.

Specifically, it is understood that CD247 expression values or rate of change in response to treatment with a certain therapeutic agent, that are lower than the cutoff value found by the inventors (i.e., "negative" expression value), reflects a higher tendency for chronic inflammation in a patient treated with said agent (indicating that the therapeutic agent is not suitable) than a patient where the corresponding CD247 expression of CD247 is elevated in response to treatment and therefore, the expression value (or the rate of change in the expression) falls within the range of the cutoff value (i.e., "positive" results). Thus, a given population treated with a specific therapeutic agent, having specific clinical parameters will have a defined likelihood to respond or alternatively, not respond (developing chronic inflammation) based on the expression values of CD247 that may be within the range of or below said cutoff values. It should be emphasized that the nature of the invention is such that the accumulation of further patient and/or healthy donors data may improve the accuracy of any obtained cutoff values, which are usually based on an ROC (Receiver Operating Characteristic) curve generated according to accumulated patient and/or healthy donors data using, for example, a commercially available analytical software program. The CD247 expression values are selected along the ROC curve for optimal combination of sensitivity and specificity, which are as close to 100% as possible, and the resulting values are used as the cutoff values that distinguish between patients who will display chronic inflammation at a certain rate in response to a specific treatment, and those who will display a beneficial response to the same therapeutic agent that is reflected by reduced inflammation (with said given sensitivity and specificity). The ROC curve may evolve as more and more patient-chronic inflammation and healthy donor data and related CD247 expression values are recorded and taken into consideration, modifying the optimal cutoff values and improving sensitivity and specificity. Thus, any cutoff values should be viewed as a starting point that may shift as more patient-chronic inflammation data in response to a specific treatment allows more accurate cutoff value calculation. It should be noted that healthy subjects used in the invention as control samples or standard curves are age and gender matched subjects. It should be further appreciated that standard curves for "responders" may be prepared specifically for each pathologic condition, and in some embodiments, also for each therapeutic agent (or treatment regimen).

More specifically, and as explained earlier, the inventors have analyzed the expression values of CD247 in response to treatment with a certain therapeutic agent, further, in order to discover specific cutoff values, a deviation from which is indicative of an increased likelihood for reduced chronic inflammation and immuno-suppression state in response to treatment with a specific therapeutic agent of a tested subject that suffers from a chronic inflammatory condition, thereby determining the efficacy of a specific treatment with a certain therapeutic agent. It should be appreciated that an important step in the method of the invention is determining whether the expression value of CD247 (specifically, normalized) is "positive" and thereby belongs to a pre-established population with an associated specific likelihood of exhibiting a beneficial effect in response to the specific agent, or is "negative" and thereby belongs to a pre-established population with an elevated or unimproved chronic inflammation state (non-responsive). Such step involves calculating and measuring the difference between (thereby comparing) the expression values of the examined sample and the cutoff value and determining whether the examined sample can be defined as positive or negative. The presence of CD247 with a "positive" normalized expression value in response to treatment with a specific therapeutic agent (or rate of change, when applicable), indicates that the subject belongs to a pre-established population with an associated reduced chronic inflammation state which is lower than the chronic inflammation state associated with, ceteris paribus, subjects where CD247 have "negative" normalized expression values (or rate of change, when applicable) in response to the same treatment, indicates a reduced expression of CD247 and an elevated chronic inflammation state. Thus, "positive" and "negative" referring to the relation of said expression values to said cutoff value. According to certain embodiments a "positive result" may be determined where a normalized value of CD247 is elevated in response to treatment and therefore, the expression value of the sample is within the range [+1-SD (Standard Deviation)] of the cutoff value and therefore predicts reduction and sometimes elimination of the chronic inflammation and associated immuno-suppression, in response to treatment with a specific agent, indicating the suitability of the treatment for the specific subject.

More specifically, as used herein the phrase "a decrease below a predetermined cutoff or threshold" reflects a decrease or no improvement in CD247 expression in response to a certain treatment (that is a reduced or non existing rate of change), determined in the sample of the subject suffering from a chronic inflammatory condition relative to the reference expression or rate of change in the expression in response to treatment, which is lower than a predetermined cutoff or threshold such as about 10%, e.g., lower than about 20%, e.g., lower than about 30%, e.g., lower than about 40%, e.g., lower than about 50%, e.g., lower than about 60%, lower than about 70%, lower than about 80%, lower than about 90%, lower than about 2 times, lower than about three times, lower than about four time, lower than about five times, lower than about six times, lower than about seven times, lower than about eight times, lower than about nine times, lower than about 20 times, lower than about 50 times, lower than about 100 times, lower than about 200 times, lower than about 350, lower than about 500 times, lower than about 1000 times, or more relative to the reference ratio. Such a decrease and reduction indicates that the specific therapeutic agent is not suitable for treating the tested subject. According to some alternative embodiments of the invention, an identical rate of change (within the range of) in the expression of CD247 in response to such treatment, or a change above a predetermined cutoff or threshold in the ratio determined in the sample of the treated subject that suffers from a chronic inflammatory condition as compared to the reference rate of change indicates the reduction or elimination of the chronic inflammation, and thereby, a successful treatment with the specific therapeutic agent. More specific embodiments for such elevation may include about 10%, e.g., higher than about 20%, e.g., higher than about 30%, e.g., higher than about 40%, e.g., higher than about 50%, e.g., higher than about 60%, higher than about 70%, higher than about 80%, higher than about 90%, higher than about 2 times, higher than about three times, higher than about four time, higher than about five times, higher than about six times, higher than about seven times, higher than about eight times, higher than about nine times, higher than about 20 times, higher than about 50 times, higher than about 100 times, higher than about 200 times, higher than about 350, higher than about 500 times, higher than about 1000 times, or more relative to the reference rate of change.

As noted above and in the Examples section above, it should be appreciated that the reduction in the expression of CD247 in response to a treatment with a specific therapeutic agent, constitutes an early marker of a deleterious effect of the treatment (or non-responsiveness to a given treatment) reflected by an elevated inflammatory state that may indicate the regression or recurrence of a chronic inflammatory condition. Thus, by monitoring the treated patient for expression patterns of CD247, medical staff may become aware of a regression or recurrence of the diseases earlier than they currently are, and consequently, provide earlier and more effective treatment.

More specifically, in certain embodiments, wherein indicated "lower", "reduced" or "decreased" expression levels of CD247, it is meant that such decrease or reduction may be a decrease or reduction of between about 10% to 100% of the expression of such biomarker. The terms "decrease", "reduction" and "elimination" as used herein relate to the act of becoming progressively smaller in size, amount, number, or intensity. Particularly, a reduction of 10%, 15%, 20%, 25%, 30%, 35%, 40%, 45%, 50%, 55%, 60%, 65%, 70%, 75%, 80%, 85%, 90%, 95% or 100% of the expression as compared to a suitable control. It should be further noted that decrease or reduction may be also a decrease of about 2 to 100 folds. Still further, it should be appreciated that the decrease of the levels or expression of said CD247 might be either in the transcription, translation or the stability of said biomarker. With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively.

In yet further embodiments, the invention relates to a method for monitoring and assessing the efficacy of a treatment with a therapeutic agent and thereby providing information concerning the disease progression. It should be noted that the therapeutic agent may lead to either a direct or indirect anti-/pro-inflammatory effect, and therefore, CD247 levels reflect the effect of the therapeutic agent on the immune-system of the diseased subject. In more specific embodiments, such method comprises the steps of: In a first step (a) determining the level of expression CD247 in a biological sample of the examined subject to obtain an expression value. It should be appreciated that in certain embodiments, this sample may be obtained either prior to or at any time after the initiation of the treatment with the examined therapeutic agent. Step (b) involves repeating step (a) to obtain expression values of CD247, for at least one more temporally separated test sample. It should be noted that at least one of the temporally separated samples must be obtained after the initiation of the treatment. In the next step (c), calculating the rate of change of the expression values of CD247 between the temporally separated test samples. In the next step (d), determining if the rate of change obtained in step (c) is any one of, positive, negative or equal to a predetermined standard rate of change determined between at least two temporally separated samples. It should be noted that in certain embodiments, the rate of change obtained in step (c) is compared with a predetermined standard rate of change (cutoff or standard curves) determined between at least one sample obtained prior to and at least one sample obtained following interferon treatment. Alternatively, where control samples are being used, this step involves determining if the rate of change obtained in step (c) is any one of, positive, negative or equal to the rate of change calculated for expression values in the control samples obtained from at least two temporally separated samples of subjects suffering from the same pathologic condition that are considered as "responders" and from subjects considered as "non-responders", wherein at least one sample of said at least two samples is obtained after the initiation of the specific treatment.

According to certain embodiments, a "positive" rate of change of CD247 expression value indicates that the tested subject displays rate of change values that are within the range of a predetermined cutoff for subjects suffering from the same condition that are classified as "responders" or in the range of expression of healthy donors. Thus, indicating that the tested subject exhibits a beneficial response to the specific examined treatment and thereby belongs to a pre-established population associated with responsiveness to the specific treatment. A negative expression value indicates that the subject does not exhibit a beneficial response to said treatment, and therefore may be considered as a non-responder subject.

Moreover, "positive" value determined for the rate of change in CD247 expression in response to a certain treatment as specified above, indicates that the specific examined treatment is effective and results in a beneficial response in the tested subject. A "negative" rate of change indicates that said treatment is not effective. The method of the invention thereby provides monitoring the efficacy of a treatment with a therapeutic agent and the disease progression.

It should be noted that the term "response", "responsiveness", "responsive" or "responder" to treatment with a specific therapeutic agent refers to an improvement in at least one relevant clinical parameter as compared to an untreated subject diagnosed with the same pathology (e.g., the same type, stage, degree and/or classification of the chronic inflammatory condition), or as compared to the clinical parameters of the same subject prior to said treatment.

The term "non responder" or "non-responsive" to treatment using a specific therapeutic agent, refers to a patient not experiencing an improvement in at least one of the clinical parameter and is diagnosed with the same condition as an untreated subject diagnosed with the same pathology (e.g., the same type, stage, degree and/or classification of the chronic inflammatory condition), or experiencing the clinical parameters of the same subject prior to such treatment.

Of course, more samples taken in more time-points may provide a statistically robust analysis of said expression trends, and may also be utilized as a method for continuous monitoring of subjects, especially those still undergoing and those that have undergone therapy. The more samples are available over a given time period, the higher is the resolution of the expression patterns of CD247 during said period.

The number of samples collected and used for evaluation of the subject may change according to the frequency with which they are collected. For example, the samples may be collected at least every day, every two days, every four days, every week, every two weeks, every three weeks, every month, every two months, every three months every four months, every 5 months, every 6 months, every 7 months, every 8 months, every 9 months, every 10 months, every 11 months, every year or even more. Furthermore, to assess the trend in expression rates according to the invention, it is understood that the rate of change may be calculated as an average rate of change over at least three samples taken in different time points, or the rate may be calculated for every two samples collected at adjacent time points. It should be appreciated that the sample may be obtained from the monitored patient in the indicated time intervals for a period of several months or several years. More specifically, for a period of 1 year, for a period of 2 years, for a period of 3 years, for a period of 4 years, for a period of 5 years, for a period of 6 years, for a period of 7 years, for a period of 8 years, for a period of 9 years, for a period of 10 years, for a period of 11 years, for a period of 12 years, for a period of 13 years, for a period of 14 years, for a period of 15 years or more.

In practice, for monitoring purpose, to detect a decline or elevation in CD247 expression, at least two "temporally-separated" test samples must be collected from the treated patient, and preferably more. The expression of at least CD247 is then determined using the method of the invention, applied for each sample. The rate of change in this biomarker expression is then calculated by determining the difference in expression values (specifically, normalized values) of said CD247 between any two samples obtained from the same patient in different time-points or time intervals. This period of time, also referred to as "time interval", or the difference between time points (wherein each time point is the time when a specific sample was collected) may be any period deemed appropriate by medical staff and modified as needed according to the specific requirements of the patient and the clinical state he or she may be in. It should be noted that such interval could be as indicated herein above.

When calculating the rate of change, one may use any two samples collected at different time points from the patient. To ensure more reliable results and reduce statistical deviations to a minimum, averaging the calculated rates of several sample pairs is preferable. A calculated or average negative rate of change of the normalized expression values of CD247 indicates that the subject is in a chronic inflammation state in response to said treatment.

As indicated above, in order to execute the diagnostic and prognostic method of the invention, at least two different samples, and preferably, more than two, must be obtained, from the subject in order to calculate the rate of change in the expression of CD247 in response to treatment with a specific compound. By obtaining at least two and preferably more biological samples from a subject and analyzing them according to the method of the invention, may be effective for predicting, monitoring and early diagnosing molecular alterations indicating a chronic inflammation state in said patient in response to said treatment. Thus, the prognostic method of the invention may be applicable for early, sub-symptomatic diagnosis of chronic inflammation in a treated subject, when used for analysis of more than a single sample along the time-course of diagnosis, treatment and follow-up. An "early diagnosis" provides diagnosis prior to appearance of clinical symptoms. Prior as used herein is meant days, weeks, months or even years before the appearance of such symptoms. More specifically, at least 1 week, at least 1 month, 2 months, 3 months, 4 months, 5 months, 6 months, 7 months, 8 months, 9 months, 10 months, 11 months, 12 months, or even few years before clinical symptoms appear.

Simply put, a decline in the expression of CD247 indicates a chronic inflammation associated with immunosuppression that is a result of non-responsiveness reflecting failure of a treatment and may provide an early sign before over symptoms occur, allowing for a quicker and more efficient therapeutic response.

More specifically, the invention therefore further provides a prognostic method. Prognosis is defined as a forecast of the future course of a disease or disorder, based on medical knowledge. This highlights the major advantage of the instant invention over prior art, namely, the ability to predict chronic inflammation indicating regression or recurrence of the diseases in patients treated with a non appropriate therapeutic agent. This early prognosis facilitates the selection of appropriate treatment regimens that may minimize the regression or recurrence of the diseases, individually to each patient, as part of personalized medicine.

As disclosed herein above, the invention thus provides a method for predicting the efficacy and suitability of a specific treatment.

As used herein the phrase "predicting or evaluating efficacy of a treatment" refers to determining the likelihood that a specific treatment using a therapeutic agent is efficient or non-efficient in treating the chronic inflammatory condition, e.g., the success or failure of the treatment in treating the chronic inflammatory condition in a subject in need thereof. More specifically, a treatment with a therapeutic agent that directly, as an anti-inflammatory agent, or indirectly (a chemotherapeutic or biological agent) affects inflammation. The term "efficacy" as used herein refers to the extent to which the anti-inflammatory treatment produces a beneficial result, e.g., an improvement in one or more symptoms of the pathology (caused by the chronic inflammatory condition) and/or clinical parameters related to the pathology as described herein below. For example, the efficacy of an anti-inflammatory treatment may be evaluated using standard therapeutic indices for chronic inflammatory condition, for example, a proliferative disorder, an autoimmune disease or an infectious disease).

According to some embodiments of the invention, the efficacy of treatment is a long-term efficacy. As used herein the phrase "long-term efficacy" refers to the ability of a treatment to maintain a beneficial result over a period of time, e.g., at least about 16 weeks, at least about 26 weeks, at least about 32 weeks, at least about 36 weeks, at least about 40 weeks, at least about 48 weeks, at least about 52 weeks, at least about 18 months, at least about 24 months, at least about 3 years, at least about 4 years, at least about 5 years, at least about 6 years, at least about 7 years, at least about 8 years, at least about 9 years, at least about 10 years, or longer.

According to some embodiments of the invention, a treatment with a therapeutic agent that either directly or indirectly affects inflammation, is considered efficient in treating a chronic inflammatory condition if it exerts an improvement in at least one relevant clinical parameter related to said condition in the treated subject as compared to an untreated subject diagnosed with the same condition (e.g., where the chronic inflammatory condition is cancer, such parameter include the type, stage, degree and/or classification of the solid tumor), or as compared to the clinical parameters related to the said condition of the same subject prior to the anti-inflammatory treatment.

A "positive clinical outcome" and "beneficial response" can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition of metastasis; (6) enhancement of anti-tumor immune response, possibly resulting in regression or rejection of the tumor; (7) relief, to some extent, of one or more symptoms associated with the tumor; (8) increase in the length of survival following treatment; and/or (9) decreased mortality at a given point of time following treatment. Positive clinical response may also be expressed in terms of various measures of clinical outcome. Positive clinical outcome can also be considered in the context of an individual's outcome relative to an outcome of a population of patients having a comparable clinical diagnosis, and can be assessed using various endpoints such as an increase in the duration of Recurrence-Free interval (RFI), an increase in the time of survival as compared to Overall Survival (OS) in a population, an increase in the time of Disease-Free Survival (DFS), an increase in the duration of Distant Recurrence-Free Interval (DRFI), and the like. An increase in the likelihood of positive clinical response corresponds to a decrease in the likelihood of cancer recurrence.

Still further, the invention provides a prognostic tool for detecting responders vs. non-responders to a given immune-based therapy.

The method of the invention is applicable for determining the suitability and efficacy of a specific therapeutic agent or combinations of agents. However, it must be also recognized that the method of the invention may further provide information regarding the overall treatment regimen. More specifically, by sensing changes in the inflammatory state as reflected by changes in the expression levels of CD247, the invention may enable defining (or fine tuning) the optimal concentrations of the therapeutic agent and providing information regarding the preferable duration of treatment. As demonstrated by FIG. 20, the use high concentration of the 5FU+CPT11, resulted in a harmful effect, however, when low doses of the same combination were applied, this combination displayed a beneficial effect.

As indicated above, the method of the invention is based on determining the expression of the biomarker CD247 in a sample. In yet further specific embodiments of the invention, the determination of the level of expression of CD247 in a biological sample of the tested subject may be performed by a method comprising the step of contacting detecting molecules specific for CD247 with a biological sample of said subject, or with any nucleic acid or protein product obtained there from. More specifically, the method of invention relies on the detection of CD247 by contacting detecting molecules specific for CD247 with a biological sample. The term "contacting" means to bring, put, incubate or mix together. As such, a first item is contacted with a second item when the two items are brought or put together, e.g., by touching them to each other or combining them. In the context of the present invention, the term "contacting" includes all measures or steps, which allow interaction between at least one detecting molecule specific for CD247 and the tested sample, or any component derived therefrom. In certain embodiments where reference controls are also used, the method of the invention further involves contacting steps, which allow interaction between at least one detecting molecule specific for a suitable reference control and the tested sample or any component derived therefrom. The contacting is performed in a manner by which the at least one of detecting molecule of CD247 and at least one suitable reference control can interact with or bind to the peptide molecules or nucleic acid molecule in the tested sample. The binding will preferably be non-covalent, reversible binding, e.g., binding via salt bridges, hydrogen bonds, hydrophobic interactions or a combination thereof.

According to certain and specific embodiments, the method of the invention may further comprise an additional and optional step of normalization. According to this embodiment, after determination of the expression levels of CD247, the expression levels of a reference control are also determined, and subsequently, the expression levels of CD247 may be normalized according to the expression value of said at least one reference control, in the same test sample. Optionally, similar normalization is performed also relative to a control sample or a representing standard when applicable. According to this particular embodiment, a normalized expression value of CD247 in the test sample, and optionally relative to a control sample is obtained. The next step in this embodiment, involves comparing the normalized CD247 expression value in the test biological sample obtained in this additional step, with a predetermined standard expression value, or a cutoff value, or with a normalized expression value of CD247 in a control sample optionally obtained in this additional step. It should be noted that in certain embodiments, a "negative" that is a lower expression value (or rate of change) of CD247 in the tested sample, as compared to a predetermined standard expression value (cutoff) or to the expression value of CD247 in a control sample, in response to treatment with a therapeutic agent is indicative of an unsuccessful treatment that leads to, increase or does not improve a chronic inflammation and associated immune-suppression in the tested subject.

As mentioned above, the optional normalization step of the method of the invention involves normalization of the measured expression values of CD247, to obtain normalized expression value. As indicated herein, the measured levels of expression of CD247 are routinely normalized using data of expression levels of the control reference proteins. In general scientific context, normalization is a process by which a measurement raw data is converted into data that may be directly compared with other so normalized data. In the context of the present invention, measurements of marker genes or proteins, specifically, CD247, expression levels are prone to errors caused by, for example, unequal degradation of measured samples, different loaded quantities per assay, and other various errors. More specifically, any assayed sample may contain more or less biological material than is intended, due to human error and equipment failures. Thus, the same error or deviation applies to both the biomarker of the invention and to the control reference, whose expression is essentially constant. Thus, division of the CD247 raw expression value by the control reference raw expression value yields a quotient, which is essentially free from any technical failures or inaccuracies (except for major errors which destroy the sample for testing purposes) and constitutes a normalized expression value of said biomarker. This normalized expression value may then be compared with normalized cutoff values, i.e., cutoff values calculated from normalized expression values. Since control reference expression values are equal in different samples, they constitute a common reference point that is valid for such normalization.

More specifically, in the present case, the expression of control references used by the invention, i.e., CD3ε (for T cells) is equal and stable in samples displaying chronic inflammation in response to a certain therapeutic agent and in control samples of healthy donors or responsive subjects that do not display chronic inflammation and therefore exhibit a beneficial effect of the treatment. In certain embodiments, other control references may be used, for example, any one of CD56 or SNX27.

Thus, in certain specific embodiments, method of the invention may further comprise the use of reference control. According to such embodiments, the method further involves contacting the biological sample or any protein or nucleic acid product obtained therefrom with detecting molecules specific for at least one reference control.

According to certain embodiments, the reference control protein used by the methods of the invention displays constant expression pattern in a sample of an un-treated subject that suffers from a chronic inflammatory condition, a treated subject exhibiting a beneficial response (also referred to herein as a "responder"), a subject that exhibits a deleterious response to the same therapeutic agent, as well as healthy subjects. As shown by the following Examples, the expression of CD3ε is similar in samples displaying chronic inflammation in response to treatment and in samples taken from responder subjects displaying a non-inflammatory state. Therefore, in a specific embodiment, CD3ε is used as a control reference (specifically, for T cells). In more specific embodiments, such reference control may be at least one of CD3ε, CD3δ, CD3γ, TCRα, TCRβ, CD56 and in some embodiments also TCR γ and TCR δ.

It should be appreciated that determination of the level of CD247 expression in the biological sample can be effected at the transcriptional level (i.e., mRNA) using detecting molecules that are based on nucleic acids (an oligonucleotide probe or primer), or alternatively, at the translational level (i.e. protein) using amino acid based detecting molecules, as also demonstrated by the present invention. Thus, according to one specific embodiment, the detecting molecules used by the method of the invention may be isolated detecting amino acid molecules or isolated detecting nucleic acid molecules, or any combinations thereof.

According to one specific embodiment, the detection of CD247 expression can be affected at the protein level.

Therefore, the detecting molecules used by the method of the invention may be amino acid molecules, specifically, an isolated antibodies that specifically recognize and binds CD247. As shown by the following Examples, the anti-CD247 antibodies used by the method of the invention are antibodies specifically directed to the C' terminal domain of the CD247 molecule. However, it should be noted that according to certain embodiments, antibodies directed to any part or fragment of CD247 molecule may be used for performing the invention.

As indicated above, the detecting molecules of the invention may be amino acid based molecules that may be referred to as protein/s or polypeptide/s. As used herein, the terms "protein" and "polypeptide" are used interchangeably to refer to a chain of amino acids linked together by peptide bonds. In a specific embodiment, a protein is composed of less than 200, less than 175, less than 150, less than 125, less than 100, less than 50, less than 45, less than 40, less than 35, less than 30, less than 25, less than 20, less than 15, less than 10, or less than 5 amino acids linked together by peptide bonds. In another embodiment, a protein is composed of at least 200, at least 250, at least 300, at least 350, at least 400, at least 450, at least 500 or more amino acids linked together by peptide bonds. It should be noted that peptide bond as described herein is a covalent amid bond formed between two amino acid residues.

The invention further contemplates the use of amino acid based molecules such as proteins or polypeptides as detecting molecules disclosed herein and would be known by a person skilled in the art to measure the protein marker of the invention, CD247. Techniques known to persons skilled in the art (for example, techniques such as Western Blotting, Immunoprecipitation, ELISAs, protein microarray analysis, Flow cytometry and the like) can then be used to measure the level of protein products corresponding to the biomarker of the invention. As would be understood to a person skilled in the art, the measure of the level of expression of the protein products of the biomarker of the invention, specifically, CD247 requires a protein, which specifically and/or selectively binds to the biomarker of the invention.

In specific embodiments, the detecting amino acid molecules are isolated antibodies, with specific binding selectively to CD247. Using these antibodies, the level of expression of CD247 may be determined using an immunoassay which is selected from the group consisting of FACS, a Western blot, an ELISA, a RIA, a slot blot, a dot blot, immunohistochemical assay, immunofluorescent assay and a radio-imaging assay.

The term "antibody" as used in this invention includes whole antibody molecules as well as functional fragments thereof, such as Fab, F(ab')2, and Fv that are capable of binding with antigenic portions of the target polypeptide, i.e. CD247. The antibody is preferably monospecific, e.g., a monoclonal antibody, or antigen-binding fragment thereof. The term "monospecific antibody" refers to an antibody that displays a single binding specificity and affinity for a particular target, e.g., epitope. This term includes a "monoclonal antibody" or "monoclonal antibody composition", which as used herein refer to a preparation of antibodies or fragments thereof of single molecular composition.

It should be recognized that the antibody can be a human antibody, a chimeric antibody, a recombinant antibody, a humanized antibody, a monoclonal antibody, or a polyclonal antibody. The antibody can be an intact immuno globulin, e.g., an IgA, IgG, IgE, IgD, 1 gM or subtypes thereof. The antibody can be conjugated to a functional moiety (e.g., a compound which has a biological or chemical function. The antibody used by the invention interacts with a polypeptide that is CD247, with high affinity and specificity.

As noted above, the term "antibody" also encompasses antigen-binding fragments of an antibody. The term "antigen-binding fragment" of an antibody (or simply "antibody portion," or "fragment"), as used herein, may be defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab')2 is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA", or ScFv), a genetically engineered molecule containing the variable region of the light chain and the variable region of the heavy chain, linked by a suitable polypeptide linker as a genetically fused single chain molecule.

Methods of generating such antibody fragments are well known in the art (See for example, Harlow and Lane, Antibodies: A Laboratory Manual, Cold Spring Harbor Laboratory, New York, 1988, incorporated herein by reference).

Purification of serum immunoglobulin antibodies (polyclonal antisera) or reactive portions thereof can be accomplished by a variety of methods known to those of skill in the art including, precipitation by ammonium sulfate or sodium sulfate followed by dialysis against saline, ion exchange chromatography, affinity or immuno-affinity chromatography as well as gel filtration, zone electrophoresis, etc.

Still further, for determination and monitoring uses described herein after, the anti-CD247 antibodies used by the present invention may optionally be covalently or non-covalently linked to a detectable label. The term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody. More specifically, detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^3$H, $^{125}$I, $^{35}$S, $^{14}$C, or $^{32}$P), enzymes (e.g., horseradish peroxidase, alkaline phosphatase and others commonly used in an ELISA and competitive ELISA and other similar methods known in the art) and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The antibody used as a detecting molecule according to the invention, specifically recognizes and binds CD247. It should be therefore noted that the term "binding specificity", "specifically binds to an antigen", "specifically immunoreactive with", "specifically directed against" or "specifically recognizes", when referring to an epitope, specifically, a recognized epitope within the CD247 molecule, refers to a binding reaction which is determinative of the presence of the epitope in a heterogeneous population of proteins and other biologics. More particularly, "selectively bind" in the context of proteins encompassed by the invention refers to the specific interaction of a any two of a peptide, a protein, a polypeptide an antibody, wherein the interaction preferentially occurs as between any two of a peptide, protein, polypeptide and antibody preferentially as compared with any other peptide, protein, polypeptide and antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

Thus, under designated immunoassay conditions, the specified antibodies bind to a particular epitope at least two times the background and more typically more than 10 to 100 times background. More specifically, "Selective binding", as the term is used herein, means that a molecule binds its specific binding partner with at least 2-fold greater affinity, and preferably at least 10-fold, 20-fold, 50-fold, 100-fold or higher affinity than it binds a non-specific molecule.

A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate.

According to one embodiment, where amino acid-based detection molecules are used, the expression level of the CD247 protein, in the tested sample can be determined using different methods known in the art, specifically method disclosed herein below as non-limiting examples.

Enzyme-Linked Immunosorbant Assay (ELISA)

This method involves fixation of a sample containing a protein substrate (e.g., fixed cells or a proteinaceous solution) to a surface such as a well of a microtiter plate. A substrate-specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot

This method involves separation of a substrate from other protein by means of an acrylamide gel followed by transfer of the substrate to a membrane (e.g., nitrocellulose, nylon, or PVDF). Presence of the substrate is then detected by antibodies specific to the substrate, which are in turn detected by antibody-binding reagents. Antibody-binding reagents may be, for example, protein A or secondary antibodies. Antibody-binding reagents may be radiolabeled or enzyme-linked, as described hereinafter. Detection may be by autoradiography, colorimetric reaction, or chemiluminescence. This method allows both quantitation of an amount of substrate and determination of its identity by a relative position on the membrane indicative of the protein's migration distance in the acrylamide gel during electrophoresis, resulting from the size and other characteristics of the protein.

Radioimmunoassay (RIA)

In one version, this method involves precipitation of the desired protein (i.e., the substrate) with a specific antibody and radiolabeled antibody-binding protein (e.g., protein A labeled with $I^{125}$) immobilized on a precipitable carrier such as agarose beads. The radio-signal detected in the precipitated pellet is proportional to the amount of substrate bound.

In an alternate version of RIA, a labeled substrate and an unlabelled antibody-binding protein are employed. A sample containing an unknown amount of substrate is added in varying amounts. The number of radio counts from the labeled substrate-bound precipitated pellet is proportional to the amount of substrate in the added sample.

Fluorescence-Activated Cell Sorting (FACS)

This method involves detection of a substrate in situ in cells bound by substrate-specific, fluorescently labeled antibodies. The substrate-specific antibodies are linked to fluorophores. Detection is by means of a flow cytometry machine, which reads the wavelength of light emitted from each cell as it passes through a light beam. This method may employ two or more antibodies simultaneously, and is a reliable and reproducible procedure used by the present invention.

Immunohistochemical Analysis

This method involves detection of a substrate in situ in fixed cells by substrate-specific antibodies. The substrate specific antibodies may be enzyme-linked or linked to fluorophores. Detection is by microscopy, and is either subjective or by automatic evaluation. With enzyme-linked antibodies, a calorimetric reaction may be required. It will be appreciated that immunohistochemistry is often followed by counterstaining of the cell nuclei, using, for example, Hematoxyline or Giemsa stain.

According to certain alternative embodiments, the detecting molecules for CD247 expression may be isolated detecting nucleic acid molecules. According to some embodiments, such detecting nucleic acid molecules may be isolated oligonucleotides, each oligonucleotide specifically hybridizes to a nucleic acid sequence of the RNA products of said CD247. More specifically, the oligonucleotide used as a detecting molecule according to certain embodiments of the invention may be any one of a pair of primers or nucleotide probe. In such case, the level of expression of CD247 may be determined using a nucleic acid amplification assay selected from the group consisting of: a Real-Time PCR, micro arrays, PCR, in situ Hybridization and Comparative Genomic Hybridization. It should be noted that in particular embodiments, the invention further encompasses the use of aptamers as a nucleic acid based detection molecules that specifically recognize and bind the CD247 protein.

As used herein, "nucleic acids" is interchangeable with the term "polynucleotide(s)" and it generally refers to any polyribonucleotide or poly-deoxyribonucleotide, which may be unmodified RNA or DNA or modified RNA or DNA or any combination thereof. "Nucleic acids" include, without limitation, single- and double-stranded nucleic acids. As used herein, the term "nucleic acid(s)" also includes DNAs or RNAs as described above that contain one or more modified bases.

As used herein, the term "oligonucleotide" is defined as a molecule comprised of two or more deoxyribonucleotides and/or ribonucleotides, and preferably more than three. Its exact size will depend upon many factors which in turn, depend upon the ultimate function and use of the oligonucleotide. The oligonucleotides may be from about 8 to about 1,000 nucleotides long. More specifically, the detecting oligonucleotides molecule used by the composition of the invention may comprise any one of 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 bases in length.

According to another alternative embodiment, where nucleic acid-based detection molecules are used, the expression level of the CD247 RNA product, in the tested sample can be determined using methods known in the art. Different methods of determining levels of the expression of the biomarker of the invention, CD247 (i.e., RNA or protein) in biological samples using nucleic acid base detection methods may be applicable for performing the method of the invention. Such procedures include, but are not limited to, Northern Blot Analysis, Polymerase chain reaction (PCR)-based methods (e.g., RT-PCR, using oligonucleotide primers or probes as the detection molecules), RNA In Situ Hybridization Stain, In Situ RT-PCR Stain, and Oligonucleotide Microarray procedures (for example, the Affymetrix® GeneChip® Microarray), It should be appreciated that all the detecting molecules (either nucleic acid based or amino acid based) used by the methods, compositions and kits (compositions and kits will be described herein after) of the invention are isolated and/or purified molecules. As used herein, "isolated" or "purified" when used in reference to a nucleic acid means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95% pure) of non-nucleotide material naturally associated with it, and thus is distinguished from isolated chromosomes. As used herein, the terms "isolated" and "purified" in the context of a proteinaceous agent (e.g., a peptide, polypeptide, protein or antibody) refer to a proteinaceous agent which is substantially free of cellular material and in some embodiments, substantially free of heterologous proteinaceous agents (i.e. contaminating proteins) from the cell or tissue source from which it is derived, or substantially free of chemical precursors or other chemicals when chemically synthesized. The language "substantially free of cellular material" includes preparations of a proteinaceous agent in which the proteinaceous agent is separated from cellular components of the cells from which it is isolated or recombinantly produced. Thus, a proteinaceous agent that is substantially free of cellular material includes preparations of a proteinaceous agent having less than about 30%, 20%, 10%, or 5% (by dry weight) of heterologous proteinaceous agent (e.g. protein, polypeptide, peptide, or antibody; also referred to as a "contaminating protein"). When the proteinaceous agent is recombinantly produced, it is also preferably substantially free of culture medium, i.e. culture medium represents less than about 20%, 10%, or 5% of the volume of the protein preparation. When the proteinaceous agent is produced by chemical synthesis, it is preferably substantially free of chemical precursors or other chemicals, i.e., it is separated from chemical precursors or other chemicals which are involved in the synthesis of the proteinaceous agent. Accordingly, such preparations of a proteinaceous agent have less than about 30%, 20%, 10%, 5% (by dry weight) of chemical precursors or compounds other than the proteinaceous agent of interest. Preferably, proteinaceous agents disclosed herein are isolated.

As showed by the following Examples, the correlation of increased expression of CD247 with a beneficial effect of the examined therapeutic agent was further examined and established by examining other parameters involved with chronic inflammation. More specifically, increased population of myeloid derived suppressor cells (MDSCs), increase in NO and ROS, increased levels of S100A8, S100A9 proteins and reduced levels of cleaved caspase 3 are correlated with changes in the inflammatory environment. Although the expression of CD247 seemed to be a more accurate and sensitive marker, the combination of several markers may increase sensitivity and specificity. Thus, in yet additional particular embodiments, the method of the invention may further combine other markers and therefore comprise the step of at least one of:

(a) determining myeloid-derived suppressor cells (MDSCs) population in a biological sample of the examined subject;

(b) determining the expression levels of S100A8 and/or S100A9 proteins in the sample. As shown by FIG. 17, examination of the expression of S100A8/9 at the protein level seemed more accurate in reflecting the inflammatory state. It should be therefore noted that in certain embodiments, the level of S100A8 or S100A9 may be determined at the protein level.

(c) determining the levels of cleaved caspase 3 in said sample; and (d) determining at least one of intracellular nitric oxide (NO) and reactive oxygen species (ROS) production in said sample. Further parameters may include examining the proliferation capacity of T cells upon TCR-mediated activation as well as measuring the killing capacity of NK cells.

In more specific embodiments, wherein at least one of an enlarged population of MDSC cells, increase in the level of S100A8 and/or S100A9, reduced cleaved caspase 3 and elevated ROS and NO as compared to a predetermined cut-off value, indicates that the therapeutic agent leads to elevation in the inflammatory state of the treated subject and is therefore not effective and inappropriate for use.

The method of the invention is specifically applicable for determining the efficacy or suitability of a specific therapeutic agent for treating a chronic inflammatory condition, or generally, an immune-related disorder. It should be noted that an "Immune-related disorder" is a condition that is associated with the immune system of a subject, either through activation or inhibition of the immune system, or that can be treated, prevented or diagnosed by targeting a certain component of the immune response in a subject, such as the adaptive or innate immune response. It should be noted that the method of the invention provides determining the efficacy of treatment with a specific therapeutic agent on a subject suffering from any pathologic condition that may directly or indirectly lead to a chronic inflammatory condition, specifically to a systemic chronic inflammatory condition (and not only to a local inflammation). In specific embodiments, such disorder may be a proliferative disorder, a chronic inflammatory condition, specifically, any one of an inflammatory disease, viral infections, an autoimmune disease, metabolic disorders and cancer.

According to one specific embodiment, the method of the invention may be specifically suitable for determining the efficacy of a specific therapeutic agent for treating an inflammatory disease or an inflammatory-associated condition that may be caused by any pathological disorder. The terms "inflammatory disease" or "inflammatory-associated condition" refers to any disease or pathologically condition which can benefit from the reduction of at least one inflammatory parameter, for example, induction of an inflammatory cytokine such as IFN-gamma, TNF$\alpha$, IL1$\beta$, IL-6 and IL-2. The condition may be caused (primarily) from inflammation, or inflammation may be one of the manifestations of the diseases caused by another physiological cause.

It is understood that the interchangeably used terms "associated", "linked" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology. More specifically, as used herein, "disease", "disorder", "condition", "pathology" and the like, as they relate to a subject's health, are used interchangeably and have meanings ascribed to each and all of such terms.

As noted above, the present invention provides a powerful tool for determining the suitability for treatment of a patient suffering from a disease associated with a chronic inflammatory condition. Such condition may be any one of a proliferative disorder, an autoimmune disease and an infectious disease. Thus, according to some embodiments, the method of the invention may be applicable for chronic inflammatory condition that may be a proliferative disorder, an autoimmune disorder, an infectious disease, metabolic disorders and cancer.

More specifically, chronic inflammatory state, as used herein is reflected by an inflammatory response. As used herein the phrase "inflammatory response" refers to an immune response which results in either chronic or acute inflammation, typically occurring as a result of injurious stimuli including infection, burns, trauma, neoplasia, autoimmune signals and exposure to chemicals, heat or cold or any other harmful stimulus. An inflammatory response according to the present invention refers to a chronic inflammation.

According to further embodiments, the method of the invention may be used for determining the suitability of a certain therapeutic agent, specifically, a chemotherapeutic agent, biological agent or immuno-therapeutic agent, for treatment of a patient suffering from a chronic inflammatory condition that may be a proliferative disorder. According to more specific embodiments, the method of the invention may be specifically efficient for a proliferative disorder.

As used herein to describe the present invention, "proliferative disorder", "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the methods of the present invention may be applicable for determining the suitability for treatment of a patient suffering from any one of non-solid and solid tumors.

Malignancy, as contemplated in the present invention may be any one of carcinomas, melanomas, lymphomas, leukemias, myeloma and sarcomas.

Carcinoma as used herein, and will be described in more detail herein after in connection with colorectal carcinoma (CRC), refers to an invasive malignant tumor consisting of transformed epithelial cells. Alternatively, it refers to a malignant tumor composed of transformed cells of unknown histogenesis, but which possess specific molecular or histological characteristics that are associated with epithelial cells, such as the production of cytokeratins or intercellular bridges.

Melanoma as used herein, is a malignant tumor of melanocytes. Melanocytes are cells that produce the dark pigment, melanin, which is responsible for the color of skin. They predominantly occur in skin, but are also found in other parts of the body, including the bowel and the eye. Melanoma can occur in any part of the body that contains melanocytes.

Leukemia refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (sublcukemic).

Sarcoma is a cancer that arises from transformed connective tissue cells. These cells originate from embryonic mesoderm, or middle layer, which forms the bone, cartilage, and fat tissues. This is in contrast to carcinomas, which originate in the epithelium. The epithelium lines the surface of structures throughout the body, and is the origin of cancers in the breast, colon, and pancreas.

Myeloma as mentioned herein is a cancer of plasma cells, a type of white blood cell normally responsible for the production of antibodies. Collections of abnormal cells accumulate in bones, where they cause bone lesions, and in the bone marrow where they interfere with the production of normal blood cells. Most cases of myeloma also feature the production of a paraprotein, an abnormal antibody that can cause kidney problems and interferes with the production of normal antibodies leading to immunodeficiency. Hypercalcemia (high calcium levels) is often encountered.

Lymphoma is a cancer in the lymphatic cells of the immune system. Typically, lymphomas present as a solid tumor of lymphoid cells. These malignant cells often originate in lymph nodes, presenting as an enlargement of the node (a tumor). It can also affect other organs in which case it is referred to as extranodal lymphoma. Non limiting examples for lymphoma include Hodgkin's disease, non-Hodgkin's lymphomas and Burkitt's lymphoma.

Further malignancies that may find utility in the present invention can comprise but are not limited to hematological malignancies (including lymphoma, leukemia and myeloproliferative disorders, as described above), hypoplastic and aplastic anemia (both virally induced and idiopathic), myelodysplastic syndromes, all types of paraneoplastic syndromes (both immune mediated and idiopathic) and solid tumors (including GI tract, colon, lung, liver, breast, prostate, pancreas and Kaposi's sarcoma. The invention may be applicable as well for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

As clearly disclosed by Example 9, the method of the invention may be applicable in determining the efficacy and suitability of using different chemotherapeutic agents, and combinations thereof for treating colorectal cancer.

Colon cancer (also referred to herein as "colorectal cancer or carcinoma") as herein defined is a disease in which malignant (cancer) cells form in the tissues of the colon (part of the body's digestive system). Colorectal carcinoma is the third most common cancer in the United States after prostate and lung/bronchus cancers in men and after breast and lung/bronchus cancers in women. It is also the third leading cause of cancer-related death in the United States. In 2011, an estimated 141,210 new cases of colorectal carcinoma were diagnosed in United States, with an estimated 49,380 deaths.

Risk factors of colon cancer include age and health history, a family history of colon cancer, and in some cases having inflammatory bowel disease (IBD). The results of different studies vary, but in general, the risk of colon cancer for people with IBD increases by 0.5% to 1% yearly approximately 8 to 10 years after diagnosis. Other studies have shown that people with IBD are five times more likely to develop colon cancer than the general public.

The prognosis of patients with colon cancer is clearly related to the degree of penetration of the tumor through the bowel wall, the presence or absence of nodal involvement, and the presence or absence of distant metastases, with these three characteristics forming the basis for all staging systems developed for this disease.

Many other prognostic markers have been evaluated retrospectively for patients with colon cancer, though most, including allelic loss of chromosome 18q or thymidylate synthase expression, have not been prospectively validated.

Since the 1960s, 5-fluorouracil (5-FU) has remained the mainstay of therapeutic options in the treatment of advanced CRC, with the introduction of newer agents such as oxaliplatin and irinotecan (CPT11) in combination with 5-FU increasing the response rates. In addition, the development of immuno-therapeutic agents, for example, monoclonal antibodies targeting the epidermal growth factor receptor or vascular endothelial growth factor has demonstrated additional clinical benefit for patients with metastatic disease. The main monoclonal antibodies that are used for the treatment of colon cancer include bevacizumab (also known as Avastin), cetuximab (also known as Erbitux) and panitumumab (also known as Vectibix).

However, many patients yield to their disease, and a significant proportion will experience severe chemotherapy associated toxicities while deriving little or no benefit from the treatment. In order to improve the treatment of CRC, efforts must be directed toward the identification of patients who are likely to respond to a specific therapy, those who will experience severe toxicities, and those who will benefit from chemotherapy in the adjuvant setting. The Examples section herein below discloses an example for evaluating the suitability of treatment using these chemotherapeutic agents and combinations thereof. The present invention therefore demonstrates the feasibility of using CD247 as a biomarker for the purpose of personalized medicine, providing efficient examination and evaluation of the suitability and efficacy of a certain chemotherapeutic agent for use in the treatment of a proliferative disorder. Thereby, the invention addresses the need for such personalized appropriate and optimal treatment regimen for a specific patient.

In yet other embodiments, the method of the invention may be used for determining the appropriate treatment regimen for any type of colorectal cancer (CRC). Different types of colorectal cancers. More specifically, collectively, colon cancer is defined as a cancer that forms in the tissues of the colon (the longest part of the large intestine). These tumors are sometimes referred to as "colorectal" cancer, reflecting the fact that the rectum, the end portion of the colon, may also be affected.

More than 90% of colorectal carcinomas are adenocarcinomas, originating from epithelial cells of the colorectal mucosa. Other rare types of colorectal carcinomas include neuroendocrine, squamous cell, adenosquamous, spindle cell and undifferentiated carcinomas. Conventional adenocarcinoma is characterized by glandular formation, which is the basis for histologic tumor grading.

Most colon cancers occurs due to lifestyle and increasing age with only a minority of cases associated with underlying genetic disorders. It typically starts in the lining of the bowel and if left untreated, can grow into the muscle layers underneath, and then through the bowel wall.

According to some embodiments, the method of the invention may be used for determining the suitability for a specific treatment of a patient suffering from any autoimmune disease such as for example, but not limited to, inflammatory bowel disease (IBD), ulcerative colitis and Crohn's disease and fatty liver disease, rheumatoid arthritis, systemic lupus erythematosus (SLE), Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM) and NIDDM, multiple sclerosis (MS), myasthenia gravis, plexus disorders e.g. acute brachial neuritis, polyglandular deficiency syndrome, primary biliary cirrhosis, scleroderma, thrombocytopenia, thyroiditis e.g. Hashimoto's disease, Sjogren's syndrome, allergic purpura, psoriasis, mixed connective tissue disease, polymyositis, dermatomyositis, vasculitis, polyarteritis nodosa, arthritis, alopecia areata, polymyalgia rheumatica, Wegener's granulomatosis, Reiter's syndrome, Behget's syndrome, ankylosing spondylitis, pemphigus, bullous pemphigoid, dermatitis herpetiformis.

In yet other specific embodiments the method of the invention may be also applicable for determining the suitability for treatment of a patient suffering from inflammatory bowel diseases (IBD). Inflammatory bowel diseases are common gastrointestinal disorders, that can be perceived as being the result of a dysbalance between Th1-pro-inflammatory and Th2-anti-inflammatory subtypes of immune responses. IBD is a group of inflammatory conditions of the colon and small intestine. The major types of IBD are Crohn's disease and ulcerative colitis (UC) that share the same symptoms such as diarrhea, vomiting, weight loss, fever and abdominal pain. Other forms of IBD account for far fewer cases. These are Collagenous colitis, Lymphocytic colitis, Ischaemic colitis, Diversion colitis, Behçet's syndrome and Indeterminate colitis which is an inability to make a definitive diagnosis distinguishing Crohn's disease from Ulcerative colitis.

According to another specific embodiment, the method of the invention may be used in determining the suitability for treatment of a patient suffering from rheumatoid arthritis. Rheumatoid arthritis (RA) is a chronic, systemic autoimmune disorder that most commonly causes inflammation and tissue damage in joints (arthritis) and tendon sheaths, together with anemia. It can also produce diffuse inflammation in the lungs, pericardium, pleura, and the sclera of the eye, and also nodular lesions, most common in subcutaneous tissue. It can be a disabling and painful condition, which can lead to substantial loss of functioning and mobility.

According to another embodiment, the method of the invention may be used in determining the suitability for treatment of a patient suffering from a disease defined within the seronegative spondyloarthropathy category, which includes psoriatic arthritis, reactive arthritis, and ankylosing spondylitis, and is characterized by signs of inflammation, multiple joint involvement, and distal involvement in the hands and feet with added features of bone proliferation.

It should be appreciated that there are many other forms of inflammatory arthritis, including juvenile idiopathic arthritis, gout and pseudo gout, as well as arthritis associated with colitis or psoriasis. It should be therefore appreciated that the method of the invention are also applicable for these conditions as well.

In yet other embodiments, the method of the invention may be also applicable for determining the suitability of a specific therapeutic agent for treating a subject suffering from an infectious disease. More specifically, such infectious disease may be any one of protozoan diseases, viral diseases, bacterial diseases, parasitic diseases, fungal diseases and *mycoplasma* diseases. Therefore, specific embodiments of the invention relate to the use of the method of the invention for determining the suitability for treatment of a patient suffering from infectious diseases.

It should be appreciated that an infectious disease as used herein also encompasses any infectious disease caused by a pathogenic agent. Pathogenic agents include prokaryotic microorganisms, lower eukaryotic microorganisms, complex eukaryotic organisms, viruses, fungi, prions, parasites, yeasts, toxins and venoms.

A prokaryotic microorganism includes bacteria such as Gram positive, Gram negative and Gram variable bacteria and intracellular bacteria. Examples of bacteria contemplated herein include the species of the genera *Treponema* sp., *Borrelia* sp., *Neisseria* sp., *Legionella* sp., *Bordetella* sp., *Escherichia* sp., *Salmonella* sp., *Shigella* sp., *Klebsiella* sp., *Yersinia* sp., *Vibrio* sp., *Hemophilus* sp., *Rickettsia* sp., *Chlamydia* sp., *Mycoplasma* sp., *Staphylococcus* sp., *Streptococcus* sp., *Bacillus* sp., *Clostridium* sp., *Corynebacterium* sp., *Proprionibacterium* sp., *Mycobacterium* sp., *Ureaplasma* sp. and *Listeria* sp.

A lower eukaryotic organism includes a yeast or fungus such as but not limited to *Pneumocystis carinii, Candida albicans, Aspergillus, Histoplasma capsulatum, Blastomyces dermatitidis, Cryptococcus neoformans, Trichophyton* and *Microsporum*.

A complex eukaryotic organism includes worms, insects, arachnids, nematodes, aemobe, *Entamoeba histolytica, Giardia lamblia, Trichomonas vaginalis, Trypanosoma brucei gambiense, Trypanosoma cruzi, Balantidium coli, Toxoplasma gondii, Cryptosporidium* or *Leishmania*.

The term "viruses" is used in its broadest sense to include viruses of the families adenoviruses, papovaviruses, herpesviruses: simplex, varicella-zoster, Epstein-Barr, CMV, pox viruses: smallpox, vaccinia, hepatitis B, rhinoviruses, hepatitis A, poliovirus, rubella virus, hepatitis C, arboviruses, rabies virus, influenza viruses A and B, measles virus, mumps virus, HIV, HTLV I and II.

The term "fungi" includes for example, fungi that cause diseases such as ringworm, histoplasmosis, blastomycosis, aspergillosis, cryptococcosis, sporotricho sis, coccidioidomycosis, paracoccidio-idoinycosis, and candidiasis.

The term parasite includes, but not limited to, infections caused by somatic tapeworms, blood flukes, tissue roundworms, ameba, and *Plasmodium, Trypanosoma, Leishmania*, and *Toxoplasma* species.

As noted before, The following Examples demonstrate the evaluation of different chemotherapeutic agents for treating chronic inflammatory conditions. The term "chemotherapeutic agent" or "chemotherapeutic drug" (also termed chemotherapy) as used herein refers to a drug treatment intended for eliminating or destructing (killing) cancer cells. The mechanism underlying the activity of some chemotherapeutic drugs is based on destructing rapidly dividing cells, as many cancer cells grow and multiply more rapidly than normal cells. As a result of their mode of activity, chemotherapeutic agents also harm cells that rapidly divide under normal circumstances, for example bone marrow cells, digestive tract cells, and hair follicles. Insulting or damaging normal cells result in the common sideeffects of chemotherapy: myelosuppression (decreased production of blood cells, hence also immuno-suppression), mucositis (inflammation of the lining of the digestive tract), and alopecia (hair loss).

Various different types of chemotherapeutic drugs are available. A chemotherapeutic drug may be used alone or in combination with another chemotherapeutic drug or with other forms of cancer therapy, such as a biological drug, radiation therapy or surgery.

Certain chemotherapy agents have also been used in the treatment of conditions other than cancer, including ankylosing spondylitis, multiple sclerosis, Crohn's disease, psoriasis, psoriatic arthritis, rheumatoid arthritis, lupus and scleroderma.

Chemotherapeutic drugs affect cell division or DNA synthesis and function and can be generally classified into groups, based on their structure or biological function. The present invention generally pertains to chemotherapeutic agents that are classified as alkylating agents, anti-metabolites, anthracyclines, plant alkaloids, topoisomerase inhibitors, and other anti-tumor agents.

However, several chemotherapeutic drugs may be classified as relating to more than a single group. It is noteworthy that some agents, including monoclonal antibodies and tyrosine kinase inhibitors, which are sometimes referred to as "chemotherapy", do not directly interfere with DNA synthesis or cell division but rather function by targeting specific differences between cancer cells and normal cells and are generally referred to as "targeted therapies", "biological therapy" or "immunotherapeutic agent" as detailed below.

Therefore, in yet another embodiment, the invention provides a method for determining the efficacy of treating a subject suffering from a chronic inflammatory condition with a chemotherapeutic agent/s. In more specific embodiments, such chemotherapeutic agent may be at least one of an alkylating agent, an anti-metabolite, a plant alkaloid, a terpenoid, a taxane, an anthracycline, a topoisomerase inhibitor, a cytotoxic antibiotic and an anti-tumor agent.

Still further, according to another specific embodiment, the invention provides a method for determining the efficacy of treating a subject suffering from a chronic inflammatory condition with a combination of chemotherapeutic agent/s and at least one of biological agent and immuno-therapeutic agent.

In more specific embodiments, the invention provides a method for determining the efficacy of treating a subject suffering from a chronic inflammatory condition with a chemotherapeutic agent that may be at least one alkylating agent. As their name implies, alkylating agents function by alkylating many nucleophilic functional groups under conditions present in cells. Examples of chemotherapeutic agents that are considered as alkylating agents are cisplatin and carboplatin, as well as oxaliplatin. Alkylating agents impair cell function by forming covalent bonds with amino, carboxyl, sulfhydryl, and phosphate groups in various biologically-significant molecules. Examples of agents which function by chemically modifying DNA are mechlorethamine, cyclophosphamide, chlorambucil and ifosfamide. An additional agent acting as a cell cycle non-specific alkylating antineoplastic agent is the alkyl sulfonate agent busulfan (also known as Busulfex).

Thus, in some embodiments, the method of the invention may be used to determine the effect of alkylating chemotherapeutic agents on a host's immune system. In further embodiments, the method of the invention using the expression level of CD247 as a biomarker is exemplified herein below in Example 1 for the alkylating chemotherapeutic agent cyclophosphamide.

In yet another specific embodiment, the invention provides a method for determining the efficacy of treating a chronic inflammatory condition, specifically, a proliferative disorder, with Cyclophosphamide. More specifically, the chemotherapeutic agent Cyclophosphamide (also known by the trade names Endoxan, Endoxan, Cytoxan, Neosar, Procytox and Revimmune or by the name cytophosphane), is a nitrogen mustard alkylating agent of the oxazophorines group that acts by adding an alkyl group to DNA (particularly to guanine, at the number 7 nitrogen atom of the imidazole ring). Cyclophosphamide is used alone for the treatment of several types of cancers but often in combination with other drugs to treat breast cancer, leukemia and ovarian cancer. It also is approved for treating nephrotic syndrome (a disease of the kidneys) in children. Unapproved uses include the treatment of Wegener's granulomatosis, severe rheumatoid arthritis, lupus erythematosus, advanced mycosis fungoides, and several of forms of vasculitis.

As described herein below in Example 2, in some embodiments the method of the invention may be used to determine the efficacy of the alkylating chemotherapeutic agent busulfan on a host's immune system. Thus, in yet another specific embodiment, the invention provides a method for determining the efficacy of treating a chronic inflammatory condition, specifically, a proliferative disorder, with Busulfan. The chemotherapeutic agent Busulfan (also known by the trade names Myleran and Busulfex, or by the chemical designation is 1,4-butanediol dimethanesulfonate) is a drug used for the treatment of cancer since 1959. Busulfan is a cell cycle non-specific alkylating anti-neoplastic agent, in the class of alkyl sulfonates. Its mechanism of action through alkylation produces guanine-adenine intrastrand crosslinks. This type of damage to the DNA cannot be repaired by cellular machinery and thus the cell undergoes apoptosis. Busulfan is given in high doses before a stem cell transplant to treat some types of leukemia and other types of cancer. It may also be given in standard doses to treat other blood-related disorders.

The relative effects of the alkylating agents Cyclophosphamide and Busulfan on the immune system of a host using CD247 as a biomarker, as well as of other chemotherapeutic agents, or any combinations thereof, is also summarized herein below in Example 4.

In other specific embodiments, the invention provides a method for determining the efficacy of treating a subject suffering from a chronic inflammatory condition with a chemotherapeutic agent that may be at least one Antimetabolite. Anti-metabolites (also termed purine and pyrimidine analogues) mimic the structure of purines or pyrimidines which are the building blocks of DNA and may thus be incorporated into DNA. The incorporation of anti-metabolites into DNA interferes with DNA syntheses, leading to abnormal cell development and division. Anti-metabolites also affect RNA synthesis. Examples of anti-metabolites include 5-fluorouracil (5-FU), azathioprine and mercaptopurine, fludarabine, cladribine (2-chlorodeoxyadenosine, 2-CdA), pentostatin (2'-deoxycoformycin, 2'-DCF), nelarabine, Floxuridine (FUDR) and Cytosine arabinoside (Cytarabine).

As described herein below in Example 2, in some further embodiments the present invention demonstrates determining the expression level of CD247 for assessing the efficacy of treatment with anti-metabolite chemotherapeutic agents during chronic inflammation, particularly, the anti-metabolite agent 5-fluorouracil (5-FU).

Thus, according to one particular embodiment, the method of the invention may be applicable for determining the efficacy of treatment of a subject suffering from a chronic inflammatory condition with 5-FU. The chemotherapeutic drug 5-Fluorouracil (also known as Fluorouracil, 5-FU or f5U, or by the trade names Adrucil, Carac, Efudix, Efudex and Fluoroplex) is a pyrimidine analogue anti-metabolite which is used in the treatment of cancer, through the irreversible inhibition of thymidylate synthase.

As a pyrimidine analogue, it may transform inside cells into different cytotoxic metabolites which are then incorporated, inter alia, into DNA and RNA, finally inducing cell cycle arrest and apoptosis by inhibiting the cell's ability to synthesize DNA properly. 5-FU is mainly used in the treatment of colorectal cancer and pancreatic cancer and is sometimes used in the treatment of inflammatory breast cancer.

The efficacy of treatment with the anti-metabolite chemotherapeutic agent 5-fluorouracil during a chronic inflammation condition is also demonstrated for a combined treatment of 5-FU and another chemotherapeutic agent, namely, Irinotecan (CPT11), as detailed herein below.

Still further, according to other specific embodiments, the invention provides a method for determining the efficacy of treating a subject suffering from a chronic inflammatory condition with a chemotherapeutic agent that may be at least one Plant alkaloid and terpenoid. Plant alkaloids and terpenoids are agents derived from plants that block cell division by preventing microtubule function, thereby inhibiting the process of cell division (also known as "mitotic inhibitors" or "anti-mitotic agents"). Examples of alkaloids include the vinca alkaloids (e.g. vincristine, vinblastine, vinorelbine and vindesine) and terpenoids include, for example, taxanes (e.g. paclitaxel and docetaxel). Taxanes act by enhancing the stability of microtubules, preventing the separation of chromosomes during anaphase.

In further specific embodiments, the invention provides a method for determining the efficacy of treating a subject suffering from a chronic inflammatory condition with a chemotherapeutic agent that may be at least one Topoisomerase inhibitor. Topoisomerases are essential enzymes that maintain DNA topology (i.e. the overall three dimensional structure of DNA). Inhibition of type I or type II topoisomerases interferes with both transcription and replication of DNA by inhibiting proper DNA supercoiling. Type I topoisomerase inhibitors include camptothecins (e.g. irinotecan and topotecan) and examples of type II inhibitors include amsacrine, etoposide, etoposide phosphate, and teniposide.

As described in Example 1 herein below, in yet further embodiments, the present invention provides a method for determining the efficacy of a treatment by type I topoisomerase inhibitors as a therapeutic agent during a state of chronic inflammation, by determining the expression level of CD247. Specifically, the present invention exemplifies the effect on the host immune state in response to a treatment with the topoisomerase inhibitor irinotecan (CPT11) alone (Example 1 below) or in combination with the anti-metabolite agent 5-FU (Examples 8 and 9).

In yet another specific embodiment, the invention provides a method for determining the efficacy of treating a chronic inflammatory condition, specifically, a proliferative disorder, with Irinotecan. More specifically, the chemotherapeutic agent Irinotecan (also known as CPT-11), which is a semisynthetic analogue of the natural alkaloid camptothecin, is a drug used for the treatment of cancer. Irinotecan acts by preventing DNA from unwinding, via the inhibition of topoisomerase I. It is mainly used for the treatment of colon cancer, in particular, in combination with other chemotherapy agents (including the regimen FOLFIRI, which consists of infusional 5-fluorouracil, leucovorin, and irinotecan.

In more specific embodiments, the invention provides a method for determining the efficacy of treating a subject suffering from a chronic inflammatory condition with a chemotherapeutic agent that may be at least one Anthracycline.

Anthracyclines (or anthracycline antibiotics) are a class of drugs used in cancer chemotherapy that are derived from the streptomyces bacterium. These compounds are used to treat many cancers, including leukemias, lymphomas, breast, uterine, ovarian, and lung cancers. These agents include, inter alia, the drugs daunorubicin (also known as Daunomycin), and doxorubicin and many other related agents (e.g., Valrubicin and Idarubicin). For example, the anthracycline agent Idarubicin acts by interfering with the enzyme topoisomerase II.

As described in Example 2 herein below, in some embodiments, the present invention provides a method for determining the efficacy of a treatment by anthracycline chemotherapeutic agents, particularly by doxorubicin, during a state of chronic inflammation, by determining the expression level of CD247.

In yet another specific embodiment, the invention provides a method for determining the efficacy of treating a chronic inflammatory condition, specifically, a proliferative disorder, with Doxorubicin. The chemotherapeutic agent Doxorubicin (also known by the trade name Adriamycin and by the name hydroxydaunorubicin) is an anthracycline antibiotic that is closely related to the natural product daunomycin, and like all anthracyclines, it works by intercalating DNA. The most serious adverse side effect of using this agent is the life-threatening heart damage. It is commonly used in the treatment of a wide range of cancers, including hematological malignancies, many types of carcinoma, and soft tissue sarcomas.

In other specific embodiments, the invention provides a method for determining the efficacy of treating a subject suffering from a chronic inflammatory condition with a chemotherapeutic agent that may be at least one Cytotoxic antibiotics. The anthracyclines agents described above are also classified as "cytotoxic antibiotics". Cytotoxic antibiotics also include the agent actinomycin D (also known generically as Actinomycin or Dactinomycin), which is the most significant member of the actinomycines class of polypeptide antibiotics (that were also isolated from streptomyces). Actinomycin D is shown to have the ability to inhibit transcription by binding DNA at the transcription initiation complex and preventing elongation of RNA chain by RNA polymerase. Other cytotoxic antibiotics include bleomycin and mitomycin.

It must be appreciated that the method of the invention as well as any compositions and kits described herein after are applicable in determining the efficacy of treatment and monitoring a disease progression in response to treatment with any of the chemotherapeutic agents, any combinations of at least two chemotherapeutic agents, any combination with a biological agent or any immuno-therapeutic agents or any combinations thereof.

The term "in combination with" such as when used in reference to a therapeutic regimen, refers to administration or two or more therapies over the course of a treatment regimen, where the therapies may be administered together or separately, and, where used in reference to drugs, may be administered in the same or different formulations, by the same or different routes, and in the same or different dosage form type.

The inventors demonstrated that the immunosuppressive environment negatively affects newly administered T cells, and thus could limit the success of cancer biological therapy that may include non-immune or immunotherapy based on vaccination, T cell transfer and antibody-mediated therapy and that the expression level of CD247 may also be a biomarker for predicting the suitability of a subject to receiving such treatment or for monitoring the immune environment of a subject during such treatment. The present invention thus provides an efficient method for determining the efficacy and suitability of a certain therapeutic agent, specifically, an immuno-therapeutic agent or any combinations thereof with other chemotherapeutic agents.

Cancer vaccines, antibody treatments, and other "immunotherapies" are potentially more specific and effective and less toxic than the current approaches of cancer treatment and are generally termed "immunotherapy", and therefore, an agent used for immunotherapy, is defined herein as an immuno-therapeutic agent. The term immunotherapy as herein defined (also termed biologic therapy or biotherapy) is a treatment that uses certain parts of the immune system to fight diseases (e.g. cancer), by, inter alia, stimulating the immune system to become more efficient in attacking cancer cells (e.g., by administering vaccines) or by administering components of the immune system (e.g., by administering cytokines, antibodies, etc.).

In the last few decades immunotherapy has become an important part of treating several types of cancer with the main types of immunotherapy used being monoclonal antibodies (either naked or conjugated), cancer vaccines (i.e. that induce the immune system to mount an attack against cancer cells in the body) and non-specific immunotherapies.

Thus, in yet other embodiments, the immune-therapeutic agent may be at least one of adoptive cell transfer, a cancer vaccine, antibody-based therapy, a hormone, a cytokine or any combination thereof.

More specifically, cancer vaccines as referred to herein are vaccines that induce the immune system to mount an attack against cancer cells in the body. A cancer treatment vaccine uses cancer cells, parts of cells, or pure antigens to increase the immune response against cancer cells that are already in the body. These cancer vaccines are often combined with other substances or adjuvants that enhance the immune response. Non-specific immunotherapies as referred to herein do not target a certain cell or antigen, but rather stimulate the immune system in a general way, which may still result in an enhanced activity of the immune system against cancer cells. A non-limiting example of non-specific immunotherapies includes cytokines (e.g. interleukins, interferons).

Antibody-mediated therapy as referred to herein refers to the use of antibodies that are specific to a cancer cell or to any protein derived there-from for the treatment of cancer. As a non limiting example, such antibodies may be monoclonal or polyclonal which may be naked or conjugated to another molecule. Antibodies used for the treatment of cancer may be conjugated to a cytotoxic moiety or radioactive isotope, to selectively eliminate cancer cells.

The term "adoptive transfer" as herein defined applies to all the therapies that consist of the transfer of components of the immune system that are already capable of mounting a specific immune response. Examples of adoptive transfer include both the transfer of antibodies and also, specific types of cells that are capable of mediating antigen-specific tumor regression such as LAK and T cells. Cell-based therapies with various lymphocytes and antigen-presenting cells are promising approaches for cancer immunotherapy. The transfusion of T lymphocytes, also called adoptive cell therapy (ACT), is an effective treatment for viral infections and has induced regression of cancer in early stage clinical trials.

As demonstrated in Example 3 (FIG. 15), CD247 expression may serve as a sensitive biomarker sensing whether treatment with a certain immuno-therapeutic agent such as the TNF-α inhibitor, Etanercept, may be effective in reducing or eliminating the chronic inflammatory condition. As used herein, the agent Etanercept (also known by the trade name Enbrel) is a drug that treats autoimmune diseases by acting as a tumor necrosis factor (TNF) inhibitor. More specifically, Etanercept is a large molecule, with a molecular weight of 150 kDa, that binds to TNFα and decreases its role in disorders involving excess inflammation in humans and other animals, including autoimmune diseases such as ankylosing spondylitis, juvenile rheumatoid arthritis, psoriasis, psoriasis arthritis, rheumatoid arthritis and, potentially, in a variety of other disorders mediated by an excess of TNFα, the therapeutic potential being based on the fact that TNFα is the "master regulator" of the inflammatory response in many organ systems.

It should be noted that the term "biological treatment" or "biological agent", as used herein refers to any biological material that affects different cellular pathways. Such agent may include antibodies, for example, antibodies directed to cell surface receptors participating in signaling, that may either activate or inhibit the target receptor. Such biological agent may also include any soluble receptor, cytokine, peptides or ligands. Non limiting examples for monoclonal antibodies that are used for the treatment of cancer include bevacizumab (also known as Avastin), cetuximab (also known as Erbitux), anti-CTLA4 antibody and panitumumab (also known as Vectibix) and anti Gr1 antibodies.

As shown by the following Examples, the inventors examined the CD247 expression levels in both spleen cells and peripheral blood lymphocytes. Still further, FIG. 25 demonstrates the use of biopsies obtained from different locations in colons of subjects suffering from CRC. Thus, according to some embodiments, the biological sample tested by the method of the invention may be any one of a blood sample, a spleen biopsy, cells from lymph nodes and a tissue biopsy, specifically, colon tissue.

It should be noted that certain embodiments of the invention contemplate the use of different biological samples. The term "sample" in the present specification and claims is meant to include biological samples. Biological samples may be obtained from mammal, specifically, a human subject, include fluid, solid (e.g., stool) or tissues. The term "sample" may also include body fluids such as whole blood sample, blood cells, bone marrow, lymph fluid, serum, plasma, urine, sputum, saliva, faeces, semen, spinal fluid or CSF, the external secretions of the skin, respiratory, intestinal, and genitourinary tracts, tears, milk, any human organ or tissue, any biopsy, for example, lymph node or spleen biopsies, any sample taken from any tissue or tissue extract, any sample obtained by lavage optionally of the breast ductal system, plural effusion, samples of in vitro or ex vivo cell culture and cell culture constituents. Some samples that are a priori not liquid are contacted with a liquid buffers which are then used according to the diagnostic method of the invention.

Biological samples may be obtained from all of the various families of domestic animals, as well as feral or wild animals, including, but not limited to, such animals as ungulates, bear, fish, lagamorphs, rodents, etc. Preferably, the sample is liquid, specifically, a body fluid sample, most preferably, a serum sample and of mammalian origin, specifically, human. In specific embodiment, a blood sample is being used by the invention. In yet another specific embodiment, the method of the invention is applicable for testing any tissue sample, for example, lymph nodes and spleen, biopsies.

The present invention relates to the diagnosis and monitoring of subjects or patients, in need thereof. By "patient" or "subject in need" it is meant any organism who may be affected by the above-mentioned conditions, and to whom the monitoring and diagnosis methods herein described is desired, including humans, domestic and non-domestic mammals such as canine and feline subjects, bovine, simian, equine and murine subjects, rodents, domestic birds, aquaculture, fish and exotic aquarium fish. It should be appreciated that the diagnosed or monitored subject may be also any reptile or zoo animal. More specifically, the methods of the invention are intended for mammals. By "mammalian subject" is meant any mammal for which the proposed therapy is desired, including human, livestock, equine, canine, and feline subjects, most specifically humans.

According to a second aspect, the invention relates to a composition comprising:

(a) detecting molecules specific for determining the level of expression of CD247 in a biological sample; and optionally (b) detecting molecules specific for determining the level of expression of at least one reference control in a biological sample.

In an optional embodiment, detecting molecules of (a) and (b) may be attached to a solid support.

According to certain embodiments, the composition of the invention may be for use in a method for determining the efficacy of a treatment with a therapeutic agent on a subject suffering from a chronic inflammatory condition. More specifically, such method provides determining whether a subject suffering from a chronic inflammatory condition would respond, specifically, in exhibiting a beneficial response to a treatment with a therapeutic agent. In certain embodiments, such therapeutic agent may be at least one chemotherapeutic agent, at least one immunotherapeutic agent or any combination thereof.

In certain embodiments, the detecting molecules specific for CD247 comprised within the composition of the invention, and optionally when used, detecting molecules specific for at least one reference control, may be selected from isolated detecting amino acid molecules and isolated detecting nucleic acid molecules.

In more specific embodiments, such detecting amino acid molecule specific for CD247 may be an isolated antibody that specifically recognizes and binds CD247.

As noted above, in certain embodiments, the compositions of the invention may further comprise detecting molecules specific for control reference protein. Such reference protein may be used for normalizing the detected expression levels for the biomarker of the invention CD247.

In yet other specific embodiments, the composition of the invention comprises at least one reference control that may be at least one of CD3ε, CD3δ, CD3γ, TCRα, TCRβ and CD56.

According to certain embodiments, the composition of the invention may be used for determining the efficacy of a therapeutic agent that may be a chemotherapeutic agent that may be at least one of an alkylating agent, an anti-metabolite, a plant alkaloid, a terpenoid, a taxane, an anthracycline, a topoisomerase inhibitor, a cytotoxic antibiotic and an anti-tumor agent.

In yet another embodiment, the composition of the invention may be used in a method for determining the efficacy of treatment with an immune-therapeutic agent that may be at least one of adoptive cell transfer, a cancer vaccine, antibody-based therapy, a hormone, a cytokine or any combination thereof.

According to one optional embodiment, the compositions described by the invention or any components thereof, specifically, the detecting molecules may be attached to a solid support. The solid support may include polymers, such as polystyrene, agarose, sepharose, cellulose, glass, glass beads and magnetizable particles of cellulose or other polymers. The solid-support can be in the form of large or small beads, chips or particles, tubes, plates, or other forms.

Taken together, diagnostic and prognostic agents of the present invention (e.g., antibodies and oligonucleotide, described above) can be packaged in a diagnostic kit. Such diagnostic kits can include an antibody (e.g., labeled) of the present invention in one container and a solid phase for attaching multiple biological samples packaged in a second container as well as imaging reagent in a third container (e.g., secondary labeled antibody) with appropriate buffers and preservatives and used for diagnosis.

Thus, in a third aspect of the invention relates to a kit comprising:

(a) detecting molecules specific for determining the level of expression of CD247 in a biological sample and optionally detecting molecules specific for at least one reference control; and optionally at least one of:

(b) pre-determined calibration curve providing at least one of standard expression values of CD247 and standard values determined for the rate of change in the CD247 expression in response to said treatment;

(c) at least one control sample.

Optionally, as an additional element (c), the kit of the invention may include at least one control sample. It should be noted that in certain embodiments, the control sample may include samples of subjects (preferably, with a matching gender and age) suffering from a specific chronic inflammatory condition, samples from treated subjects that display a beneficial response ("responders"), samples of treated subjects that do not respond (non responders), samples from healthy subjects, and optionally, samples of subjects suffering from a different pathologic condition.

According to certain embodiments, the kit of the invention used in a method for determining the efficacy of a treatment with a therapeutic agent on a subject suffering from a chronic inflammatory condition. More specifically, the kit of the invention may be used for determining whether a subject suffering from a chronic inflammatory condition would respond and would exhibit a beneficial response to a treatment with a therapeutic agent. Such therapeutic agent may be at least one chemotherapeutic agent, at least one immunotherapeutic agent or any combination thereof.

It should be appreciated that the kit of the invention may be applicable for monitoring and assessing responsiveness of a subject suffering from a chronic-inflammatory condition to a treatment with a therapeutic agent. Such instructions may include at least one of:

(a) instructions for carrying out the determining of the level of expression of CD247 in a biological sample and optionally for determining the expression level of at least one reference control. More specifically, instructions for carrying out the detection and quantification of expression of the biomarker of the invention, CD247 and of at least one said control reference in the tested sample. Such instruction may also indicate procedure for obtaining an expression value of said CD247 in said sample.

(b) instructions for calculating the rate of change of the expression values (preferably, normalized values) of said CD247 between said temporally-separated test samples.

(c) instructions for comparing the expression values or the rate of change in the expression of CD247, obtained with the corresponding predetermined calibration curve, or with or with an expression value of CD247 obtained from a control sample.

In certain embodiments, the kit of the invention may further comprise instructions for normalizing the expression levels of CD247 in a sample as compared to a reference control, for example, CD3ε or any one of CD3δ, CD3γ, TCRα, TCRβ and CD56.

Still further, in specific embodiments, where an active calibration curve is being used, the kit of the invention may further comprise any reagents necessary for preparing such calibration curve. It should be understood that such active calibration curve serves as a reference curve adjusted for each particular method used for determining the expression of CD247 in the examined sample. In one particular example, the kit of the invention may include beads/or fixed cells stained with different fluorescent intensities representing the range of the CD247 expression levels in the healthy population of age and gender matched subjects.

It should be noted that a positive rate of change of said expression values in a sample obtained after initiation of said treatment as compared to the CD247 expression value in a sample obtained prior to initiation of said treatment, is indicative of the responsiveness of said subject to said treatment, that leads either directly or indirectly to an anti-inflammatory effect.

In certain embodiments the kit of the invention may comprise at least one calibration curve. Such calibration curves may include at least one of (a) a pre-determined calibration curve providing normalized standard expression values of said CD247 (b) a predetermined standard [cutoff] rate of change between expression values of CD247 obtained for at least one subject prior to said therapy and after the initiation of said therapy; (c) a predetermined standard [cut-off] rate of change between expression values of CD247 obtained for at least one subject in at least two temporally-separated samples obtained for said at least one subject after the initiation of therapy.

The kit of the invention comprises detecting molecules specific for CD247 and optionally detecting molecules specific for at least one reference control. In some specific embodiments, such detecting molecules may be selected from isolated detecting amino acid molecules and isolated detecting nucleic acid molecules.

In more specific embodiments, the detecting amino acid molecule specific for CD247 may be an isolated antibody that specifically recognizes and binds CD247.

According to some specific embodiments, the kit of the invention may further comprise detecting molecules specific for reference control that may be at least one of CD3ε, CD3δ, CD3γ, TCRα, TCRβ, CD56 and in some embodiments also TCRγ or TCR δ.

In one specific embodiment, the kit of the invention may be particularly suitable for determining if a specific chemotherapeutic agent exhibits a beneficial effect on a subject suffering from a chronic inflammatory condition. In more specific embodiments, such chemotherapeutic agent may be at least one of an alkylating agent, an anti-metabolite, a plant alkaloid, a terpenoid, a taxane, an anthracycline, a topoisomerase inhibitor, a cytotoxic antibiotic and an anti-tumor agent.

In yet another embodiment, the kit of the invention may be used for determining the suitability of using an immuno therapeutic agent for the treatment of a chronic inflammatory condition. Such immunotherapeutic agent may include at least one of adoptive cell transfer, a cancer vaccine, antibody-based therapy, a hormone, a cytokine or any combination thereof.

In yet another embodiment, the kit of the invention may be specifically useful in determining an optimal treatment for a subject suffering from any chronic inflammatory condition, for example, a proliferative disorder, an autoimmune disorder or an infectious disorder. More specific embodiments relate to a proliferative disorder.

According to particular and specific embodiments, where a combined use of CD247 with other biomarkers is applied, the kit of the invention may further comprise at least one of:

(a). detecting molecules specific for determining the level of expression of S100A8 and/or S100A9 in a biological sample;

(b). detecting molecules specific for determining the level of expression of caspases 3 in a biological sample;

(c). detecting molecules or reagents for determining MDSCs population in a biological sample; and (d) detecting reagents for determining the ROS and NO levels in a sample.

In certain embodiments, where the level of expression of CD247 is determined at the protein level, an immunoassay selected from the group consisting of FACS, a Western blot, an ELISA, a RIA, a slot blot, a dot blot, immunohistochemical assay and a radio-imaging assay is used. Therefore, the kit of the invention may further comprise reagents required for performing said assays.

In other embodiments where a combined detection of CD247 with other biomarkers is performed, the kit of the invention may further comprise detecting amino acid molecules such as any one of isolated antibody that specifically recognizes and binds CD11b and an isolated antibody that specifically recognizes and binds Gr1, antibodies recognizing the S100A8 and S100A9 proteins etc.

According to certain alternative embodiments, the detecting molecules for CD247 expression are isolated detecting nucleic acid molecules. According to some embodiments, such detecting nucleic acid molecules may be isolated oligonucleotides, each oligonucleotide specifically hybridizes to a nucleic acid sequence of the RNA products of said CD247. More specifically, the oligonucleotide used as a detecting molecule according to certain embodiments of the invention may be any one of a pair of primers or nucleotide probe. In such case, the level of expression of CD247 may be determined using a nucleic acid amplification assay selected from the group consisting of: a Real-Time PCR, micro arrays, PCR, in situ Hybridization and Comparative Genomic Hybridization. In certain embodiments, where the nucleic acid based detecting molecule is an aptamer, the detection of CD247 expression is performed at the protein level.

As noted above, the kit of the invention may comprise detecting molecules for at least one reference control protein. According to certain embodiments, such reference control may be any one of CD3ε, CD3δ, CD3γ, TCRα and TCRβ, for T cells, CD56 and SNX27.

It should be noted that in certain embodiments, the kit of the invention may comprise detecting molecules specific for CD3ε that is used as the reference control protein. In yet another specific embodiment, CD56 is used as a reference control. Still further, anther embodiment of the invention relates to SNX27 as a control reference.

In yet another embodiment, the kit of the invention may be adapted for examining different biological samples. In some embodiments the biological sample may be any one of a whole blood sample, blood cells, bone marrow, lymph fluid, Spleen lymph nodes tissue samples, serum, plasma, urine, sputum, saliva, faeces, semen, spinal fluid or CSF, the external secretions of the skin, respiratory, intestinal, and genitourinary tracts, tears, milk, any human organ or tissue, any sample obtained by lavage optionally of the breast ductal system, plural effusion, samples of in vitro or ex vivo cell culture and cell culture constituents.

According to specific embodiments, the biological sample may be a blood sample. The kit of the invention may therefore optionally comprise suitable mans for obtaining said sample. More specifically, for using the kit of the invention, one must first obtain samples from the tested subjects. To do so, means for obtaining such samples may be required. Such means for obtaining a sample from the mammalian subject (a) can be any means for obtaining a sample from the subject known in the art. Examples for obtaining e.g. blood or bone marrow samples are known in the art and could be any kind of finger or skin prick or lancet based device, which basically pierces the skin and results in a drop of blood being released from the skin. In addition, aspirating or biopsy needles may be also used for obtaining spleen lymph nodes tissue samples. Samples may of course be taken from any other living tissue, or body secretions comprising viable cells, such as biopsies, saliva or even urine.

The inventors consider the kit of the invention in compartmental form. It should be therefore noted that the detecting molecules used for detecting the expression levels of CD247 may be provided in a kit attached to an array. As defined herein, a "detecting molecule array" refers to a plurality of detection molecules that may be nucleic acids based or protein based detecting molecules (specifically, antibodies), optionally attached to a support where each of the detecting molecules is attached to a support in a unique pre-selected and defined region.

For example, an array may contain different detecting molecules, such as specific antibodies or primers. It should be noted that each detecting molecule may be spatially arranged in a predetermined and separated location in an array. For example, an array may be a plurality of vessels (test tubes), plates, micro-wells in a micro-plate, each containing different detecting molecules, specifically, antibodies, against CD247. An array may also be any solid support holding in distinct regions (dots, lines, columns) different and known, predetermined detecting molecules.

As used herein, "solid support" is defined as any surface to which molecules may be attached through either covalent or non-covalent bonds. Thus, useful solid supports include solid and semi-solid matrixes, such as aerogels and hydrogels, resins, beads, biochips (including thin film coated biochips), microfluidic chip, a silicon chip, multi-well plates (also referred to as microtiter plates or microplates), membranes, filters, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, nylon, latex bead, magnetic bead, paramagnetic bead, superparamagnetic bead, starch and the like. This also includes, but is not limited to, microsphere particles such as Lumavidin™ or LS-beads, magnetic beads, charged paper, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces and grooved surfaces.

It should be further appreciated that any of the reagents, substances or ingredients included in any of the methods and kits of the invention may be provided as reagents embedded, linked, connected, attached, placed or fused to any of the solid support materials described above.

The diagnostic kits and methods of the invention further provide a tool for a "tailor-made" or personalized therapy, by identifying subjects suffering from a specific chronic inflammation that are likely to be benefit from treatment with an anti-inflammatory therapeutic agent.

Thus, according to a further aspect of some embodiments of the present invention there is provided a method of selecting a treatment regimen for treating a subject diagnosed with a chronic inflammatory condition, the method comprising: (a) determining and evaluating the efficacy of a treatment with a therapeutic agent given to a subject suffering from a chronic-inflammatory condition according to the method of some embodiments of the invention, and (b) selecting a treatment regimen based on the evaluation; thereby selecting the treatment regimen for treating the subject diagnosed with said chronic inflammatory condition. In yet another embodiment, the invention provides a method of treating of a subject diagnosed with a chronic inflammatory condition, by evaluating the efficacy of a treatment, specifically, either a direct or indirect anti-inflammatory treatment, and selecting a treatment regimen based on the evaluation.

The term "treatment or prevention" as used herein, refers to the complete range of therapeutically positive effects of administrating to a subject including inhibition, reduction of, alleviation of, and relief from, a chronic inflammatory condition and illness, chronic inflammation symptoms or undesired side effects or chronic inflammatory related disorders. More specifically, treatment or prevention of relapse re recurrence of the disease in response to a treatment with a non-effective, or deleterious therapeutic agent, includes the prevention or postponement of development of the disease, prevention or postponement of development of symptoms and/or a reduction in the severity of such symptoms that will or are expected to develop. These further include ameliorating existing symptoms, preventing-additional symptoms and ameliorating or preventing the underlying metabolic causes of symptoms. It should be appreciated that the terms "inhibition", "moderation", "reduction" or "attenuation" as referred to herein, relate to the retardation, restraining or reduction of a process by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively.

The terms "decrease", "inhibition", "moderation" or "attenuation" as referred to herein, relate to the retardation, restraining or reduction of CD247 expression or levels by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

The terms "increase", "elevation", "enhancement" or "elevation" as referred to herein, relate to the enhancement and increase of CD247 expression or levels by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

All scientific and technical terms used herein have meanings commonly used in the art unless otherwise specified. The definitions provided herein are to facilitate understanding of certain terms used frequently herein and are not meant to limit the scope of the present disclosure.

As used herein the term "about" refers to ±10% The terms "comprises", "comprising", "includes", "including", "having" and their conjugates mean "including but not limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to ±10%.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It should be noted that various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Standard medicinal chemistry methods known in the art not specifically described herein are generally followed essentially in the series "Comprehensive Medicinal Chemistry" by various authors and editors, published by Pergamon Press.

Experimental Procedures

Mice

C57BL/6 and BALB/c mice (female, 6-8 weeks old) were purchased from Harlan and were grown at the Hebrew University specific-pathogen-free facility. All experiments were done in accordance with pre-approved institutional protocols.

In Vivo Chronic Inflammation Model

Induced chronic inflammation in mice was established by sustained subcutaneous injections of the heat-killed Bacille Calmette Guerin strain of *Mycobacterium tuberculosis*, (231141; Difco Laboratories) (BCG, 50 μg per animal/dose) once a week, for three weeks. The first two BCG administrations were mixed 1:1 with Incomplete Freund's adjuvant (IFA) (Sigma), and the second boost delivery was given with PBS. Mice sacrifice and cell isolations were performed two days after the third injection. Spleen weight was measured and cells from the spleen and peripheral blood (PBLs) were analyzed. The results represent three independent experiments.

A Mouse Model for Colorectal Cancer (CRC) Associated with Chronic Inflammation

The mouse model for CRC was established by two repeated injections of azoxymethane (AOM) (Sigma) in intervals of two weeks followed by two weekly administrations of DSS (Sigma) that was added to drinking water every two weeks for duration of about seven days. In order to test the influence of chemotherapeutic drugs on the induced-chronic inflammatory environment in a CRC model, after the second DSS treatment mice were randomized into three groups (n=10 mice) as follows: CRC control group, CRC and 5-FU i.p inoculated group and CRC and CPT-11 i.p inoculated group. Mice were sacrificed at week +11, three weeks after the second DSS treatment. Following the chemotherapy treatments spleens and peripheral blood cells (PBLs) were isolated and the MDSCs (Gr1+CD11b+) accumulation was revealed by flow cytometry analysis.

Chemotherapy Administration and Treatment with Biological Compound

To determine the in-vivo efficacy of chemotherapeutic FDA-approved drugs on the immune status under chronic inflammatory conditions, one day after the second BCG injection, when acute inflammations evolves into a chronic inflammation, the mice were randomly divided into two groups of four mice per group, as follows: (a) chronically inflamed control group, and (b) chronically inflamed treated group. Chemotherapy treatment was given intraperitoneal (i.p) or intravenous (i.v.) once at day 7 or twice at day 7 and 14, using the following FDA-approved drugs at the indicated dosages: Mitomycin (2.5 mg/kg, 3.25 mg/kg, 4 mg/kg, and 8 mg/kg), Irinotecan (CPT11) (50 mg/kg), Busulfan (10 mg/kg), Doxorubicin (Rubex) (8 mg/kg), and Cyclophosphamide (1 mg or 2.5 mg per animal/dose). Each experiment also included a group of 4 naive mice. In order to determine the in-vivo efficacy of FDA-approved biological treatment having an anti-inflammatory effect, the TNFα antagonist etanercept (Wyeth, UK) was used, which is a soluble form of the TNF receptor, comprising the Fc portion of IgG1 and the extracellular domain of the TNF receptor (p75) [31] Etanercept was administered daily (0.5 mg/dose) by systemic intraperitoneal injection, starting from 1 day before the second BCG injection, until one day before cell harvest (FIG. 6A). Control mice were injected with PBS.

Flow Cytometry, Antibodies and Reagents

Isolated splenocytes and peripheral blood leukocytes (PBLs) were treated with erythrocyte lysis buffer and washed in PBS. Cells were pre-coated with anti-CD16/CD32 (Biolegend) for FcR blockage. For surface staining, cells were incubated for 30 min at 4° C. with FITC-labeled anti-Gr1, anti-CD11c, and anti-CD4; PE-labeled anti F4/80, anti-CD3ε, anti-CD45R/B220, and anti-mNKp46; and biotinylated anti-CD11b and anti-CD8 that were detected with streptavidin-Cy5 (Biolegend and eBioscience). Intracellular staining of CD247 cells was performed by subjecting the cells to fixation with paraformaldehyde (1%) for 20 min at 4° C., followed by washing and permeabilization for 10 min with saponin detergent (0.1%) at room temperature (RT). Cells were then washed and incubated with FITC-labeled monoclonal anti-CD247 (H146) (Abcam), or biotinylated monoclonal anti-CD247 (H146), which were subsequently detected with streptavidin-Cy5. FoxP3 staining was performed according to the manufacturer's instructions. Samples were analyzed using FACSCalibur with Cell Quest software (BD).

Cell Lysis and Western Blot Analysis

Analyses used either the splenocyte population or peripheral blood as mentioned above. Cells ($5\times10^7$/ml, or $1\times10^6$/ml) were lysed with Tris-NaCl buffer containing 0.5% Triton X-100 and protease inhibitors for 30 min on ice. Proteins were resolved on 12% SDS-PAGE and subjected to immunoblotting analysis using the following specific antibodies: anti-CD247, antiCD3ε antibodies, anti-S100A9, anti-S100A8, anti-iNOS, anti-ARG1, and anti-αTubulin antibodies. Specific antibodies were detected by incubation with protein A (Amersham), anti-rat or anti-goat antibodies conjugated to horseradish peroxidase (Jackson Immunoresearch), followed by enhanced chemiluminescence and exposure to Kodak X-ray films.

Cytotoxic In-Vivo Assay

The in-vivo cytotoxic activity of NK-cells was determined using donor splenocytes from BALB/c and C57BL/6 mice that were stained with carboxyfluorescein succinimidyl ester (CFSE), at 0.5 μM $CFSE^{low}$ and at 5 μM $CFSE^{high}$ for 10 min at 37° C. Cells ($5\times10^{10}$) of each type were mixed and injected into the tail vain of recipient C57BL/6 mice. After the transfer (24 hours) mice were sacrificed and splenocytes and PBLs were harvested. The ratio between the syngeneic cells ($CFSE^{high}$) and allogeneic cells ($CFSE^{low}$) was evaluated using FACS analysis. The percentage of specific allogeneic cell clearance was calculated by the formula: R1 (initial ratio)=High/Low; R2 (final ratio)=High/Low; R (corrected ratio)=R1/R2; Percent of killing (X %) is displayed as (1−R).

Quantitative PCR

Total RNA was recovered from splenocytes or isolated MDSCs using Tri-Reagent (Sigma) and was subjected to reverse transcription with m-MLV-RT (Invitrogen) and random primers (IDT). Quantitative mRNA expression was analyzed by real-time PCR (ABI 7900), with SYBR green (Invitrogen). RT-PCR primers were designed to recognize an exon-exon boundary in all transcripts.

Example 1

CD247 is a Biomarker Sensing the Effect of Chemotherapeutic Drugs on the Hosts' Immune System It is well established that different chemotherapeutic drugs, such as for example Irinotecan (CPT11), Cycophosphamide, Doxorubicin (Rubex), Busulfan and 5-fluorouracil (5FU), operate via different pathways (e.g. certain drugs are directed at a specific or non-specific stage of the cell cycle, while other drugs act by inducing DNA damage, etc.), all aimed at affecting tumor cell growth. The results presented herein demonstrate the effect of different chemotherapeutic drugs on the host's immune functional status. Specifically, the inventors demonstrated the unique effects of the various drugs on the host's immune status by following the protein CD247 as a biomarker.

Various chemotherapeutic drugs are considered as "antagonistic" to the hosts' immune system, i.e., these drugs act to enhance the host's immunosuppression. Among these chemotherapeutic drugs are irinotecan and cyclophosphamide, the effect of which on the immunosuppressive state of the host's immune system was examined as described herein after.

The Effect of Irinotecan on the Host's Immune System

The first chemotherapeutic drug that was used for the assessment of CD247 as a biomarker was Irinotecan (CPT11), which is known to be applied for the treatment of metastatic colorectal cancer [27-28], ovarian cancer [29] and sometimes of lung cancer [30], where all these cancer types are characterized by chronic inflammatory microenvironment.

Figure 1A:
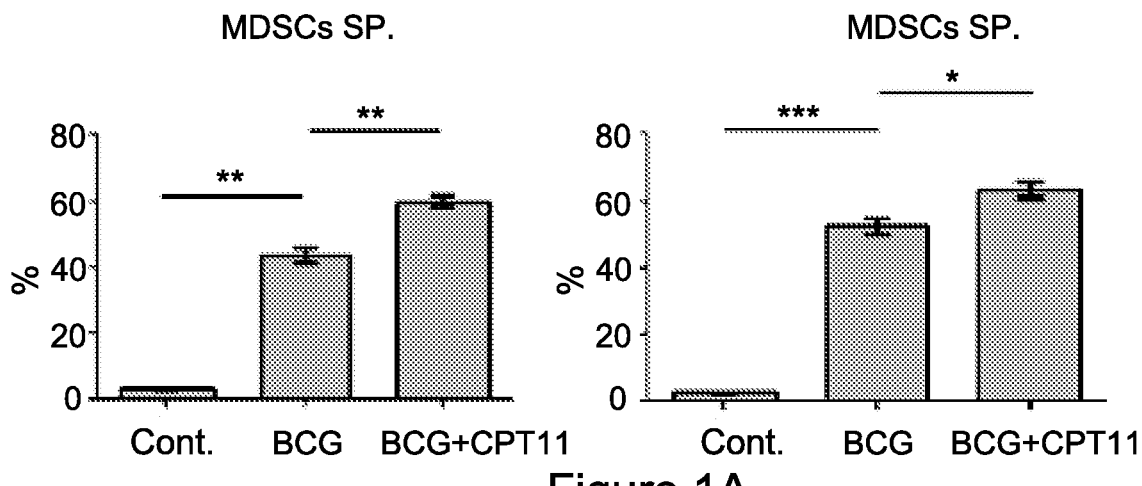
FIG. 1A-1C: Irinotecan (CPT11) increases a chronic inflammatory response
Figure 1B:
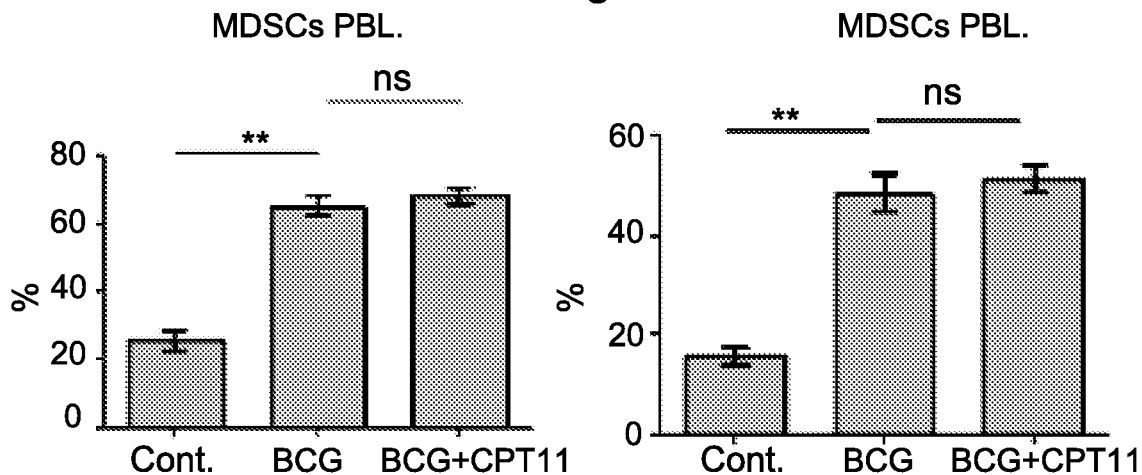
Figure 1C:
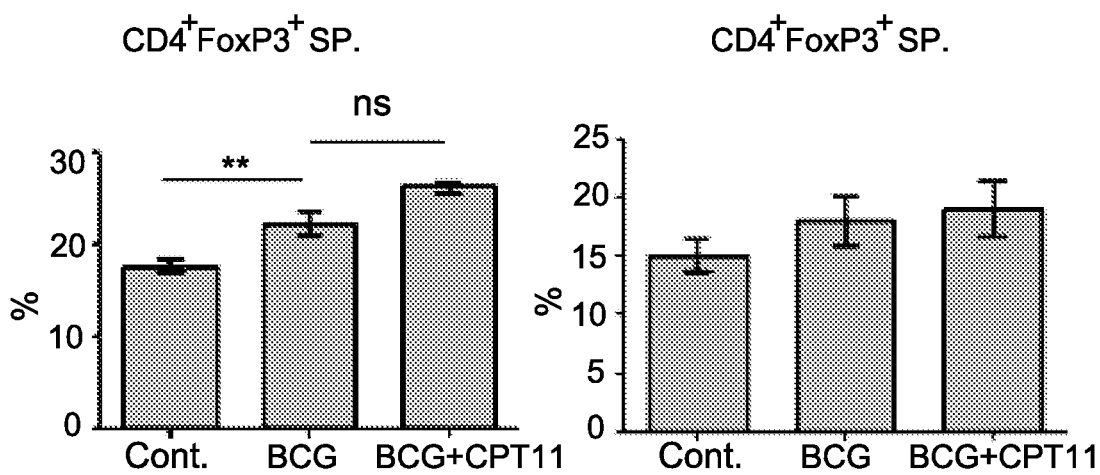

Inflamed mice (i.e. mice induced with chronic inflammation, as described above that exhibited immunosuppressive features similar to those observed during tumor growth) were exposed to the drug CPT11 either by i.v. or by i.p. treatment, as described in Experimental procedures. As shown in FIG. 1, while CPT11, either administered i.p. or i.v. significantly enhanced myeloid-derived suppressor cells (MDSC) levels in the spleen of the inflamed mice (FIG. 1A, left and right panels, respectively), the levels of MDSC in the peripheral blood remained high as in the pick of the chronic inflammatory conditions (FIG. 1B). The levels of Treg cells (a subpopulation of T cells that modulate the immune system, also known as "Regulatory T cells", or "suppressor T cells"), which have an inhibitory effect on the immune system, remained unchanged, as determined by the levels of the $CD4^+Foxp3^+$ cell population (FIG. 1C).

These results suggest an enhanced immunosuppressive environment as a result of the CPT11 treatment. By measuring the expression levels of CD247 in the spleen and blood of mice induced with chronic inflammation and treated with CPT11, the immunosuppressive effect of this drug was also manifested in a reduction in the expression level of CD247, as demonstrated in FIG. 2. As can be viewed in this figure, the expression levels of CD247, which are considerably low due to the developing inflammation, were further significantly decreased upon CPT11 treatment (FIG. 2A), both in spleen and PBLs (right and left panels, respectively), while the expression levels of CD3ε remained unchanged (FIG. 2B). This immunosuppressive state was verified by the impaired proliferative capacity of T cells under these conditions (FIG. 2C). Moreover, NK cell cytotoxic activity was affected as well, as indicated by the impaired in vivo killing activity measured by the clearance rate of allogeneic cells (FIG. 2D), which correlated with low CD247 expression in NK (NCR+) cells (FIG. 2E).

The increase in MDSCs' immunosuppressive activity in the presence of CPT11 was also verified by a significant elevation in the levels of NO and ROS, as clearly demonstrated by FIGS. 3A and 3B.

The Effect of Irinotecan on Donor T Cells

CPT11 also had a significant immunosuppressive effect on an immune-based therapy that involves adoptive transfer of normal immune cells (donor cells). As demonstrated in FIG. 4 expression levels of CD247 were significantly reduced in Normal T cells that were administered to an environment which is characterized by chronic inflammation within 24 hours from the administration and upon treatment with CPT11 induced an even stronger suppressive environment, as indicated by a significant further decrease of the expression level of CD247. Remarkably, these effects were demonstrated not only in the hosts' but also in the donor T cells.

These results suggest that CPT11 treatment on the background of a developing chronic inflammation enhances immunosuppression of T and NK cells mediated by MDSCs and affects adoptively transferred immune cells and that such a harmful effect of a chemotherapeutic drug could be detected by evaluating the expression level of the CD247 biomarker. Thus, demonstrating the feasibility of using CD247 as a marker for assessing and evaluating the efficacy of an immuno- or chemo-therapy.

The Effect of Cyclophosphamide on the Host's Immune System

Cyclophosphamide (also known as cytophosphane) is a chemotherapeutic drug mainly used in the treatment of the cancer types leukemia, lymphoma, breast cancer and neuroblastoma. Interestingly, it is also applied in cases of lupus and rheumatoid arthritis (RA). It is well established that besides its effect on the tumor, this drug also decreases the levels of regulatory T cells (Treg cells), an effect which is a beneficial to the host since it decreases Treg-mediated suppression of the immune system.

However, in many cases treatment with cyclophosphamide alone or in a combination with other drugs is not efficient. In order to gain a better understanding of the effects of cyclophosphamide on the hosts' immune system, mice in the course of chronic inflammation, which are at a state of immunosuppression as observed during tumor growth, were exposed to cyclophosphamide treatment, i.p. As expected, treatment with cyclophosphamide induced a decrease in the levels of Treg cells (FIG. 5A). However, as shown by FIG. 5B, the levels of MDSCs in the spleen remained high, consistent with the observation during chronic inflammation. Moreover, as shown in FIG. 5C, the levels of MDSCs in the blood were significantly increased, when compared to the chronic inflammatory state.

Interestingly, the immunosuppressive conditions were clearly sensed by CD247. As observed in FIG. 6A, the down-regulation of CD247 that was observed in the course of chronic inflammation was maintained upon the treatment with cyclophosphamide, while the levels of CD3ε remained normal (FIG. 6B). Without wishing to be bound by theory, these results indicate that the expression levels of CD247 are dictated by MDSCs and not by Treg cells, the population of which was found to be decreased under these conditions Immunosuppression was also verified by the impaired ability of the host to clear allogeneic cells, as demonstrated in FIG. 6C.

It is important to note that under chronic inflammation conditions and cyclophosphamide treatment, the immunosuppressive activity of MDSCs, as indicated by elevated level of nitric oxide (NO) and reactive oxygen species (ROS), was maintained high (FIGS. 7A and 7B), suggesting sustained immunosuppression.

Taken together, these results suggest that the chemotherapeutic agents CPT11 and cyclophosphamide are compounds that are included in a new group of drugs that act in an antagonistic manner to the immune system. This group includes drugs that negatively affect the hosts' immune status and increase or maintain the chronic inflammation-induced immunosuppression. As noted above, the effect of treatment by these agents may be sensed by CD247, and thus CD247 may serve as a biomarker for sensing the effect of a specific chemotherapeutic agent on the immune status of the treated patient.

Example 2

CD247 is a Biomarker Sensing the Effect of Chemotherapeutic Drugs that are Agonistic to the Hosts' Immune System Various chemotherapeutic drugs are considered as "agonistic" to the hosts' immune system, i.e., these drugs do not enhance the immunosuppressive state of the patient. The inventors therefore next examined the feasibility of using CD247 as a biomarker for sensing the beneficial effect of different "agonistic" chemotherapeutic agents on the immune status of the treated patient.

The Effect of Doxorubicin on the Host's Immune System

Doxorubicin (also known as Rubex) is a chemotherapeutic drug mainly used in the treatment of the cancer types bladder cancer, breast cancer, multiple myeloma, prostate cancer, thymoma, and others. To test the effect of doxorubicin on the immune status mice in the course of chronic inflammation, which are characterized by immunosuppression as observed during tumor growth, were exposed to Rubex treatment, i.p. As demonstrated in FIG. 8, upon treatment by Rubex, the severity of the immunosuppressive environment was dramatically decreased, as indicated by a significant decline in MDSCs in the spleen (FIG. 8A) and in the blood (FIG. 8B), while the levels of Treg cells were not affected (FIG. 8C).

As demonstrated in FIG. 9, by measuring the expression levels of CD247, the nuances of the immune status was detected by analyzing cells derived from the spleen and from blood (9A and 9B, respectively), showing a clear increase in the expression level of CD247, which is consistent with a decrease in the cell's immunosuppressive state, as stated above, further emphasizing the reliability of using CD247 as a marker for this purpose; In this case as well, the levels of CD3ε levels were uniform among the different groups (FIGS. 9C and 9D).

The Effect of Busulfan on the Host's Immune System

Busulfan is a chemotherapeutic drug mainly used in the treatment of chronic myelogenous leukemia (CML) and is sometimes used for acute leukemias and lymphomas. Interestingly, it is also used in bone marrow and stem cell transplantations. In order to test the effect of busulfan on the immune status, mice in the course of chronic inflammation, which are characterized by immunosuppression as observed during tumor growth, were exposed to busulfan treatment, i.p. As observed in FIG. 10, the treatment with busulfan dramatically decreased the severity of the immunosuppressive environment, as indicated by a significant decline in MDSCs in the spleen (FIG. 10A) and in the blood (FIG. 10B), while the levels of Treg cells remained unchanged (FIG. 10C).

As demonstrated in FIG. 11, the immune status could be detected by analyzing the expression levels of CD247 in cells obtained from the spleen (FIG. 11A), which is a further evidence for the reliability of the CD247 as a marker for the immune status; initial recovery of CD247 expression upon treatment with busulfan treatment (FIG. 11A) was observed while the levels of CD3ε remained uniform among the different groups (FIG. 11B).

The Effect of 5-Fluorouracil on the Host's Immune System 5-fluorouracil (5-FU) is a chemotherapeutic drug that is mainly used in the treatment of the following types of cancers: colorectal cancer [27], basal cell carcinoma and pancreatic cancer. In order to test the effect of this drug on the immune status, mice in the course of chronic inflammation, which are characterized by immuno suppression as observed during tumor growth, were exposed to 5-FU treatment, i.p.

As shown in FIG. 12, the treatment with 5-FU dramatically decreased the severity of the immunosuppressive environment, as indicated by a significant decline in MDSCs in the spleen (FIG. 12A) as well as in the blood (FIG. 12B), while the levels of Treg cells remained unchanged (FIG. 12C).

As demonstrated in FIG. 13, the expression levels of CD247 in T cells recovered significantly in the spleen (FIG. 13A) of inflamed mice treated with 5-FU when compared to inflamed mice that were not treated with 5-FU, demonstrating that CD247 senses the modified immune environment upon treatment with 5-FU. As was observed upon treatment with the other chemotherapeutic drugs, the expression levels of CD3ε were rather constant in all tested group (FIG. 13B).

As demonstrated in FIG. 13, CD247 was not only capable of sensing the recovery from immunosuppression in T cells (FIG. 13A), but also in natural killer (NK) cells (FIG. 13C) and this phenomenon was associated with a recovery of the killing activity primarily mediated via NK cells (FIGS. 13D and 13E).

The Effect of 5-Fluorouracil on Donor T Cells

The ability of the expression levels of CD247 to indicate the immune status of cells treated with 5-FU was also examined in the presence of a combined treatment that included 5-FU and immunotherapy, specifically, adoptive cell transfer. As demonstrated in FIG. 14, a clear significant increase in the expression levels of CD247 was observed for both the host's and donor's cells, upon 5 FU treatment; the expression levels of CD247 was down-regulated in cells transferred to an inflamed host within 24 hours, as in the host cells, while in inflamed mice treated with 5-FU, the adoptive cell transfer was successful since the adoptively transferred cells showed normal CD247 expression levels as the recovered host cells.

These results show that CD247 may indeed serve as a reliable biomarker for detecting recovery from immunosuppression caused by a chemotherapeutic treatment, such as 5-FU or a combination with immunotherapy could be successful as long as CD247 expression levels are steady and close to normal.

Example 3

CD247 is a Biomarker Sensing the Effect of Immune Based Treatment on the Hosts' Immune Status.

Studies performed by the present inventors indicate that TNFα plays a key role in the chronic inflammation induced immunosuppression, by arresting MDSCs at an immature differentiation state and increasing their suppressive activity (Sade-Feldman et. al. submitted). In aiming to assess the in vivo role of TNFα in blocking MDSC maturation in WT-mice exhibiting chronic inflammation. To this end, the TNFα antagonist, etanercept was used and administrated daily, starting from 1 day before the second BCG injection, when the onset of MDSC accumulation was observed in the blood, and until 1 day before the mice were sacrificed. This regimen is schematically illustrated in FIG. 15A. The efficacy of the treatment with etanercept on inflamed WT-mice was evaluated by comparing these mice with inflamed TNFα KO-mice. As demonstrated in FIG. 15B, reduced spleen size and weight were observed in the inflamed etanercept-treated WT-mice compared with the etanercept-untreated inflamed WT group. Significant differences were also observed in the accumulation of MDSCs in the spleen (FIG. 15C) of the etanercept-treated group showing a decreased percentage of MDSCs.

Reduced accumulation of MDSCs within the etanercept-treated group was accompanied by a significant increase in CD11b$^+$CD11c$^+$ and CD11b$^+$F4/80$^+$ cells within the spleen (FIGS. 15D and 15E), indicating an effect on MDSC maturation similar to that observed in the inflamed KO-mice.

Next, the effect of etanercept treatment on the host's immune status as well as on adoptively transferred T- and NK-cells was examined. It should be noted that adoptively transferred T- and NK-cells being a treatment that is frequently used today in different immunotherapeutic regiments for various pathologies [32, 33]. To this end, CFSE-labeled normal splenocytes were administered, i.v., 1 day before cell harvest, at the peak of the inflammatory response (mimicking cell mediated therapies). Upon comparing the expression levels of CD247 in donor (CFSE+) and in host (CFSE−) T- and NK-cells localized in the spleen of inflamed WT-mice to those measured in control-mice it was revealed that etanercept administration to the inflamed WT mice significantly increased the expression of CD247 in T- and NK-cells (FIGS. 15F and 15G, respectively), both in the host's (upper panel) and in the adoptively transferred (donor) cells (lower panel).

The effect of etanercept was also evaluated in-vivo, on NK-cell function under chronic inflammatory conditions. As demonstrated in FIG. 15H, a reconstitution of NK cell cytotoxic activity was observed; a significant elevation in the percentage of specific allogeneic cell clearance was observed in the etanercept-treated group compared with that of the etanercept untreated group, both in the spleen and blood.

Taken together, the results presented in this Example demonstrate that treatment by etanercept enables MDSC maturation and thereby rescues the endogenous (host) immune system as well as of the newly administered (donor) cells, as manifested in the increase in the expression levels of CD247. Moreover, these results demonstrate the feasibility of using CD247 as a reliable marker for evaluating the efficacy of an immunotherapeutic treatment.

Example 4

A Summary of Selected Chemotherapeutics and their In-Vivo Effect on MDSCs

In order to compare the effects of various clinically used chemotherapeutic agents on the immunosuppressive environment generated during chronically inflamed conditions, the mouse model for chronic inflammation was used, as described above and as graphically presented in FIG. 16A. One day after the second BCG injection, when acute inflammation evolved into a chronic one, mice were treated with various chemotherapeutic drugs and two days after the third BCG injection mice were sacrificed and splenocytes and peripheral blood lymphocytes (PBLs) were analyzed. Although MDSC accumulation is significantly elevated in the course of chronic inflammation, following chemotherapy delivery it was observed that while the agents 5-fluorouracil (5-FU), Busulfan and Doxorubicin (Rubex) were able to decrease the Gr1+ CD11b+ MDSC percentage in spleen and PBLs, the agents Irinotecan (CPT-11) and Cyclophosphamide (CP) significantly increased MDSC levels in spleens, with no changes in the blood following CPT-11 treatment, compared to BCG-inflamed group (FIG. 16B-16C). Importantly, the most significant decrease in the MDSC percentage was observed following the 5-FU treatment. To the contrary, the treatment with CPT-11, as well as with CP resulted in a significant accumulation of MDSCs in the spleen and PBLs. As demonstrated in FIG. 16D, except for the treatment with CP, the high percentage of regulatory T cells (Foxp3+Tregs) observed during the chronic inflammation was not altered by any other agent, suggesting an exclusive mode of action for this agent on MDSCs.

Taken together, these results demonstrate that various chemotherapeutic agents selectively and differently affect MDSCs. Since the most drastic and opposing effects on MDSC accumulation were obtained following treatment with 5-FU and CPT-11, and due to the fact that these two agents are very commonly clinically used, their impact on induced immunosuppression was further investigated in a comparative manner, as described below.

Example 5

5-FU and CPT-11 Monotherapies Display an Opposite Effect on MDSC Suppressive Activity The inflammatory S100 proteins, which serve as an autocrine feedback loop, are of the key molecules controlling MDSC accumulation and retention in their immature, suppressive state induced by a given tumor, and a prolonged chronic inflammation [34]. Thus the possibility that chemotherapeutic drugs affect MDSC levels via this pathway was investigated. To this end, as demonstrated in FIG. 17, mRNA levels of S100A8/9 (left panels) and protein levels of the S100A9 protein (right panels) were analyzed in purified MDSCs (FIG. 17A) and in a total splenic population (FIG.

17B). A significant decrease in the mRNA levels of S100A8/9 was observed following 5-FU treatment, which corresponded to decreased amounts of the protein S100A9, as observed in purified MDSCs and total splenic population. Although following treatment with CPT-11 no significant changes in mRNA levels were detected, the protein levels remained high both in purified MDSCs and in the spleen. Without wishing to be bound by theory, these results are consistent with the observed changes in MDSC levels (FIG. 16), suggesting that the influence of the given chemotherapy on MDSCs accumulation and retention in their suppressive stages, depends on the effect of the chemotherapy on S100 proteins; while 5-FU diminishes the inflammatory S100 proteins and decreases MDSC levels, under CPT-11 the S100 levels are kept intensified, supporting elevated levels of MDSCs under chronically inflamed conditions. Since the immunosuppressive environment is a decisive cause for the failure of the anti-tumor immune response, understanding of compounds controlling immunosuppression is crucial.

In order to determine the mechanisms underlying MDSC features under chronically inflamed conditions, the involvement of different mediators and factors that are known to affect the differentiation stage and suppressive abilities of MDSCs were investigated. It is well established that the main inflammatory cytokines involved in MDSC generation and promotion of immunosuppressive activity are IFNγ, TNFα and IL-6 [35, 36] and [Sade-Feldman et. al. Submitted]. The mRNA levels of these cytokines were thus measured in spleen-derived purified MDSCs following a treatment by 5-FU or CPT-11, and in total splenocyte populations. As shown in FIG. 17C, no significant changes in TNFα and IL-6 were found. Surprisingly, the mRNA level of IFNγ was decreased in MDSCs as well as in the total spleen-population following CPT-11 treatment. These results suggest no effect of the 5-FU and CPT-11 agents on the inflammation-promoting cytokines produced during chronically inflamed conditions. Since IFNγ is an important factor to the generation of MDSCs at the first stages of the inflammation, the down-regulation of IFNγ following CPT-11 treatment may be explained by the fact that chronic inflammation had already been established and persists and thus, the enhancement of MDSC rates could be induced by other mechanism(s). Moreover, a decreased production of IFNγ could explain a strong suppression of NK- and T-cell activity, since IFNγ is an autocrine regulator of the activation of these cells.

Since MDSC suppressive activity is mediated, among others, by the secretion of NO and ROS, the levels of NO and ROS following 5-FU and CPT-11 administrations were investigated. As demonstrated in FIG. 17D, NO production was found to be significantly enhanced in the spleen at the chronic inflammation state. Following treatment with 5-FU its level decreased while CPT-11 treatment did not result in any further changes. In contrast, the production of ROS significantly increased following CPT-11 administration while they decreased in the 5-FU treated mice (FIG. 17E). CPT-11 is an inhibitor of topoisomerase I, which is an enzyme that controls the manipulation of DNA structure that is necessary for replication. Thus, the enhancement of ROS production during environmental stress in cells is consistent with the destructive effect of CPT-11, as it was reported for its association with cardiovascular disorders and stroke [37]. Moreover, the decreased levels of both NO and ROS secretion following 5-FU treatment suggests a partial recovery from the suppressive stage generated by the chronic inflammation.

It was previously reported that the mechanism of 5-FU that controls MDSCs comprises the induction of apoptosis [38]. Indeed, upon investigating the levels of cleaved caspase-3, which is a form of the protein which is active and results in cell apoptosis, a significant increase of its expression within MDSCs obtained from 5-FU treated mice was found, similar to that observed in MDSCs under normal, not inflammatory conditions (FIG. 17F). As opposite effect was observed following CPT-11 treatment, where MDSCs displayed decreased levels of cleaved caspase-3, almost the same as were found in spleen-derived MDSCs from chronically inflamed mice (BCG), with a tendency of decrease.

Taken together, these results are consistent with the previously reported apoptotic mechanism of action of 5-FU in targeting MDSCs, and with additional data demonstrating the reduction of pro-inflammatory S100 family proteins by 5-FU, suggesting a possible transition from immature and suppressive stage towards a pathway of differentiation. Indeed, as demonstrated in FIGS. 18G and 18F, the treatment of 5-FU resulted in a significant turning towards differentiated myeloid population of macrophages (CD11b+ F4/80+, FIG. 18G) and dendritic cells (DCs, FIG. 18F) (CD11b+CD11c+). Moreover, as demonstrated in FIGS. 18H and 18I, 5-FU enhanced the maturation of antigen presenting cells (APCs) macrophages (FIG. 18I) and DCs (FIG. 18H) that was reflected by the induced expression of CD80 and MHCII molecules. As to the mode of action of CPT-11, the results suggest a deleterious effect on the immunosuppressive state, where the mode of function is to target different pathways; Aside from the down-regulated mRNA levels of IFNγ and high amounts of the inflammatory protein S100A9, which support elevated percentage of MDSCs (FIG. 16B), the results presented above demonstrate that CPT-11 acts via induction of resistance to apoptosis of spleen-derived MDSCs. Moreover, as demonstrated in FIGS. 18F, 18G and 18H, CPT-11 treatment resulted in a blockage of the myeloid cell differentiation and maturation. Taken together, the results presented above show that 5-FU and CPT-11 act in opposite directions (counteract) and oppositely regulate and influence the MDSCs nature and activity in the course of chronic inflammation.

Example 6

Differential Effects of 5-FU or CPT-11 Monotherapies on T-Cell Activity

In order to check whether the opposing regulatory effects of 5-FU and CPT-11 on the numbers and suppressive activity of MDSCs differently affect immune responses, their effect on T-cell activity was first investigated, by measuring the TCR ξ-chain (CD247) expression in spleens obtained from normal, chronically inflamed and chronically inflamed mice treated with 5-FU or CPT11, in a comparative manner. These results were also demonstrated for each of CPT11 and 5-FU in FIGS. 2 and 13, respectively. As was previously reported [39], down-regulation of CD247 during the chronically inflamed conditions is mediated by MDSCs, resulting in an impaired immune function within the host. As demonstrated in FIGS. 18A and 18B, a significant recovery of CD247 expression was observed both in the spleen and in PBLs following 5-FU treatment, as compared to its expression in chronically inflamed mice which were not administered with a chemotherapeutic treatment. In contrast, FIG. 18A also shows that a strong down-regulation of CD247 was observed in the spleen, with a tendency of decreased expression in PBLs following CPT-11 treatment, as compared to the expression in inflamed mice, indicating a greater suppression of CD247 in spleen with high capacity of the suppressive MDSC population. As demonstrated in FIGS. 18D and 18E, the expression of CD3ε was not down regulated, consistent with previous results of the present inventors, which demonstrated that CD247 is the only TCR subunit being down-regulated during immunosuppression. A correlation between the decreased expression of CD247 and T-cell activity in vitro was also observed. As demonstrated in FIG. 18C, while T-cells derived from chronically inflamed mice showed a decreased ability to proliferate, treatment with CPT-11 significantly diminished their proliferation. Although treatment with 5-FU did not lead to a full recovery of T cells to normal functionality, as compared to T-cells derived from normal, untreated mice, a tendency of a functional recovery was noticed (FIG. 18C). Without wishing to be bound by theory, these results may be explained by an incomplete 5-FU treatment or by the fact that additional pathways are required for the induction of full recovery.

Example 7

Differential Effects of 5-FU or CPT-11 Monotherapies on NK-Cell Activity

In order to investigate other effector immune cells, the impact of 5-FU and CPT-11 was also tested on NK-cells. As shown in FIG. 19A, the expression of CD247 was down-regulated in NK cells obtained from chronically inflamed mice, and was found to be almost completely recovered after 5-FU treatment, whereas after the CPT-11 treatment the expression remained down-regulated with no further decrease. The in vivo activity of NK cells to eliminate transferred allogeneic cells was then investigated. To this end, splenocytes derived from syngeneic (C57BL/6) and allogeneic (BALB/c) normal mice were labeled with low and high concentrations of CFSE, respectively, and administered into C57BL/6 mice. The immunosuppression was verified by the impaired ability of the recipients to clear allogeneic cells by cytotoxic NK cells, 24-48 hours after transferring the syngeneic and allogeneic CFSE labeled cells. As shown in FIGS. 19B and 19C, complete recovery of NK-cell activity was found both in the spleen and PBLs following 5-FU treatment, and a significantly decreased ability to clear allogeneic cells was observed following CPT-11 treatment, as compared to mice treated with BCG alone. Taken together, these results indicate contrasting (or opposing) abilities of 5-FU and CPT-11 to target MDSC numbers and consequently, influence the efficiency of effector NK- and T-cell to respond under chronically inflamed conditions, where the host's immune system benefits from treatment with 5-FU whereas CPT-11 displays rather harmful effects by strengthening the induced immunosuppression.

Example 8

Different Doses of Combined 5-FU/CPT-11 Therapy Decreases MDSC Levels but have Diverse Effects on their Suppressive Activity The basis for a combined treatment comprising the agents 5-FU and CPT-11 is the proven activity of each of these chemotherapeutic agents as a monotherapy, the difference in their mechanisms of action and the lack of cross-resistance. In-vitro studies have shown some additive effects [40], as well as some clinical evidence showing the beneficial effect of the combined therapy [41], that is widely accepted as the first line chemotherapy for colorectal cancer.

However, the combination may also affect the cytotoxic abilities of the drugs. There is a concern regarding the influence of each of these agents on the other one, due to the fact that 5-FU inhibits DNA synthesis, which is required for the active form derivate of CPT-11 (SN38), whereas SN38 causes cell accumulation in a G2 phase, which is resistant to 5-FU [42].

Therefore, the effect of the combinatorial treatment by 5-FU and CPT-11 was next examined on MDSCs levels and suppressive activities. As shown in FIG. 20A, the levels of MDSC in the spleen were significantly decreased in the inflamed mice following the combined treatment. However, as demonstrated in FIG. 20B, although levels of MDSCs were decreased, the expression level of CD247 in splenic T-cells was not recovered, suggesting that the MDSC suppressive function was still high, indicating and immunosuppressive status. Indeed, the suppressive activity of MDSCs from inflamed mice treated with the combined therapy was enhanced significantly as reflected by the levels of NO (FIG. 20C) and hROS (FIG. 20D). The MDSCs enhanced suppressive activity correlated with an immunosuppressive immune status. NK cells in inflamed mice treated with the combined therapy showed less killing activity of allogeneic cells as compared with the untreated inflamed mice (FIG. 20E, 20F). These results imply that CPT11 treatment is able to overcome the beneficial effects of 5FU. However, when lower doses of combined chemotherapeutic agents (5FU and CPT11) were administered, the marked reduction of % MDSCs (FIG. 20G) was also followed by elevated levels of CD247 (FIG. 20H). The levels of NO were also significantly reduced in response to the combined treatment (FIG. 20I), but monotherapy using 5FU, showed better results also in reducing hROS (FIG. 20J).

These results demonstrate the feasibility of using CD247 as a sensitive marker enabling the assessment of different doses of therapeutic agent.

Example 9

Selected Chemotherapeutics In-Vivo Effect on MDSCs in the Course of Colon Cancer (CRC)

In order to investigate whether clinically used chemotherapeutic agents affect the immune-based environment that is generated during tumor development, a mouse model for inducible CRC was established. To this end, mice were subjected to two injections of the mutagen azoxymethane (AOM), followed by two weekly administrations of dextran sulfate sodium (DSS), which was added to the drinking water. After the second DSS treatment (as described in the Experimental procedures), a period of time when acute inflammation evolves into a chronic one, mice were treated with chemotherapeutic drugs and three weeks after the second DSS treatment mice were sacrificed and splenocytes and PBLs were analyzed. As demonstrated in FIG. 21, MDSC accumulation was significantly elevated in the course of CRC development (FIG. 21A, 21C). While following chemotherapy delivery of 5-FU, a significant decrease in the level of the Gr1+CD11b+ double positive MDSC percentage in spleen and PBLs was observed, CPT-11 significantly increased MDSC levels in spleens, with no changes in the blood following CPT-11 treatment, as compared to the AOM/DSS group (FIG. 21A, 21C). Such changes in the generated environment were sensed by levels of CD247 expression; as shown in FIGS. 21B and 21D, CD247 expression decreased significantly in the spleen and blood of mice with CRC compared with normal mice. Upon treatment with the chemotherapeutic drug 5FU, CD247 expression levels significantly recovered, while following treatment with CPT11, CD247 levels were low as in the case of CRC-bearing, non-treated mice (FIG. 21B). These results indicate that CD247 expression levels can predict the inflammatory stage and associated hosts' immune status in the course of colon cancer (CRC). Moreover, measurements of the expression levels of CD247 may also provide an indication of therapy efficacy as shown herein, upon using 5FU and CPT11, each of them exhibiting an opposing effect on the host's immune system; while 5FU leads to a recovery from MDSC-mediated immunosuppression, CPT11 treatment maintains the immunosuppressive environment and in some cases, leads to its enhancement.

In order to investigate how the clinically used combination of the chemotherapeutic agents 5-FU and CPT-11 affects the immunosuppressive environment generated during CRC, CRC-bearing mice were treated with 5-FU alone or in combination with CPT-11, as described above. The results, demonstrated in FIG. 22, revealed that the extent of the effect the combinatorial treatment had on MDSC accumulation during CRC in mice was lower than that observed for 5FU alone (FIG. 22A, 22C), with MDSC levels in the spleen and PBLs still being high. Most significantly, measurements of CD247 expression level were able to indicate that the combinatorial treatment did not alter the immune status and it was still deteriorated as opposed to the treatment with 5-FU as a single treatment (FIGS. 2B and 22D).

Indeed, when measuring the specific immunosuppressive features of the MDSCs following the different treatments (i.e. 5-FU alone or in combination with CPT11), the results revealed that although some decrease in the percentage of the MDSCs was observed upon the combined 5FU and CPT11 treatment, as shown in FIG. 22A, only in the spleen, NO and ROS production, which are significant markers of an immune-suppressive environment, remained as high as in the non-treated CRC-bearing mice and the only treatment that decreased the suppressive activity was with 5FU alone, as demonstrated in FIG. 23.

Importantly, these results revealed that measuring MDSC levels is insufficient for obtaining indications of the immunosuppressive environment, and that it is required to measure their immunosuppressive features as well. The results highlight the significance of using CD247 as a biomarker for the evaluation of the host's immune status before, during and after treatments, for providing clues as to the immune-suppressive status of a subject prior to the onset of a given therapy or for providing clues as to the specific efficacy of a given therapy on the immune system. Therefore, it is important to monitor not only the effect of the treatment on the tumor itself but also to assess the effect thereof on the host's immune system. If the latter is still suppressed, a combat of the host against residual tumor cells, such as for example in a case of metastases, will be impossible.

It important to note that in each of the experiments performed (presented in FIG. 21 and FIG. 22), pathological macroscopic and microscopic tests have been performed on the structure of the colon and counts were made of the tumor loads. The curable effects where observed only when the mice were treated with 5FU and not with CPT11 alone or with the 5FU and CPT11 combination. These results correlated with CD247 measurements. These results are similar to those obtained when using the combined treatment on the inflamed mice.

Example 10

The Immunosuppressive Environment is Detected within the Tumor Target Site

Figure 24A:
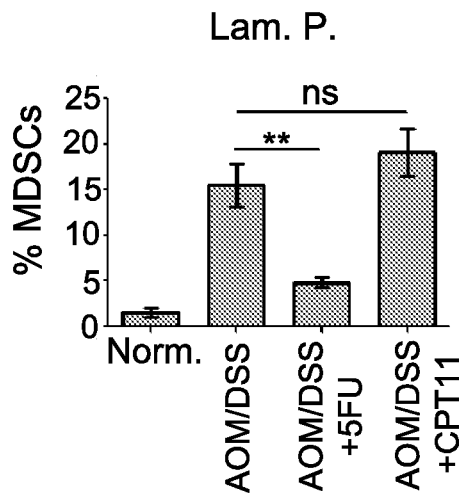
Figure 24B:
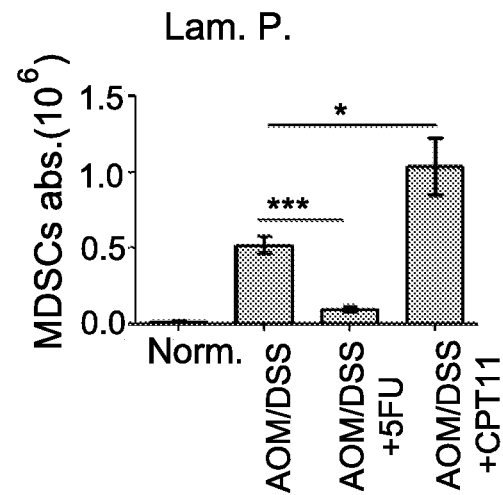
Figure 24C:
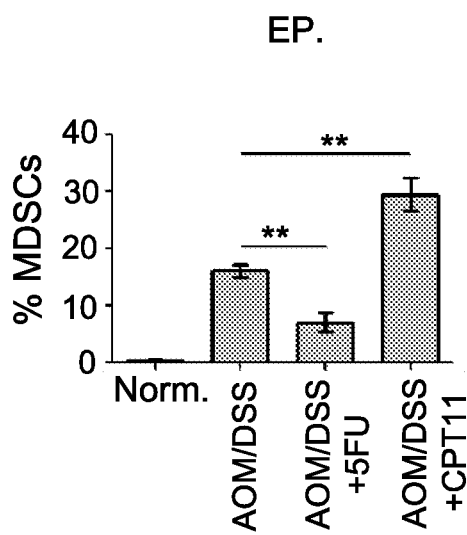
Figure 24D:
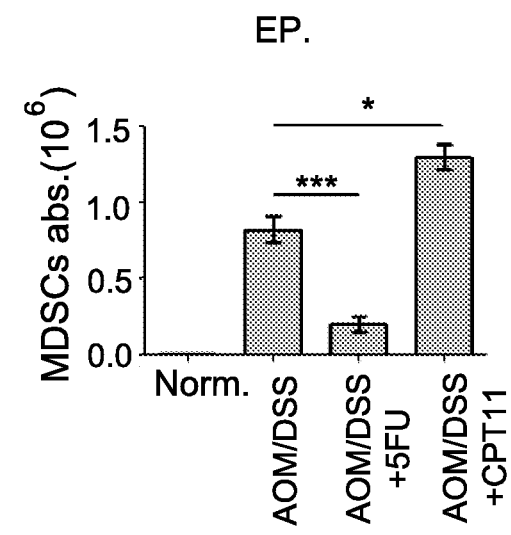
Figures 24E, 24F:
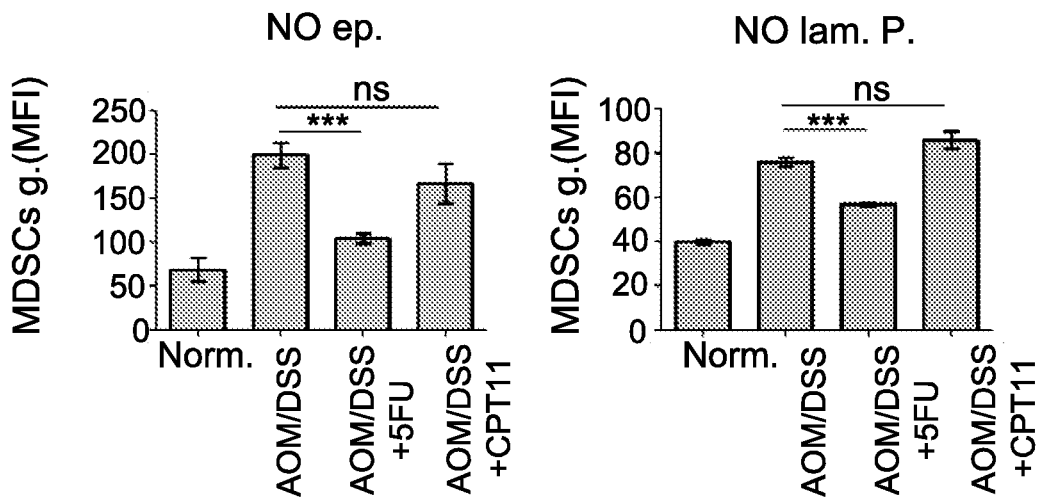
Figures 24G, 24H:
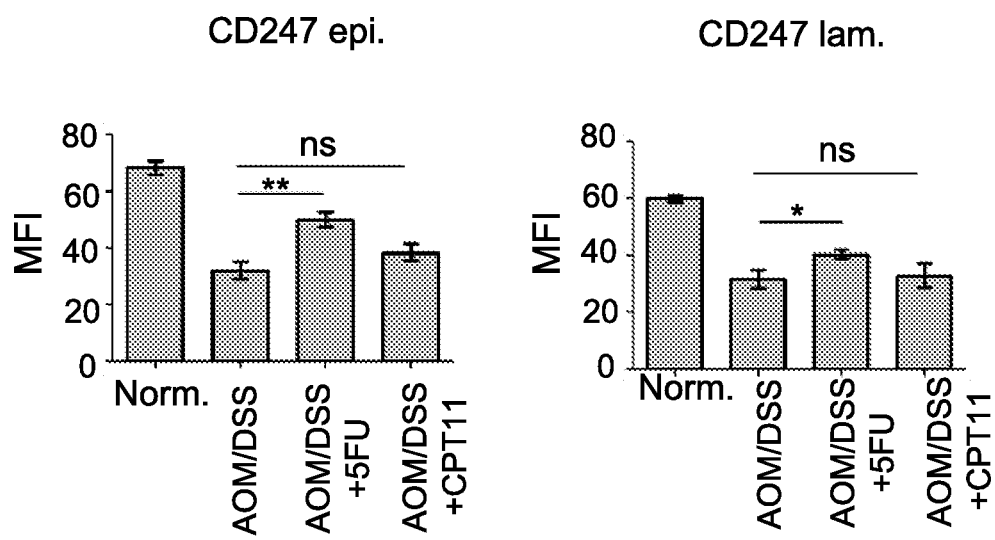

The inventors next examined the option of using the tumor tissue for assessing the efficacy of treatment with either 5FU or CTP11 monotherapies. Therefore, the mouse model for inducible CRC was used as described by Example 9. Colons from three independent experiments were isolated and single cell suspensions of the epithel and lamina propria were performed. As shown in FIG. 24A, MDSCs infiltration in the lamina propria (FIGS. 24A and 24B) and in colon epithelial tissue (FIGS. 24C and 24D), were significantly reduced in response to 5FU treatment, however, treatment with CPT11 significantly increased MDSCs in the tumor tissue. As shown in FIGS. 24E and 24F, $NO^-$ production was reduced in both epithel and lamina propria in response to 5FU treatment. CD247 expression levels in T cells infiltrating the different colon regions were elevated in response 5FU treatment (FIGS. 24G and 24H).

As shown in the Kaplan-Meyer curve presented in FIG. 25B, a clear correlation between the elevated expression levels of CD247 in response to 5FU treatment (FIG. 25G, 25H) and the increased survival of mice treated with 5FU, was revealed. Reduced levels of CD247 in the CPT11 treated animals were also reflected in a reduced survival rate.

These results clearly indicate that CD247 may be used as a sensitive marker using samples obtained from the tumor tissue. Moreover, these results indicate that the levels of CD247 in the tumor tissue may predict the responsiveness of a subject to a certain treatment and therefore may be used as a prognostic tool for assessing disease progression and survival rate.

Example 11

CD247 as a Biomarker for Assessing the Suitability of a Patient to a Therapy

Blood samples were collected from approximately 40 colon cancer (CRC) patients that are being subjected to different combinations of 5FU and CPT11 treatments. Blood samples were collected prior to and at different time points during the treatment. Next, the parameters tested in the mouse model system are to be applied to the human samples (namely, the levels of MDSCs, the levels of ROS and NO production as well as the level of expression of CD247), to provide a preliminary proof of concept of using the level of expression of CD247 as a key indication to the patient's immune status prior to or during treatment, and in order to examine whether this marker may be used for staging the disease and for determining the efficacy of a given therapy on the course of the treatment. This approach will enable the design of a personalized treatment, which uses CD247 as a powerful diagnostic tool.

The invention claimed is:

1. A method for determining the efficacy of a treatment with a disease-targeted therapeutic agent on a patient suffering from a disease associated with a chronic inflammatory condition, during, or after the onset, or initiation of said treatment, wherein said disease-targeted therapeutic agent is at least one of a chemotherapeutic agent and/or at least one immunotherapeutic agent, wherein said disease associated with a chronic inflammatory condition is selected from the group consisting of a proliferative disorder, an autoimmune disorder, diabetes, an inflammatory disease, and an infectious disease, said method comprising:

determining the suitability, efficacy of, or responsiveness to, the diseases-targeted therapeutic agent, by administering to the patient a predetermined dose of the disease-targeted therapeutic agent;

obtaining at least one post-treatment biological sample from the patient during or after the onset or initiation of treatment, the post-treatment biological sample comprising cells;

measuring an expression level of TCR-ζ chain in the cells of the at least one post-treatment biological sample of the patient, comprising detecting in vitro an amount of the TCR-ζ chain in the cells; and comparing the level of expression of the TCR-ζ chain in the at least one post-treatment biological sample, to a respective predetermined cutoff value for the TCR-ζ chain to determine the level of TCR-ζ chain expression in the at least one post-treatment biological sample that is significantly below the predetermined cutoff value determined by statistical determination, or the level of the TCR-ζ chain expression in the at least one post-treatment biological sample that is at, about or above the predetermined cutoff value;

stopping treatment of the patient with the disease-targeted therapeutic agent based on the measured expression level of TCR-ζ chain in the cells, wherein the level of the TCR-ζ chain expression in the at least one post-treatment biological sample is significantly below the predetermined cutoff value indicates immunosuppression in the patient and that the patient is not suitably responding to treatment, and thereafter, treating the patient for immunosuppression, or continuing treatment of the patient with the disease-targeted therapeutic agent for a predetermined period of time based on the measured expression level of TCR-ζ chain in the cells, wherein the level of the TCR-ζ chain expression in the at least one post-treatment biological sample is at about or above the predetermined cutoff value indicates that the patient is responding to treatment with the disease-targeted therapeutic agent, and during said predetermined period of time, periodically monitoring the level of the TCR-ζ chain expression in at least one monitoring biological sample obtained from the patient, wherein if during said periodic monitoring, the level of the TCR-ζ chain expression in the at least one monitoring biological sample is significantly below the predetermined cutoff value, indicating immunosuppression in the patient and that the patient is not suitably responding to treatment with the disease-targeted therapeutic agent, stopping treatment of the patient with the disease-targeted therapeutic agent and thereafter, treating the patient for immunosuppression, thereby determining efficacy of a treatment with a disease-targeted therapeutic agent on a patient suffering from a disease associated with a chronic inflammatory condition.

2. The method according to claim 1, further comprising:

obtaining a pre-treatment biological sample from the patient prior to onset of administering to the patient the predetermined dose of the disease-targeted therapeutic agent, the pre-treatment biological sample comprising cells;

measuring an expression level of TCR-ζ chain in the cells of the pre-treatment biological sample of the patient, comprising detecting in vitro an amount of the TCR-ζ chain in the cells of the pre-treatment biological sample;

calculating a rate of change in TCR-ζ chain expression in response to administering to the patient the disease-targeted therapeutic agent between the level of TCR-ζ chain expression in the at least one post-treatment biological sample of the patient and the TCR-ζ chain expression in the pre-treatment biological sample of the patient, comprising comparing the level of TCR-ζ chain expression in the at least one post-treatment biological sample of the patient and the TCR-ζ chain expression in the pre-treatment biological sample of the patient;

determining the efficacy of treatment with the disease-targeted therapeutic agent on the patient, comprising comparing the rate of change in TCR-ζ chain expression in response to the treatment with the disease-targeted therapeutic agent to a corresponding pre-determined standard rate of change, when the rate of change in TCR-ζ chain expression in response to the treatment with the disease-targeted therapeutic agent is significantly below the corresponding pre-determined standard rate of change, indicating that the patient is immunosuppressed and not responding to treatment with the disease-targeted therapeutic agent, treatment of the patient with the disease targeted therapeutic agent is stopped, and thereafter, treating the patient for immunosuppression, or when the rate of change in TCR-ζ chain expression in response to the treatment with the disease-targeted therapeutic agent is at about or above the corresponding pre-determined standard rate of change, indicating that the patient is responding to treatment with the disease targeted therapeutic agent and the treatment is continued.

3. The method according to claim 1, wherein said periodically monitoring step further comprises monitoring the continued efficacy of, the disease-targeted therapeutic agent, in the patient, wherein said obtaining step comprises obtaining two or more temporally separated post-treatment biological samples from the patient during or after onset or initiation of treatment of the patient with the disease targeted therapeutic agent, at least one post-treatment biological sample is obtained after the onset or initiation of the treatment of the patient with the disease targeted therapeutic agent;

measuring an expression level of TCR-ζ chain in the cells of each of the two or more temporally separated post-treatment biological samples of the patient, comprising detecting in vitro an amount of the TCR-ζ chain in the cells of each of the two or more temporally separated post-treatment biological samples;

calculating a rate of change in TCR-ζ chain expression in response to the treatment of the patient with the disease targeted therapeutic agent, between the level of TCR-ζ chain expression in each of the two or more temporally separated post-treatment biological samples of the patient, comprising comparing the level of TCR-ζ chain expression in each of the two or more temporally-separated post-treatment biological samples of the patient;

comparing the rate of change in TCR-ζ chain expression in the two or more temporally separated post-treatment biological samples of the patient in response to the treatment of the patient with the disease targeted therapeutic agent, to a corresponding pre-determined standard rate of change, when the rate of change in TCR-ζ chain expression in response to the treatment with the disease targeted therapeutic agent is significantly below the corresponding pre-determined standard rate of change, thereby indicating that the patient is immunosuppressed and not responding to treatment with the disease-targeted therapeutic agent, and treatment of the patient with the disease targeted therapeutic agent is stopped, and thereafter, treating the patient for immunosuppression, or when the rate of change in TCR-ζ chain expression in response to the treatment with the disease targeted therapeutic agent is at about or above the corresponding pre-determined standard rate of change, indicating that the patient is responding to treatment with the disease-targeted therapeutic agent and said treatment is continued until the next monitoring period or time interval of said periodically monitoring step of claim 1, whereby continued efficacy of the disease-targeted therapeutic agent treatment is monitored.

4. The method according to claim 1, wherein the step of measuring an expression level of TCR-ζ chain in the cells of the at least one post-treatment biological sample comprises contacting detection molecules specific for TCR-ζ chain expression with the at least one post-treatment biological sample or with a nucleic acid or protein product obtained therefrom.

5. The method of claim 4, further comprising further contacting the at least one post-treatment biological sample or a nucleic acid or protein product obtained therefrom, with detection molecules specific for at least one reference control protein characterized as displaying a constant expression pattern in samples from:

an un-treated patient suffering from a chronic inflammatory condition, a patient treated with the disease-targeted therapeutic agent exhibiting a therapeutic response, a patient that exhibits a non-therapeutic response to the same disease-targeted therapeutic agent, and healthy individuals not suffering from a disease associated with chronic inflammatory condition, comprising at least one of CD3ε, CD3δ, CD3γ, TCRα, TCRβ, and CD56.

6. The method according to claim 4, wherein the detection molecules are selected from the group consisting of isolated detection amino acid molecules, and isolated detection nucleic acid molecules and any combinations thereof.

7. The method according to claim 6, wherein the detection amino acid molecule specific for TCR-ζ chain is an isolated antibody that specifically recognizes and binds TCR-ζ chain.

8. The method according to claim 1, further comprising at least one of the following:

determining a myeloid-derived suppressor cells (MDSCs) population in the at least one post-treatment biological sample of the patient, comparing the determined MDSCs population with a corresponding predetermined cutoff value, and stopping treatment of the patient with the disease-targeted therapeutic agent when the determined MDSCs population is significantly above the corresponding predetermined cutoff value indicating immunosuppression, or continuing treatment of the patient with the disease-targeted therapeutic agent when the determined MDSCs population is at or about the corresponding predetermined cutoff value, determining the expression levels of S100A8 and/or S100A9 proteins in the at least one post-treatment biological sample of the patient, comparing the determined expression levels of S100A8 and/or S100A9 proteins with a corresponding predetermined cutoff value, and stopping treatment of the patient with the disease-targeted therapeutic agent when the determined expression levels of S100A8 and/or S100A9 proteins are significantly above the corresponding predetermined cutoff value indicating immunosuppression, or continuing treatment of the patient with the disease-targeted therapeutic agent when the determined expression levels of S100A8 and/or S100A9 proteins are at or about the corresponding predetermined cutoff value, determining the levels of cleaved caspase 3 in the at least one post-treatment biological sample of the patient, comparing the determined level of cleaved caspase 3 with a corresponding predetermined cutoff value, and stopping treatment of the patient with the disease-targeted therapeutic agent when the determined level of cleaved caspase 3 is significantly below the corresponding predetermined cutoff value indicating immunosuppression, or continuing treatment of the patient with the disease-targeted therapeutic agent when the determined level of cleaved caspase 3 is at or about the corresponding predetermined cutoff value, and determining at least one of intracellular nitric oxide (NO) and reactive oxygen species (ROS) production in the at least one post-treatment biological sample of the patient, comparing the determined at least one intracellular nitric oxide (NO) and reactive oxygen species (ROS) production level with a corresponding predetermined cutoff value, and stopping treatment of the patient with the disease-targeted therapeutic agent when the determined at least one intracellular nitric oxide (NO) and reactive oxygen species (ROS) is significantly above the corresponding predetermined cutoff value indicating immunosuppression, or continuing treatment of the patient with the disease-targeted therapeutic agent when the determined at least one intracellular nitric oxide (NO) and reactive oxygen species (ROS) production level is at or about the corresponding predetermined cutoff value.

9. The method according to claim 1, wherein the disease is selected from the group consisting of inflammatory bowel disease (IBD), ulcerative colitis, Crohn's disease, fatty liver disease, rheumatoid arthritis, systemic lupus erythematosus (SLE), Eaton-Lambert syndrome, Goodpasture's syndrome, Greave's disease, Guillain-Barr syndrome, autoimmune hemolytic anemia (AIHA), hepatitis, multiple sclerosis (MS), myasthenia gravis, a plexus disorders, acute brachial neuritis, polyglandular deficiency syndrome, primary biliary cirrhosis, scleroderma, thrombocytopenia, thyroiditis, Hashimoto's disease, Sjogren's syndrome, allergic purpura, psoriasis, mixed connective tissue disease, polymyositis, dermatomyositis, vasculitis, polyarteritis nodosa, arthritis, alopecia areata, polymyalgia rheumatica, Wegener's granulomatosis, Reiter's syndrome, Behget's syndrome, ankylosing spondylitis, pemphigus, bullous pemphigoid, and dermatitis herpetiformis.

10. The method according to claim 1, wherein the disease is a proliferative disorder.

11. The method according to claim 1, wherein the chemotherapeutic agent is at least one of an alkylating agent, an anti-metabolite, a plant alkaloid, a terpenoid, a taxane, an anthracycline, a topoisomerase inhibitor, a cytotoxic antibiotic, and an antitumor agent.

12. The method according to claim 1, wherein the immune-therapeutic agent is at least one of adoptive cell transfer, a cancer vaccine, antibody-based therapy, a hormone, competing receptors, a cytokine, or any combination thereof.

13. The method according to claim 1, wherein the post-treatment biological sample is any one of a blood sample, a spleen biopsy, cells from lymph nodes, and a tissue biopsy.

14. The method of claim 1, wherein when the level of the TCR-ζ chain expression in the at least one post-treatment biological sample is significantly below the predetermined cutoff value, indicating immunosuppression in the patient and that the patient is not suitably responding to the disease-targeted therapeutic agent treatment, said treatment with the disease-targeted therapeutic agent is stopped, and thereafter, the patient is treated for immunosuppression, or wherein when the level of the TCR-ζ chain expression in the at least one monitoring biological sample is significantly below the predetermined cutoff value, indicating immunosuppression and that the patient is not suitably responding to the disease-targeted therapeutic agent treatment in the patient, said treatment with the disease-targeted therapeutic agent is stopped, and thereafter, the patient is treated for immunosuppression.

15. The method of claim 14, further comprising after or simultaneously with treating the patient for immunosuppression, treating the patient with a different disease-targeted therapeutic agent.

16. The method of claim 1, wherein after stopping treatment of the patient with the disease-targeted therapeutic agent, and after or simultaneously with treating the patient for immunosuppression, treating the patient with a different disease-targeted therapeutic agent, or during said predetermined period of time, after stopping treatment of the patient with the disease-targeted therapeutic agent, and after or simultaneously with treating the patient for immunosuppression, treating the patient with a different disease-targeted therapeutic agent.

* * * * *